(12) United States Patent
Hansford et al.

(10) Patent No.: US 7,632,678 B2
(45) Date of Patent: Dec. 15, 2009

(54) CANCER STEM CELLS AND USES THEREOF

(75) Inventors: Loen M. Hansford, Toronto (CA); Kristen M. Smith, Toronto (CA); Alessandro Datti, Toronto (CA); Freda M. Miller, Toronto (CA); David R. Kaplan, Toronto (CA)

(73) Assignee: The Hospital for Sick Children, Toronto, Ontario (CA)

( * ) Notice: Subject to any disclaimer, the term of this patent is extended or adjusted under 35 U.S.C. 154(b) by 230 days.

(21) Appl. No.: 11/562,798

(22) Filed: Nov. 22, 2006

(65) Prior Publication Data

US 2008/0038770 A1 Feb. 14, 2008

Related U.S. Application Data

(60) Provisional application No. 60/739,337, filed on Nov. 23, 2005.

(51) Int. Cl.
*C12Q 5/08* (2006.01)
*C12Q 5/02* (2006.01)

(52) U.S. Cl. ..................................... 435/368; 435/390

(58) Field of Classification Search ....................... None
See application file for complete search history.

(56) References Cited

U.S. PATENT DOCUMENTS

| 4,628,062 A | 12/1986 | Opitz et al. |
| 6,787,355 B1 | 9/2004 | Miller et al. |
| 2003/0203856 A1 | 10/2003 | Rosazza et al. |
| 2005/0202019 A1 | 9/2005 | Murphy et al. |

OTHER PUBLICATIONS

Hirschmann-Jax et al. A Distinct "Side Population" of Cells With High Drug Efflux Capacity in Human Tumor Cells; Proceedings of the National Academy of Sciences, vol. 101, No. 39 (2004) pp. 14228-14233.*
Walton et al. Characteristics of Stem Cells From Human Neuroblastoma Cell Lines and in Tumors; Neoplasia, vol. 6, No. 6 (2004) pp. 838-845.*
Gazitt et al. Isolation and Characterization of an Early T-Helper/Inducer Cell Line With a Unique Pattern of Surface Phenotype, Constitutive Cytokine Secretion and MYC Oncogene Expression; Leukemia, vol. 7, No. 12 (1993) pp. 2034-2044.*
Brodeur, G. "Neurblastoma: Biological Insight into a Clinical Enigma." *Nature Reviews: Cancer*, 3:203-216, (Mar. 2003).
Mars, J. "The Biological Basis for Neurblastoma Heterogeneity and Risk Stratisfication." *Current Opinions in Pediatrics*, 17: 7-13, (2005).
Van Limpt et al., "Phox2B Mutations and the Delta-Notch Pathway in Neuroblastoma." *Cancer Letters*, 228: 59-63, (2005).
Pardal, et al. "Applying the Principles of Stem-Cell Biology to Cancer." *Nature Reviews: Cancer*, 3: 895-902, (Dec. 2003).
Beachy, et al. "Tissue Repair and Stem Cell Renewal in Carcinogenesis." *Nature*, 432:324-331, (Nov. 2004).
Warner, et al. "Concepts of Human Leukemic Development." *Oncogene*, 23: 7164-7177, (2004).
Hamburger, A. & Salmon, S. "Primary Bioassay of Human Myeloma Stem Cells." *The Journal of Clinical Investigation*, 60: 846-854, (Oct. 1977).
Heppner, G. "Tumor Heterogeneity." *Perspectives in Cancer Research*, 44:2259-2265, (Jun. 1984).
Singh, et al. "Cancer Stem Cells in Nervous System Tumors." *Oncogene*, 23:7267-7273, (2004).
Al-Hajj, M. & Clarke, M. "Self-Renewal and Solid Tumor Stem Cells." *Oncogene*, 23:7274-7282, (2004).
Lapidot, et al. "A Cell Initiating Human Acute Myeloid Leukaemia after Transportation into SCID Mice." *Letters to Nature*, 367:645-648, (Feb. 1994).
Bonnet, D. & Dick, J. "Human Acute Myeloid Leukemia is Organized as a Hierarchy that Originates from a Primitive Hematopoietic Cell." *Nature Medicine*, 3:730-737, (Jul. 1997).
Al-Hajj, et al. "Perspective Identification of Tumorigenic Breast Cancer Cells." *Proceedings of the National Academy of the Sciences USA*, 100:3983-3988, (Mar. 2003).
Singh, et al. "Identification of Human Brain Tumour Initiating Cells." *Nature*, 432:396-401, (Nov. 2004).
Van Noesel, et al. "Neuroblastoma 4S: A Heterogeneous Disease with Variable Risk Factors and Treatment Strategies." *Cancer*, 80:834-843, (Sep. 1997).
Toma, et al. "Isolation of Multipotent Adult Stem Cells from the Dermis of Mammalian Skin." *Nature Cell Biology*, 3:778-784, (Sep. 2001).
Fernandes, et al. "A Dermal Niche for Multipotent Adult Skin-Derived Precursor Cells." *Nature Cell Biology*, 6:1082-1093, (Nov. 2004).
Toma, et al. "Isolation and Characterization of Multipotent Skin-Derived Precursors from Human Skin." *Stem Cells*, 23:727-737, (2005).
Christiansen, et al. "Molecular Control of Neural Crest Formation, Migration and Differentiation." *Current Opinion in Cell Biology*, 12:719-724, (2000).

(Continued)

*Primary Examiner*—Jon P Weber
*Assistant Examiner*—Paul C. Martin
(74) *Attorney, Agent, or Firm*—Vedder Price P.C.; Ajay A. Jagtiani

(57) ABSTRACT

Disclosed are enriched preparations of neuroblastoma tumor initiating cells (NB TICs). The NB TICs are capable of self-renewal, initiating neuroblastoma tumor growth in vivo and are capable of being passaged in high frequency. These NB TICs have chromosomal abnormalities and are capable of giving rise to secondary tumor spheres. Methods are also disclosed for preparing the enriched preparations of NB TICs, such as from neuroblastoma tumor tissue and metastasized bone marrow. Also disclosed are methods of screening candidate substances to identify therapeutic agents for the treatment of neuroblastoma. Methods are also provided for screening a sample for neuroblastoma, as well as for screening a sample to identify the stage of neuroblastoma present. Kits are also provided for selecting appropriate anti-neuroblastoma compounds for a patient, and utilize isolated compositions of the patients' neuroblastoma tumor initiating cells. In this manner, a customized medicinal profile for the patient may be devised.

22 Claims, 38 Drawing Sheets

OTHER PUBLICATIONS

Ambros, et al. "Disseminated Tumor Cells in the Bone Marrow—Chances and Consequences of Microscopical Detection Methods." *Cancer Letters*, 197:29-34, (2003).

Miettinen, et al. "Monoclonal Antibody NB84 in the Differential Diagnosis of Neuroblastoma and Other Small Round Cell Tumors." *The American Journal of Surgical Pathology*, 22:327-232, (1998).

Labrosse, et al. "Catecholamine Metabolism in Neuroblastoma." *J Natl Cancer Inst*, 57:633-638, (Sep. 1976).

Barnabe-Heider, F & Miller, F. "Endogenously Produced Neurotrophins Regulate Survival and Differentiation of Cortical Progenitors via Distinct Signaling Pathways." *The Journal of Neuroscience*, 23(12):5149-5160, (Jun. 2003).

Marsh, et al. "SHP-1 Negatively Regulates Neuronal Survival by Functioning as a TrkA Phosphatase." *The Journal of Cell Biology*, 163(5):999-1010, (2003).

Lo Piccolo, et al. "GD2 Synthase: A New Molecular Marker for Detecting Neuroblastoma." *Cancer*, 92(4):924-931, (Aug. 2001).

Fernandes, et al. "Analysis of the Neurogenic Potential of Multipotent Skin-Derived Precursors." *Experimental Neurology*, 201:32-48, (2006).

Hafer, et al. "Neuroblastoma cells can express the hematopoietic progenitor cell antigen CD34 as detected at surface protein and mRNA level." *Journal of Neuroimmunology*, 96:201-206, (1999).

Khanna, et al. "Biologically Relevant Orthotopic Neuroblastoma Xenograft Models: Primary Adrenal Tumor Growth and Spontaneous Distant Metastasis." In Vivo, 16:77-86, (2002).

Nakagawara, A & Ohira, M. "Comprehensive genomics linking between neural development and cancer: neuroblastoma as a model." *Cancer Letters*, 204:213-224, (2004).

Ohira, et al. "Expression profiling using a tumor-specific cDNA microarray predicts the prognosis of intermediate risk neuroblastomas." *Cancer Cell*, 7:337-350, (Apr. 2005).

Weiss, et al. "Targeted expression of MYCN causes neuroblastoma in transgenic mice." *The Embo Journal*, 16(11):2985-2995, (1997).

Elshamy, et al. "Growth Arrest Failure, G1 Restriction Point Override, and S Phase Death of Sensory Precursor Cells in the Absence of Neurotrophin-3." *Neuron*: 21:1003-1015, (Nov. 1998).

Lasorella, et al. "Id2 Is Critical for Cellular Proliferation and Is the Oncogenic Effector of N-Myc in Human Neuroblastoma." *Cancer Research*, 62:301-306, (Jan. 2002).

Valsesia-Whittmann, et al. "Oncogenic cooperation between H-Twist and N-Myc overrides failsafe programs in cancer cells." *Cancer Cell*, 6:625-630, (Dec. 2004).

Dubreuil, et al. "The Phox2b transcription factor coordinately regulates neuronal cell cycle exit and identity." *Development*, 127:5191:5201, (2000).

Pattyn, et al. "Specification of the Central Noradrenergic Phenotype by the Homeobox Gene Phox2b." *Mollecular and Cellular Neuroscience*, 15:235-243, (2000).

Pozniak, etal. "An Anti-Apoptotic Role for the p53 Family Member, p73, During Developmental Neuron Death." *Science*, 289:304-306, (Jul. 2000).

Casciano, et al. "Expression of ΔNp73 is a molecular marker for adverse outcome in neuroblastoma patients." *Cell Death and Differentiation*, 9:246-251, (2002).

Matsumoto, et al. "Expression of Brain-derived Neurotrophic Factor and p145$^{TrkB}$ Affects Survival, Differentiation, and Invasiveness of Human Neuroblastoma Cells." *Cancer Research*, 55:1798-1806, (Apr. 1995).

Jaboin, et al. "Brain-derived Neurotrophic Factor Activation of TrkB Protects Neuroblastoma Cells from Chemotherapy-induced Apoptosis via Phosphatidylinositol 3'-Kinase Pathway." *Cancer Research*, 62:6756-6763, (Nov. 2002).

Kaplan, et al. Induction of TrkB by Retinoic Acid Mediates Biologic Responsiveness to BDNF and Differentiation of Human Neuroblastoma Cells. *Neuron*, 11:321-331, (Aug. 1993).

Lucarelli, et al. "Activation of trk-A but not trk-B Signal Transduction Pathway Inhibits Growth of Neuroblastoma Cells." *European Journal of Cancer*, 33:2068-2070, (1997).

Lavoie, et al. "TrkA Induces Apoptosis of Neuroblastoma Cells and Does So via a p53-dependent Mechanism." *The Journal of Biological Chemistry*, 280:29199-29207, (Aug. 2005).

Wartiovaara, et al. "N-myc Promotes Survival and Induces S-Phase Entry of Postmitotic Sympathetic Neurons." *The Journal of Neuroscience*, 22:815-824, (Feb. 2002).

Atwal, et al. "The TrkB-Shc Site Signals Neuronal Survival and Local Axon Growth via MEK and PI3-Kinase." *Neuron*, 27:265-277, (Aug. 2000).

Toma, et al. "Evidence That Helix-Loop-Helix Proteins Collaborate with Retinoblastoma Tumor Suppressor Protein to Regulate Cortical Neurogenesis." *The Journal of Neuroscience*, 20(20):7648-7656, (Oct. 2000).

Ellis, J & Shuyuan, Y. "Retrovirus Silencing and Vector Design: Relevance to Normal and Cancer Stem Cells?" *Current Gene Therapy*, 5:367-373, (2005).

Ellis, J. "Silencing and Variegation of Gammaretrovirus and Lentivirus Vectors." *Human Gene Therapy*, 16:1241-1246, (Nov. 2005).

McKenzie, et al. "Skin-Derived Precursors Generate Myelinating Schwann Cells for the Injured and Dysmyelinated Nervous System." *The Journal of Neuroscience*, 26(24):6651-6660, (Jun. 2006).

Torkin, et al. "Induction of caspase-dependent, p53-mediated apoptosis by apigenin in human neuroblastoma." *Molecular Cancer Therapeutics*, 4:1-11, (2005).

Barnabe-Heider, et al. "Evidence that Embryonic Neurons Regulate the Onset of Cortical Gliogenesis via Cardiotrophin-1." *Neuron*, 48:253-265, (Oct. 2005).

Guzman, et al. "The sesquiterpene lactone parthenolide induces apoptosis of human acute myelogenous leukemia stem and progenitor cells." *Blood*, 105(11):4163-4169, (Jun. 2005).

Singh, et al. "Identification of a Cancer Stem Cell in Human Brain Tumors." *Cancer Research*, 63:5821-5828, (Sep. 2003).

Reynolds, B. & Weiss, S. "Clonal and Population Analyses Demonstrate That an EGF-Responsive Mammalian Embryonic CNS Precursor Is a Stem Cell." *Developmental Biology*, 175:1-13, (1996).

Clarke, et al. "Cancer Stem Cells—Perspectives on Current Status and Future Directions: AACR Workshop on Cancer Stem Cells." *Cancer Research*, 66(19):9339-9344, (Oct. 2006).

Fang, et al. "A Tumorigenic Subpopulation with Stem Cell Properties in Melanomas." *Cancer Research*, 65(20):9328-9337, (Oct. 2005).

Nagai, et al. "A New Sensitive and Specific Combination of CD81/CD56/CD45 Monoclonal Antibodies for Detecting Circulating Neuroblastoma Cells in Peripheral Blood Using Flow Cytometry." *Journal of Pediatric Hematology/Oncology*, 22(1):20-26 (Jan./Feb. 2000).

Bata-Csorgo, et al. "Flow Cytometric Identification of Proliferative Subpopulations within Normal Human Epidermis and the Localization of the Primary Hyperproliferative Population in Psoriasis." *J Exp Med*, 8:1271-1281, (Oct. 1993).

Akashi, et al. "Gene expression of CD24 core polypeptide molecule in normal rat tissues and human tumor cell lines." *Virchows Archives*, 425:399-406, (1994).

Ponti, et al. "Isolation and In vitro Propagation of Tumorigenic Breast Cancer Cells with Stem/Progenitor Cell Properties." *Cancer Research*, 65(13):5506-5511, (Jul. 2005).

Choi, et al. "CNS Recurrence Following CD34b Peripheral Blood Stem Cell Transplantation in Stage 4 Neuroblastoma." *Pediatr Blood Cancer*, 45:68-71, (2005).

International Search Report and Written Opinion of the International Searching Authority for PCT/US06/61204 mailed Apr. 15, 2008.

Goodman & Gilman's: The Pharmacological Basis of Therapeutics, 10th Edition, McGraw-Hill Medical Publishing Division, 2001, pp. 54-56.

International Search Report and The Written Opinion of the International Searching Authority for PCT/US/06/61204 mailed Apr. 15, 2008.

Bowman, et al., "IL-2 Adenovector-Transduced Autologous Tumor Cells Induce Antitumor Immune Responses in Patients with Neuroblastoma," Blood, 1998: 92-1941-1949.

* cited by examiner

STAGE 4 BONE MARROW PRIMARY SPHERES     STAGE 4 TUMOR, PRIMARY SPHERES

STAGE 4 BONE MARROW, PRIMARY SPHERES

STAGE 1 TUMOR

STAGE 1 TUMOR

STAGE 4 BONE MARROW

STAGE 1 TUMOR

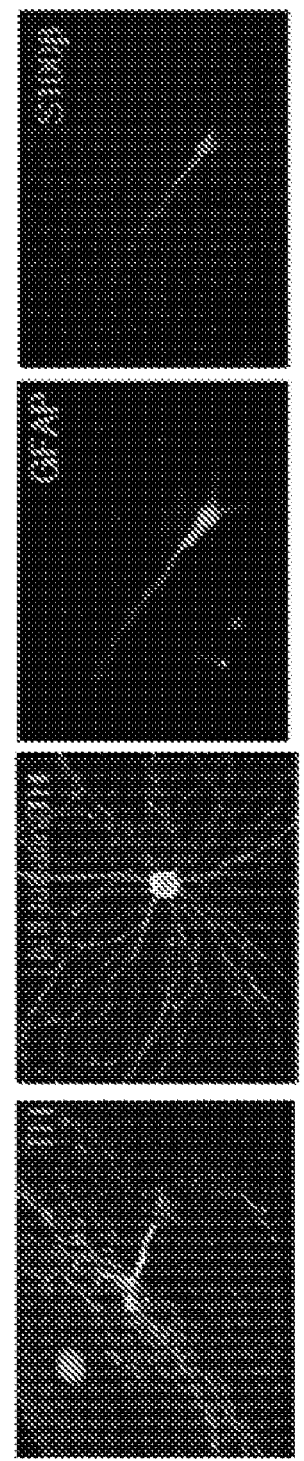
FIG. 3A DIFFERENTIATED CELLS FROM TUMOR SPHERES FROM STAGE 4 BONE MARROW FIG. 3B
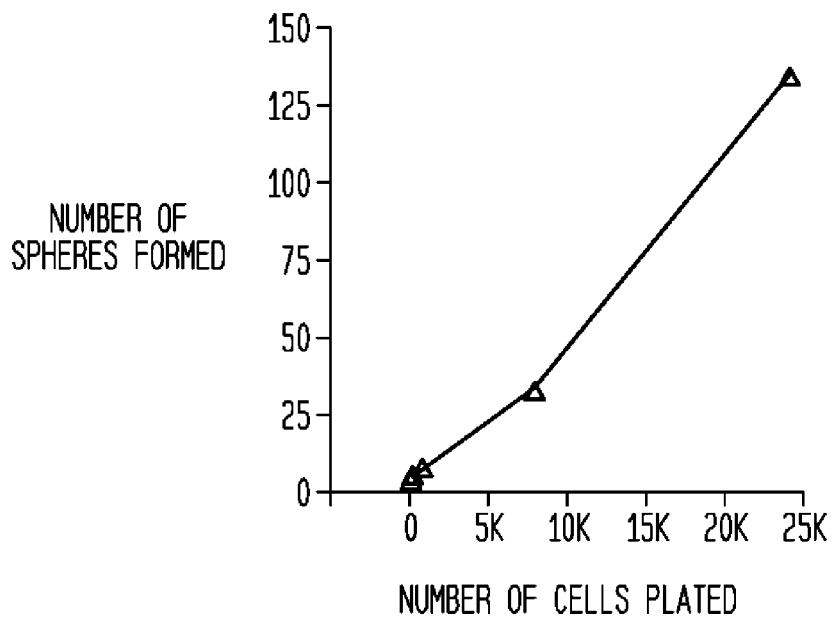
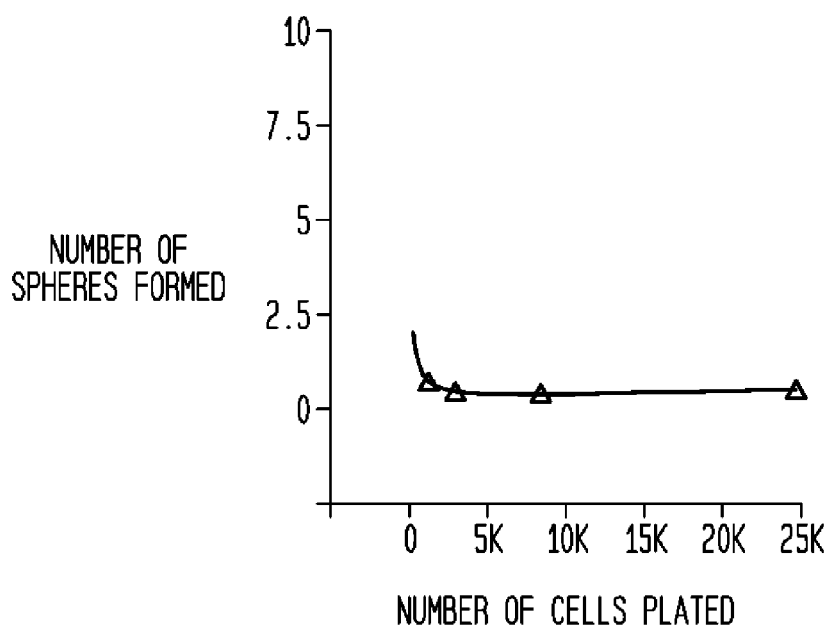

TUMORS ARISING FROM 2.5 x 10³ TUMOR SHERE CELLS FROM STAGE 4 BONE MARROW

SKPs INFECTED WITH GFP ADENOVIRUS

SKPs PROLITERATE, MIGRATE AND DIFFERENTIATE
WHEN TRANSPLANTED IN OVO INTO THE
DEVELOPING CHICK NEURAL CREST

SYMPATHETIC GANGLIA

DORSAL ROOT GANGLIA

SKPs PROLITERATE, MIGRATE AND DIFFERENTIATE
WHEN TRANSPLANTED IN OVO INTO THE
DEVELOPING CHICK NEURAL CREST

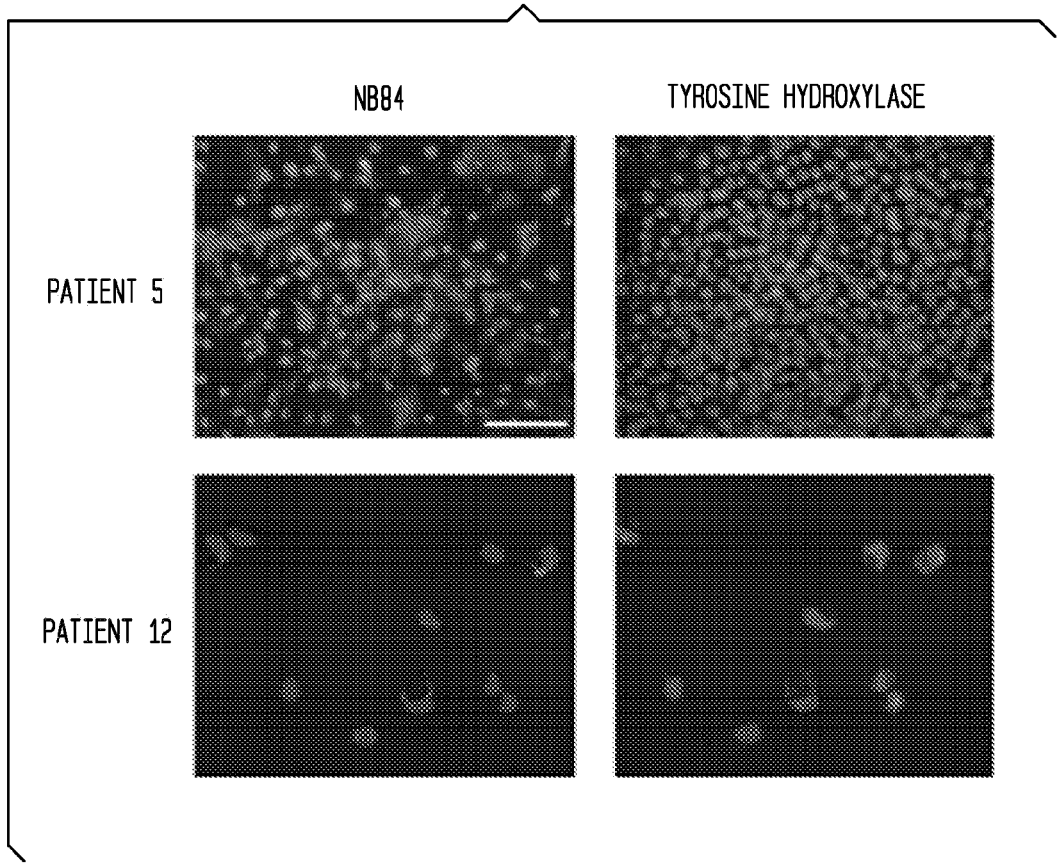

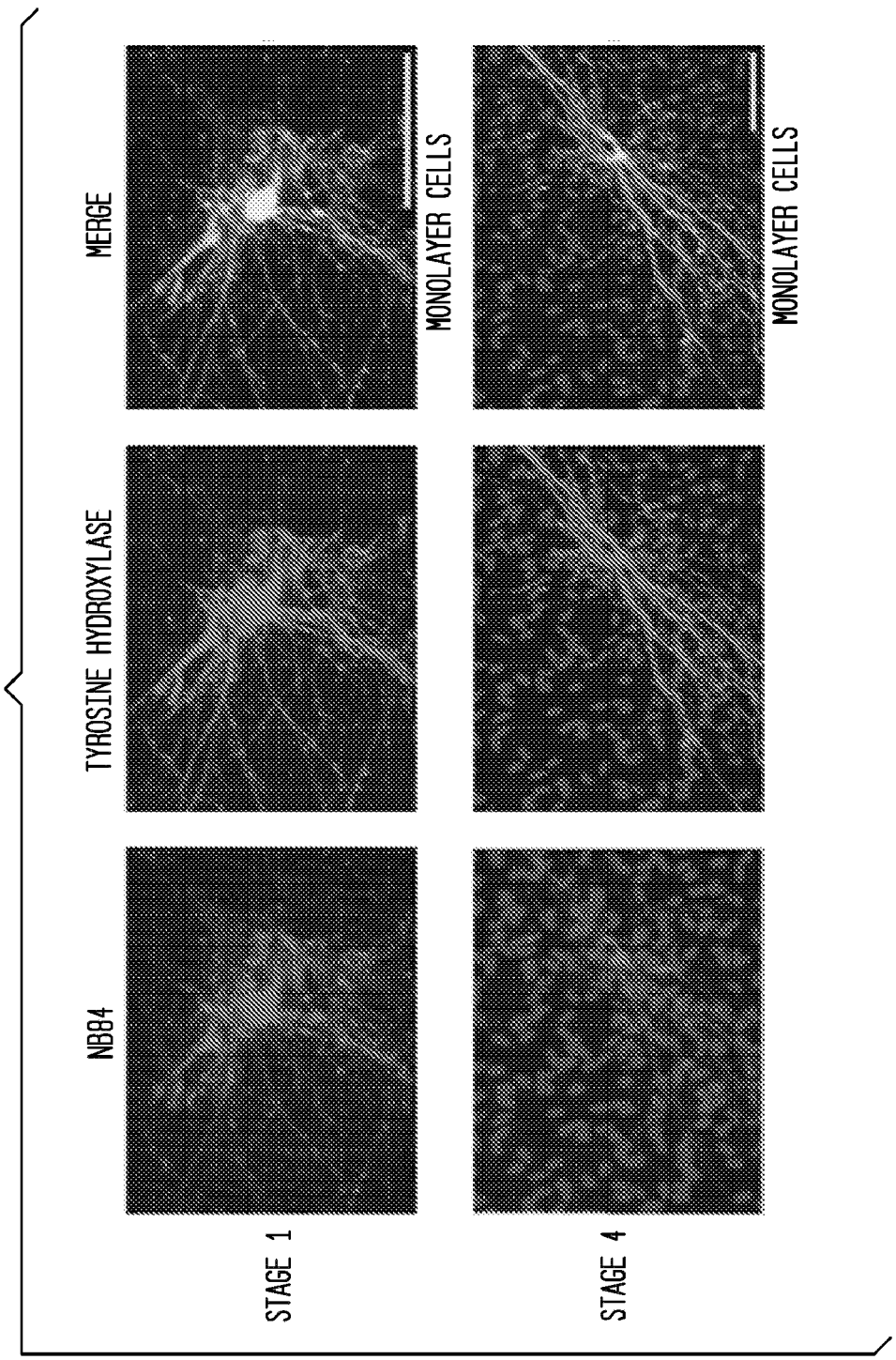

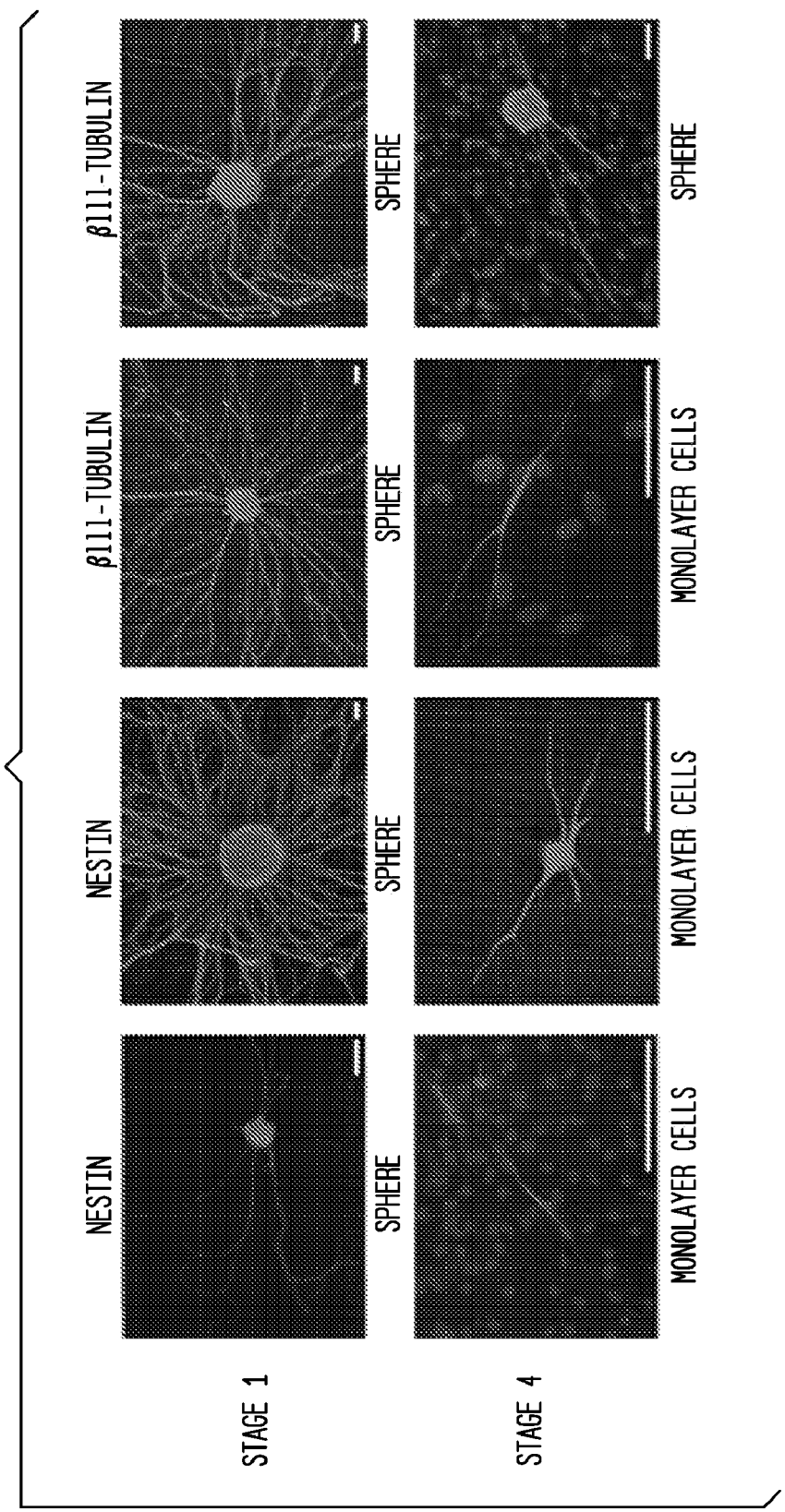

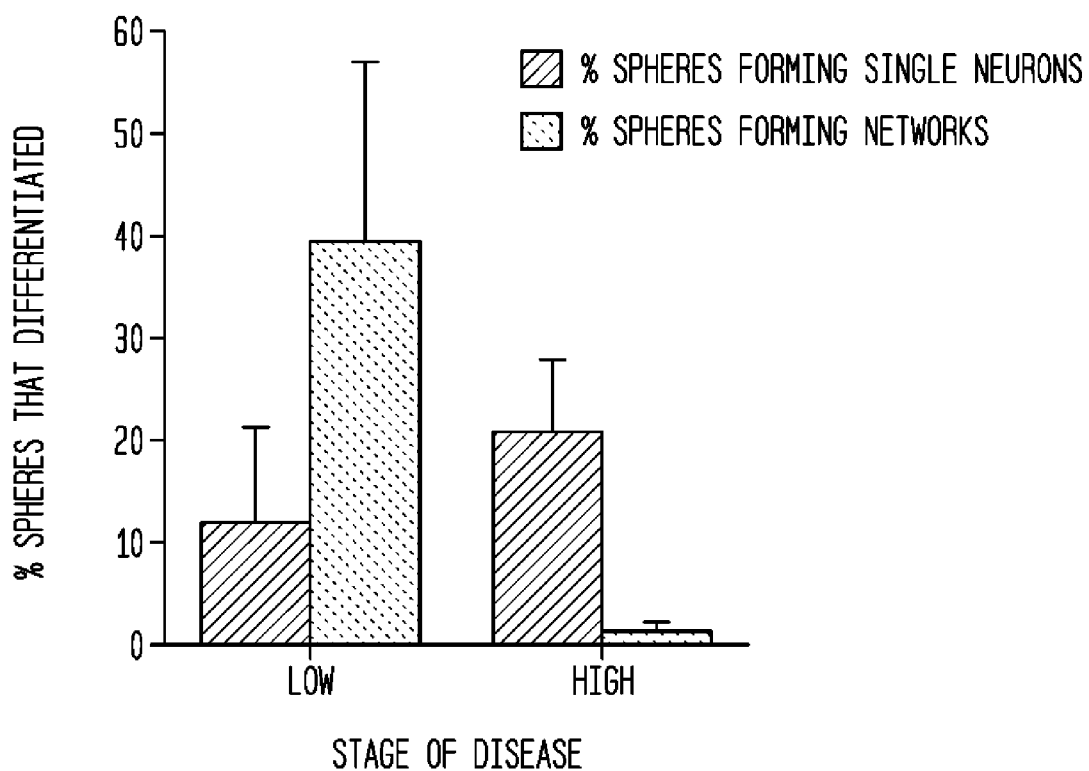

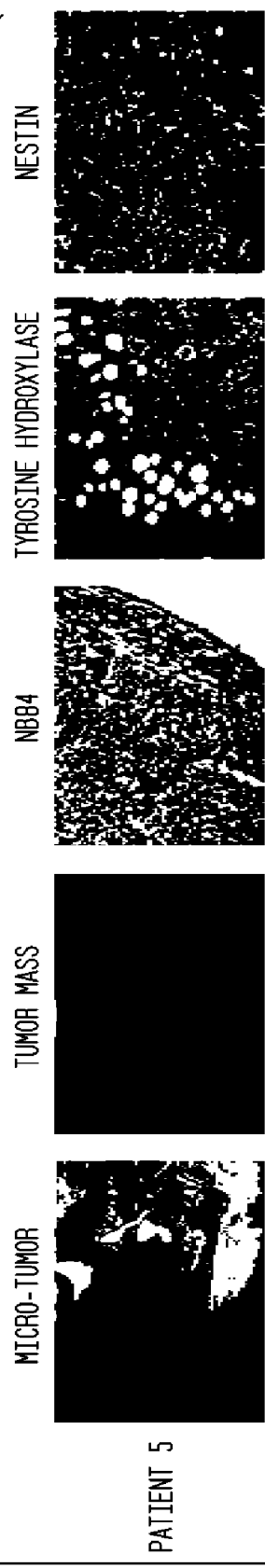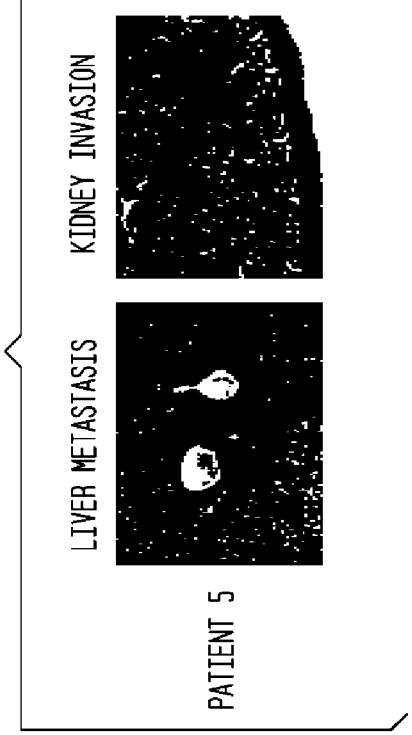
FIG. 8A
FIG. 8B

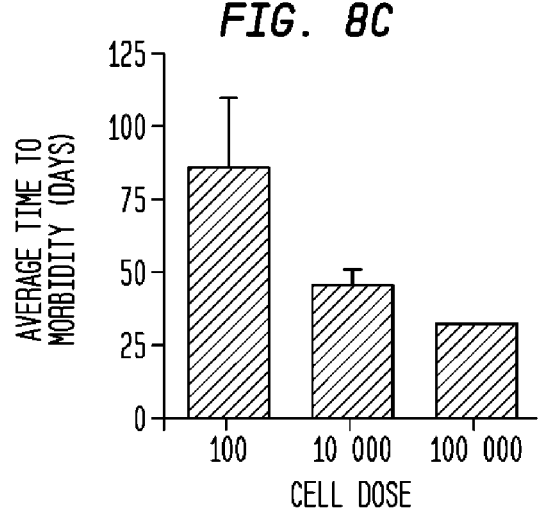
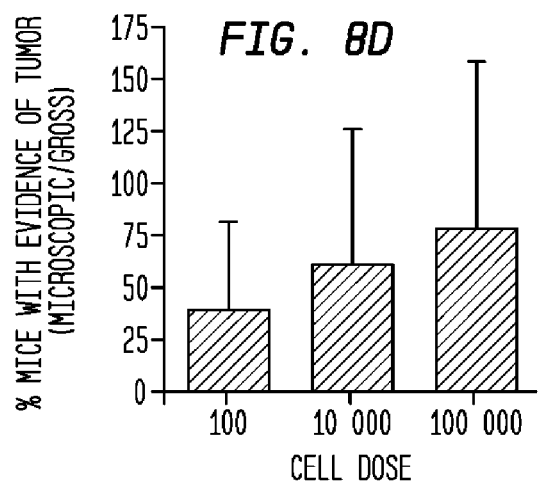
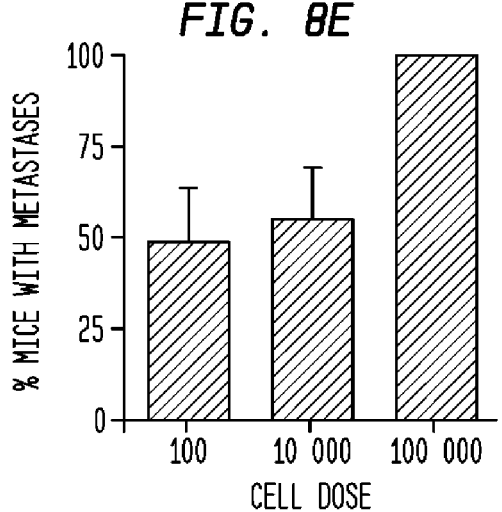

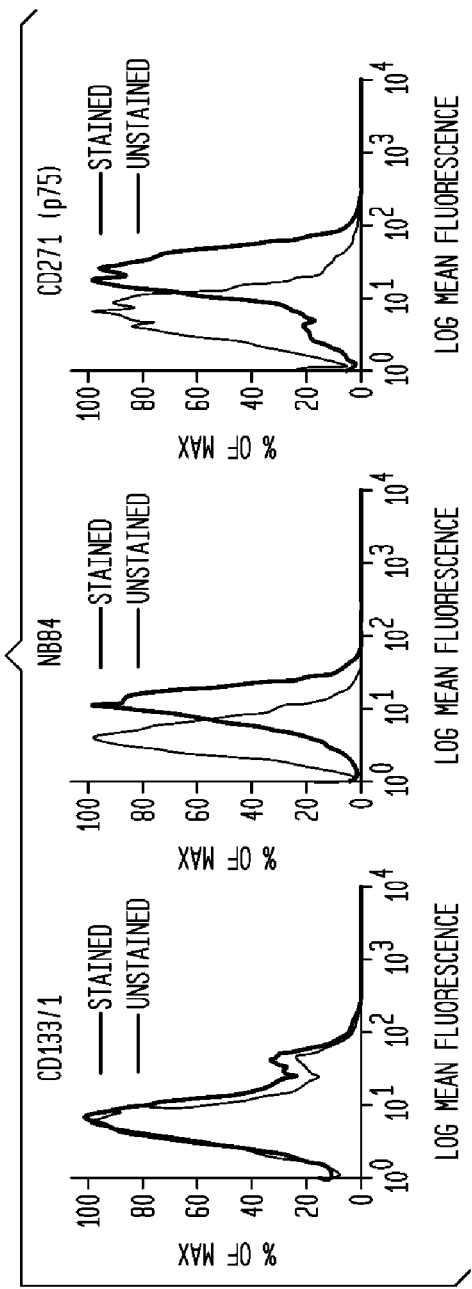
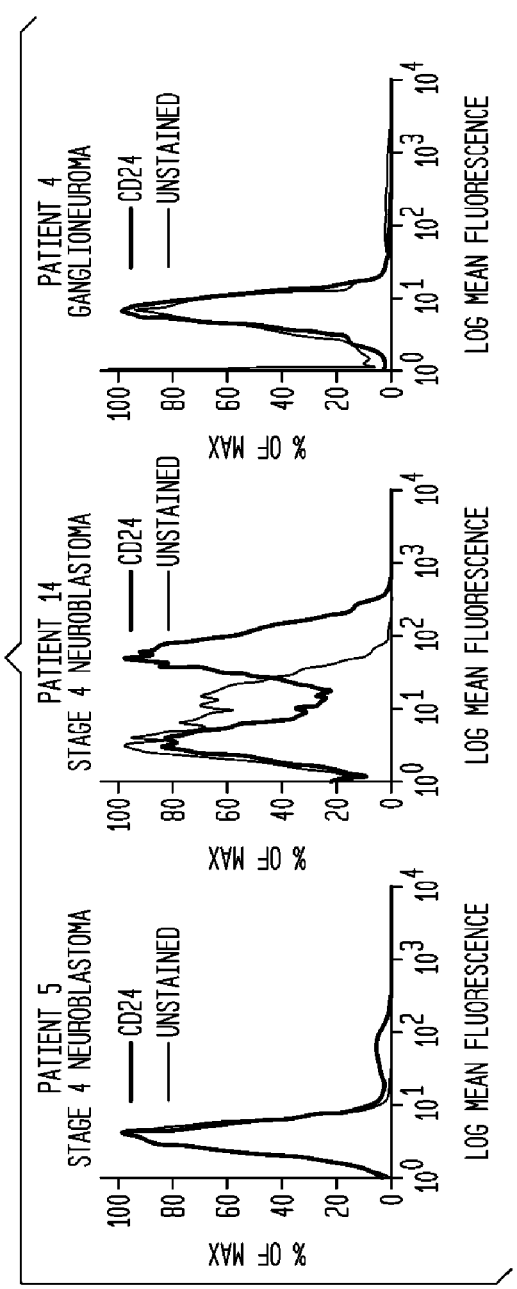
FIG. 9A
FIG. 9B

CD24

PATIENT 5

CD34

PATIENT 5

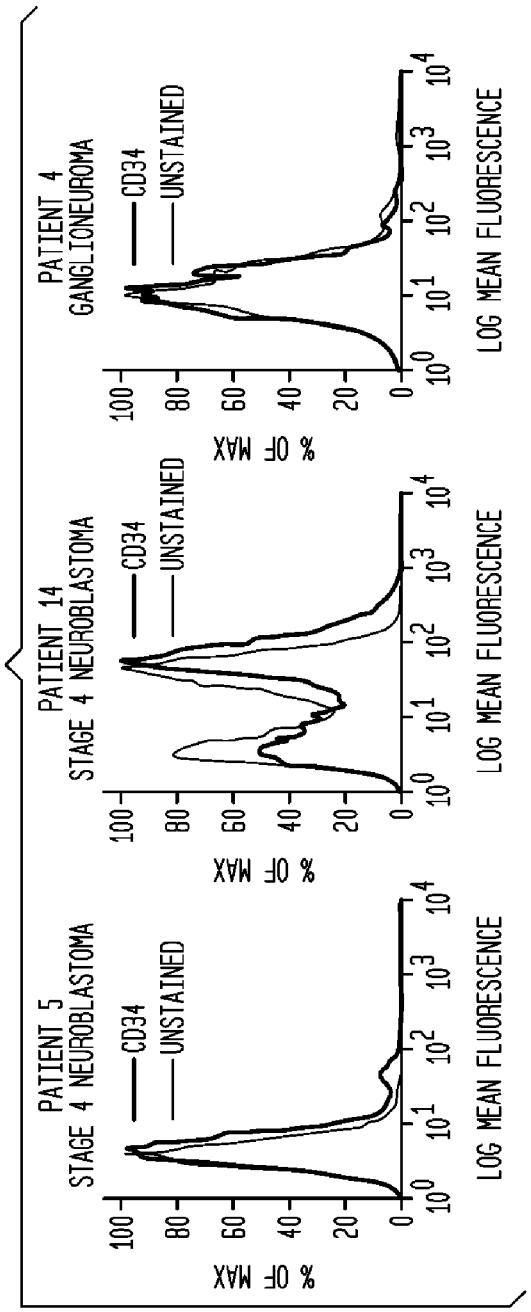
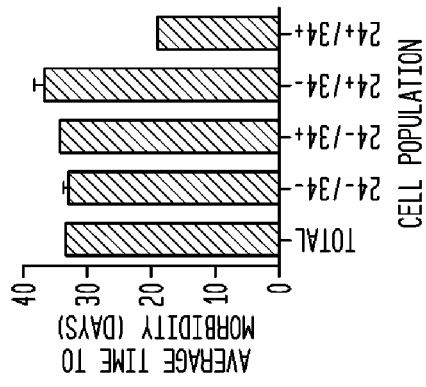
FIG. 9D
FIG. 9F

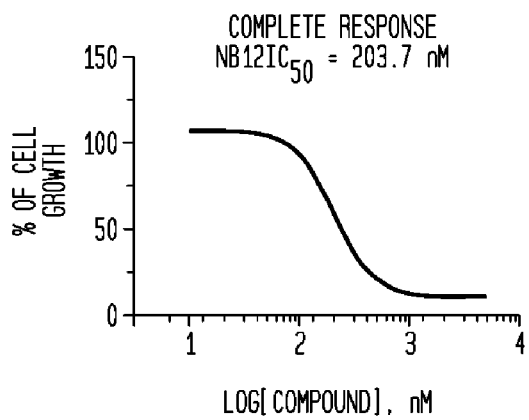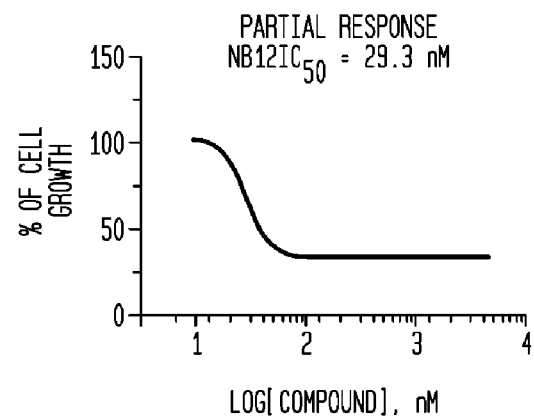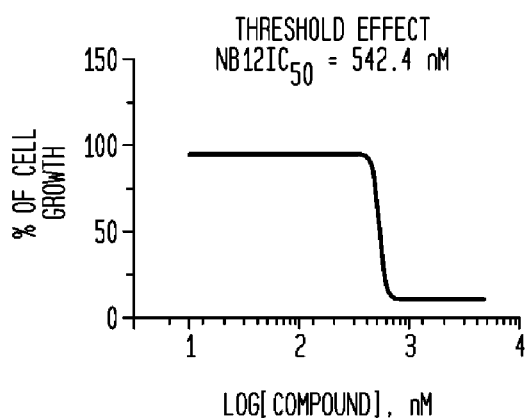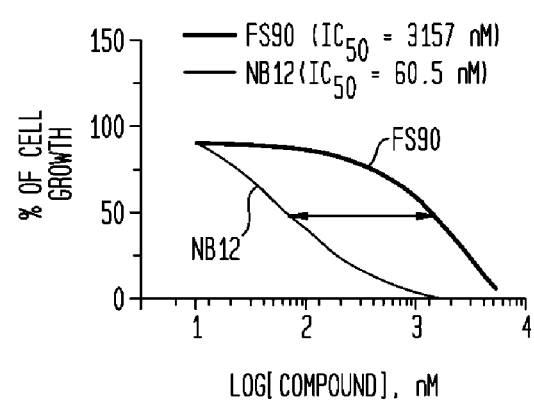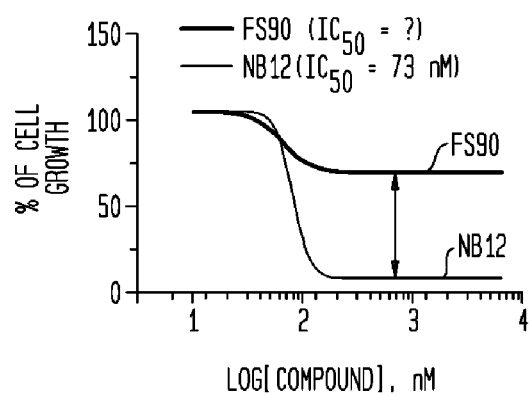

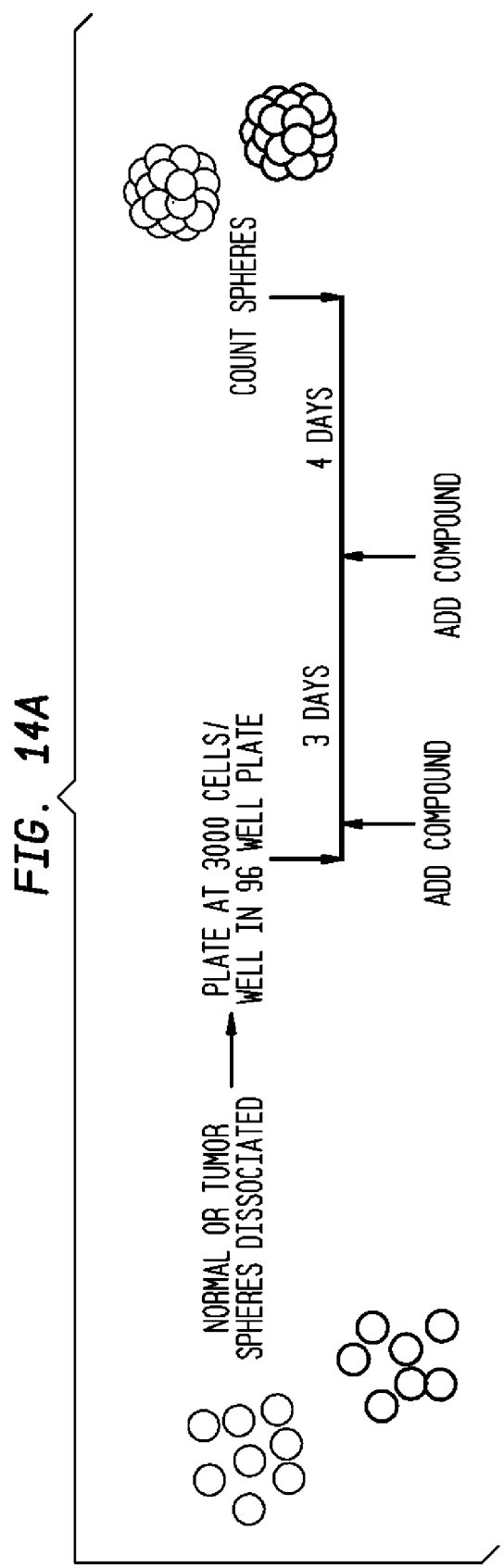

L-LORATIDINE

L-SANGUINARINE CHLORIDE
1795 nM

P-PACLITAXEL
FLOATING POINT ERROR

L-DIHYDROOUABAIN
1540 nM

L-MG 624
848 nM

L-DL-STEAROYLCARNITINE CHLORIDE
2311 nM

P-CAMPTOTHECINE (S.+)
183 nM

P-DEQUALINIUM DICHLORIDE
1365 nM

P-SCOULERINE

L-CHELERYTHRINE CHLORIDE
2553 nM

L-DIPHENYLENEIODONIUM CHLORIDE

P-ANTIMYCIN A
354 nM

P-ETOPOSIDE
693 nM

P-PRIMAQUINE DIPHOSPHATE

L-DEQUALINIUM ANALOG
1112 nM

L-VINCRISTINE SULFATE
61 nM

P-AVERMECTIN B1

L-PODOPHYLLOTOXIN
135 nM

L-VINBLASTINE SULFATE SALT
113 nM

P-AMODIAQUIN DIHYDROCHLORIDE DIHYDRATE
790 nM

P-AZAGUANINE-8
331 nM

P-MYCOPHENOLIC ACID
1745 nM

L-QUINACRINE DIHYDROCHLORIDE
2556 nM

P-COLCHICINE
29 nM

P-DIGOXIN
542 nM

P-STROPHANTHIDIN
563 nM

L-DEQUALINIUM DICHLORIDE
3617 nM

L-IDARUBICIN
203 nM

L-AMMONIUM PYRROLIDINEDITHIOCARBAMATE
886 nM

P-TERFENADINE
3226 nM

P-CLOFAZIMINE
1417 nM

P-PARTHENOLIDE
2261 nM

TOMATIDINE HYDROCHLORIDE

CICLOPIROX OLAMINE

PRENYLETIN

AKLAVINE HYDROCHLORIDE

MECHLORETHAMINE

DIHYDROGAMBOGIC ACID

PYRITHIONE ZINC

MECLIZINE HYDROCHLORIDE

GAMBOGIC ACID

BEPRIDIL HYDROCHLORIDE

IMIDACLOPRIDE

LIMONIN

BETA-PELTATIN

PERIPLOCYMARIN

PERUVOSIDE

OUABAIN

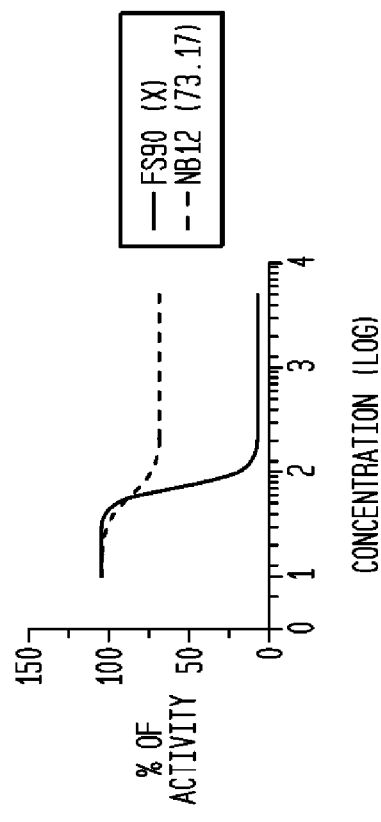
FIG. 16Q CRINAMINE
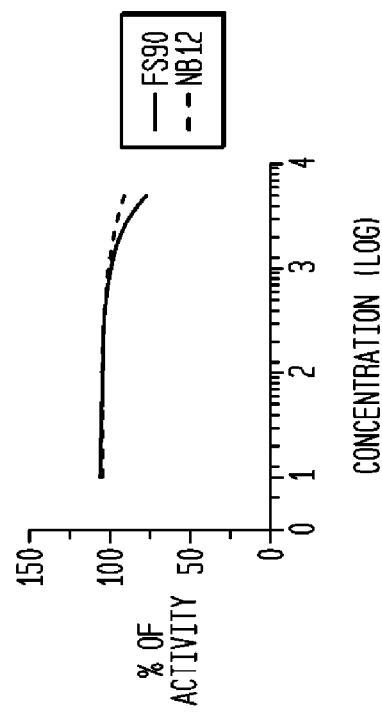
FIG. 16R CONVALLATOXIN
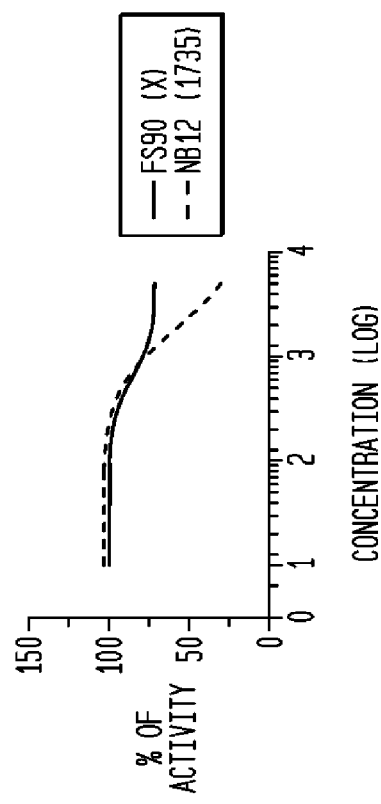
FIG. 16S TOMATINE
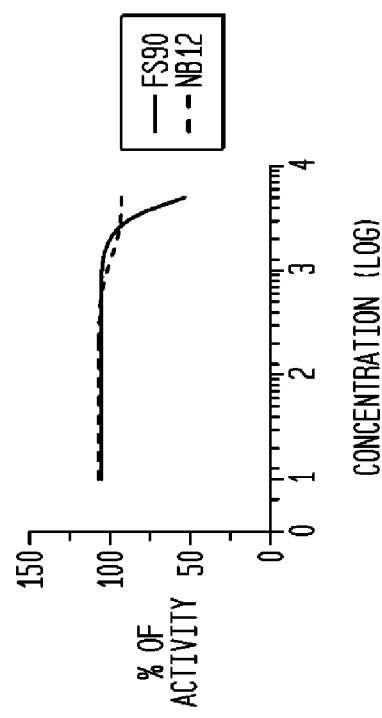
FIG. 16T JUGLONE

CRASSIN ACETATE

CHOLESTAN-3BETA,5ALPHA,
6BETA-TRIOL

ANDROGRAPHOLIDE

ERYSOLIN

MITOXANTHRONE HYDROCHLORIDE

MITOMYCIN C

PARAROSANILINE PAMOATE

ANCITABINE HYDROCHLORIDE

AMSACRINE HYDROCHLORIDE

OXYBENDAZOLE

TENIPOSIDE

CGP-74514A HYDROCHLORIDE

CANCER STEM CELLS AND USES THEREOF

CROSS-REFERENCE TO RELATED APPLICATIONS

This application makes reference to the following provisional U.S. patent application Ser. No. 60/739,337 entitled "Cancer Stem Cells and Uses Thereof", filed Nov. 23, 2005. The entire disclosure and contents of the above application is hereby incorporated by reference.

BACKGROUND

1. Field of the Invention

The present invention relates generally to preparations of stem cells, particularly cancer stem cells derived from neural crest tissue. The invention also relates to methods of isolating cancer stem cells, and various methods for using cancer stem cells in diagnostic, therapeutic and other clinical and non-clinical applications.

2. Related Art

Neuroblastoma (NB) is the most common extracranial solid tumors in children, with poor survival rates in children with metastatic disease. NB is estimated to be responsible for about 15% of cancer-related deaths in children (1, 2). The survival rate for metastatic NB is estimated to be less than 30%. In the majority of these cases, conventional cancer therapies have been ineffective.

Little is reported concerning the precise molecular alterations that give rise to NB, its cell of origin, or why NB cells metastasize and become resistant to chemotherapeutic agents. Unfortunately, genetic mutations that contribute to the origin and progression of 98% of NB cases have not been identified.

One identifiable hallmark of NB is the appearance of proliferating cells with characteristics of neural crest-derived sympathetic neuronal precursors (neuroblasts). NB tumors also frequently contain other neural crest cell types, including neuroendocrine and Schwann cells. Moreover, NB appears in tissues that developmentally derive from the neural crest including sympathoadrenal precursors which differentiate into both sympathetic neurons and adrenal chromaffin cells, the paravertebral and preaortic sympathetic ganglia, and the adrenal gland.

The clinical behavior of NB is unique. Tumors that arise in children under one year of age may spontaneously regress by differentiation or apoptosis, even after arising in or metastasizing to liver and skin. In contrast, NB tumors in children over one-year-old often grow aggressively, disseminate to the bone and bone marrow, and are fatal in the vast majority of cases.

Mass screening of infants showed that NB is much more frequent than previously thought. Many of these tumors regress without clinical diagnosis. Regressing or favorable-prognosis tumors have been reported to express high levels of the TrkA/NGF receptor and display phenotypes of differentiated peripheral neural cells, while malignant or unfavorable-prognosis tumors resemble proliferating sympathoadrenal precursors, often expressing TrkB, amplified MYCN, and many genes involved in neural crest development.

The only reported germline NB predisposition gene is Phox2b, which is mutated in many familial cases of NB, and is required for proper differentiation of sympathetic neurons from neural crest precursors (NCPs) (3,4). In the regressive form of the disease, the precursor cells ultimately differentiate or die, while in older children, these molecular transformations instead result in a population of persistently proliferating and highly migratory transformed neuroblasts.

The concept of tumor-initiating cells (TIC) (also called tumor or cancer stem cells) postulates that only rare cells in tumors are endowed with tumorigenic potential, and was initially developed to explain why (i) most tumors are comprised of both undifferentiated proliferating progenitors and post mitotic differentiated cells, (ii) only a very small fraction of tumor cells form colonies after plating in vitro, and (iii) large numbers of tumor cells are required to seed the growth of a new tumor in mice (4-10).

Dick et al. and others reported that clonally-derived tumor cells of acute myelogenous leukemia (AML) patients could be physically separated into tumorigenic and non-tumorigenic fractions (11, 12). Brain and breast tumors have also been reported to contain a subpopulation of TICs (13, 14). Thus, in solid tumors, a rare tumor cell population may fuel tumor growth and seed metastasis. This hypothesis has major implications for treating cancer patients. For example, many current therapies kill the bulk of proliferating tumor cells, but these cells may not be intrinsically tumorigenic, and in many cases the TICs may escape the effects of the therapeutic agents, leading to tumor relapse. Thus, it is essential to identify and characterize TICs from various tumors in order to develop and target therapies against this critical cell type.

TICs have also been shown to share phenotypic characteristics with stem cells derived from their tissue of origin. For example, for a given tissue, the tissue stem cells and TICs both (i) self-renew, (ii) express common phenotypic markers, (iii) grow in a similar fashion in response to mitogens, and (iv) yield tissue-appropriate progeny (13, 14). However, whereas tissue stem cells generate mature differentiated cell types, differentiation of TICs is generally arrested at the level of one or more tissue progenitor cells resulting in tumors comprising a hierarchy of progenitors and some differentiated progeny (4).

Many pediatric and adult tissues contain resident stem cells (4). It is currently unknown if TICs originate by transformation of tissue stem cells. Observations have been made that oncogenic mutations commonly affect genes required for normal stem cell renewal and differentiation (4). This may be particularly relevant for children's tumors, since developing tissues contain a higher proportion of tissue stem cells than do adult tissues.

Tumor initiating cells from some solid tissue tumors, such as breast and brain tumors, have been described. However, a TIC population from tumor tissue in a patient with NB has not been isolated. One reported observation in some infantile forms of NB (called stage 4S) is that large tumors are frequently found in skin (15). It was previously assumed that skin was a preferred metastatic target for NB. However, a population of TICs from such solid tumor tissue has not yet been reported.

The above and other observations in the field reveal a continuing medical need continues to exist in the art to determine why and in which cell type NB arises, and why some NB tumors spontaneously regress and others are fatal. In addition, new effective drug targets and therapeutics tailored to identifying and treating specific forms and stages of NB are needed.

SUMMARY

The above and other long felt needs in the art are met in the present invention.

The present invention demonstrates the isolation and preparation, as well as uses of, a unique population of tumor initiating cells (TICs) that are characteristic of a condition known as neuroblastoma (NB). It is from these preparations that the various compositions, methods of use, screening methods and therapeutic treatments described herein are primarily provided.

Tumor Initiating Cells/Neuroblastoma Tumor Initiating Cells

In one aspect, the invention provides a composition comprising tumor initiating-cells, and in particular, neuroblastoma tumor initiating cells (NB TICs). Therefore, and in accordance with the first broad aspect of the present invention, there is provided a composition comprising an enriched population of cancer stem cells comprising NB TICs.

An enriched population of NB TICs may be defined in some aspects of the invention as comprising a population of NB TICs that is greater than the concentration of tumor initiating NB cells in a non-concentrated NB tissue preparation, such as in a NB tumor tissue or bone marrow tissue preparation prepared from a tissue obtained from an animal having NB without tissue and/or culture processing.

The enriched preparations of the invention may further be described as a function of the percentage of NB TICs capable of giving rise to a secondary NB sphere in culture contained in the preparation. By way of example, the percentage of a starting NB tumor cell population that is capable of giving rise to secondary NB tumor spheres in a non-enriched preparation of NB tumor tissue is about 0.2% to 2.0%. In an enriched preparation or composition, the percentage of NB tumor cells present in the composition that are capable of giving rise to secondary NB tumor spheres is greater than 2%, and in some embodiments, from 3% to about 18%, of the total cell population contained in the preparation.

The enriched preparations of the invention may further be described as a function of the percentage of NB TICs capable of giving rise to a tumor as compared to the non-enriched population. In an enriched preparation or composition, the percentage of NB tumor cells present in the composition that are capable of giving rise to an NB tumor is 1 in 100, or 1% of the total cell population contained in the preparation.

The NB TIC preparations are further described as capable of initiating the growth of a NB tumor in vivo. The enriched preparations of the invention may further be described as a function of the percentage of NB TICs capable of giving rise to a tumor as compared to the non-enriched population. By way of example, the percentage of a non-enriched population or of an NB established cell line that is capable of giving rise to a tumor is 1 in $2\times10^6$ cells in a commonly used NB mouse xenograph model (28) In an enriched preparation or composition, the percentage of NB tumor cells present in the composition that are capable of giving rise to an NB tumor is 1 in 100, or 1% of the total cell population contained in the preparation.

The NB TIC preparations are further described as capable of initiating the growth of a NB tumor in vivo when enriched for the cell-surface proteins CD24 and CD34. The further enriched preparations of the invention will, when injected into a commonly used neuroblastoma mouse xenograph model (28), cause morbidity at twice the rate of populations of NB TICs not expressing both CD24 and CD34.

The NB TIC preparations may also be further described as comprising postnatal neural crest precursor (NCP) cells. In some embodiments, these NCP cells comprise SKin-derived Precursor (SKP) cells.

In some embodiments, the composition comprises NB TICs derived from human tissue, such as tissue obtained from a tumor or needle biopsy. By way of example, the human tissue may comprise bone marrow tissue or dermis tissue. In some embodiments, the bone marrow tissue or dermis tissue is further described as tissue derived from an infant or child.

The NB TICs of the present invention and compositions and/or preparations that include them are further described as having the following characteristics: isolated directly from patients with neuroblastoma, express cell surface markers that are characteristic of developing neural crest stem cells, are capable of forming tumors, particularly NB tumors, in vivo, are self-renewing, are capable of being passaged at a high frequency, as having chromosomal abnormalities characteristic of NB, and/or are capable of differentiating into cells with the properties of sympathetic neurons.

According to yet another broad aspect of the invention, there is provided a composition comprising an enriched population of cancer stem cells comprising cells from a Stage 1 NB, Stage 2 NB, a Stage 3 NB, a Stage 4 NB, or any combination of a Stage 1, Stage 2, Stage 3, and/or Stage 4 NB.

Method of Preparing, Isolating and Enriching a Population of Neuroblastoma Tumor Initiating Cells.

In another broad aspect of the invention, there is provided a method for providing an enriched population of TICs that more specifically give rise to NB TICs. In some embodiments, the method comprises isolating NB TICs from metastasized bone marrow tissue or from NB tumor tissue, and processing said NB TICs so as to obtain a preparation comprising a 2% or more concentration of NB TICs capable of giving rise to a secondary NB sphere in culture.

By way of example, the percentage of a starting NB tumor cell population that is capable of giving rise to secondary NB tumor spheres in a non-enriched preparation of NB tumor tissue is about 0.2% to 2.0%. In the present method, the enriched preparation or composition comprises a greater than 2% concentration of NB TICs that are capable of giving rise to secondary NB tumor spheres. In some embodiments, the method provides for an enriched preparation that comprises from 3% to about 18% NB TICs that are capable of giving rise to a secondary NB sphere in culture.

In particular embodiments, the invention provides for a method that comprises isolating NB TICs from metastasized bone marrow tissue, rather than from a NB tumor itself.

The NB TICs may be further characterized as capable of giving rise to tumors that are related to the development of the neural crest. By way of example and not limitation, these types of TICs include those that give rise to melanoma, pheochromocytoma, paraganglioma and neurofibromatosis.

In yet another aspect, a screening method is provided for identifying candidate anti-cancer therapeutic agents for cancers arising from development of the neural crest, including melanoma and other tumors containing TICs, such as leukemia, brain, colon and breast. In some embodiments, this screening method employs non-established neural crest cell lines, such as the non-established tumor initiating stem cells described herein.

Screening Method for Neuroblastoma Tumor Initiating Cell Inhibiting Compounds

In another aspect, a screening method is provided comprising a high throughput screen for identifying candidate anti-NB and/or anti-NB TIC therapeutic agents.

In some embodiments, the method comprises screening a chemical compound library of interest for activity in a culture comprising an enriched preparation of NB TICs. Such a chemical library may include the SPECTRUM™ Collection library, the LOPAC™ Collection library, the PRESTWICK CHEMICAL LIBRARY® and the MAYBRIDGE® Collection library (each are libraries of compounds for screening).

In some embodiments, the method may be used to screen for a therapeutic agent custom tailored to a specific patient. In some embodiments, the method in this application would comprise preparing an autogenous culture of NB TICs harvested from an identified patient being screened, and used according to the defined method herein to identify candidate therapeutic agents anticipated to be effective against the particular population of NB of the identified patient. In this manner, potential therapeutic agents may be identified that are without inhibitory or other untoward and/or undesirable effects on normal cell populations of a patient, such as to a patient's normal stem cell population or immune system.

In yet another aspect, a diagnostic screening method is provided using the isolated tumor initiating stem cells of the invention. In some embodiments, the method employs the use of NB TIC specific prognostic markers to identify the absence or presence of NB, and in some cases the stage of NB, in a biological sample obtained from an animal, such as a human. In this manner, the invention also provides for methods of screening and identifying particular stages of disease progression in NB stage 1, 2, 3 and 4 diseases, and to identify potential therapeutic agents that may be effective in both identification and treatment.

Nucleic Assay Microarray System

In yet another aspect, a nucleic assay microarray system, such as a cDNA microarray method, is provided to identify novel markers and drug targets for NB stem cells.

Methods of Inhibiting Neuroblastoma Tumor initiating Cells/ Methods of Treating and/or Inhibiting Neuroblastoma in an Animal In yet another aspect, the invention provides methods for inhibiting NB TICs. In some embodiments, the method comprises administering an effective amount of a composition comprising a NB TIC-inhibiting ingredient. In some embodiments, the NB TIC inhibiting ingredient comprises one or more active ingredients comprising:

2.3-Dimethoxy-1.4-naphthoquinone,
Aklavine Hydrochloride,
Amodiaquin dihydrochloride dehydrate;
Amsacrine Hydrochloride;
Azaguanine-8;
beta-peltatin;
Camptothecine (S.+);
CGP-74514A hydrochloride;
Chelerythrine chloride;
Cholestan-3beta.5alpha.6beta-Triol;
Ciclopirox Olamine;
Clofazimine;
Colchicine;
Convallatoxin;
Crassin Acetate;
Crinamine;
Dequalinium analog. C-14 linker;
Dequalinium dichloride;
Digitoxin;
Digoxigenin;
Dihydrogambogic acid;
Dihydroouabain;
Erysolin;
Gambogic acid;
Mechlorethamine;
Meclizine hydrochloride;
MG 624;
Mitoxanthrone Hydrochloride;
Ouabain;
Oxybendazole;
Paclitaxel;
Parthenolide;
Patulin;
Periplocymarin;
Peruvoside;
Primaquine diphosphate;
Quinacrine dihydrochloride;
Sanguinarine chloride; or
Tomatine.

In some embodiments, the effective amount of the NB TIC-inhibiting ingredient is an amount effective to arrest the growth of and/or kill NB TICs, or effective to induce differentiation of said cells to cell types that no longer proliferate. In other embodiments, the method may further comprise administering a composition further comprising ancitabine hydrochloride, doxorubicin hydrochloride, etoposide, vincristine sulfate, or a combination thereof.

In some embodiments, the compositions may further include a pharmaceutically acceptable carrier solution.

In yet other embodiments, the NB TICs are in an animal having NB In some embodiments, the animal is a human. In some embodiments, the human is 12 years of age or younger. That is, it is anticipated that the invention is particularly useful in the treatment of children afflicted with NB, and will have a profound effect on reducing the high rate of mortality in this population of NB patients.

The method may be further described as administering a composition that has a reduced non-NB TIC cytotoxicity. It is expected that the methods and compositions of the present invention will provide fewer and/or less pronounce undesirable side affect in the treatment of a patient as a result. In some embodiments, the composition employed in the method is essentially free of non-NB TIC-inhibiting activity.

Kits

In yet another aspect, the invention provides a kit for the testing and/or screening of a patient of interest's NB TICs. In this manner, a sample of biological tissue enriched for a population of NB TICs from a patient of interest may be used to screen and/or identify a specific anti-NB TIC active agent or agents that are the most potent and/or active against a specific patient's NB TIC population.

In some embodiments, the kit would comprise an assay plate that includes a plurality of wells, each well of said assay plate being suitable for containing a pharmacologically active agent of interest, such as a potentially anti-NB TIC pharmacologically active agent. By way of example, the assay plate may comprise 40, 50, 60, 70, 80, 90 100 or more wells. In some embodiments, the assay plat will include 96 wells, such as is customary in assay plates. As part of the kit described herein, 5, 10, 20, 25, 30, or 40 of the wells may include a different anti-NB TIC compound, such as a volume of one or more of each of the compounds listed below:

2.3-Dimethoxy-1.4-naphthoquinone,
Aklavine Hydrochloride,
Amodiaquin dihydrochloride dehydrate;
Amsacrine Hydrochloride;
Azaguanine-8;
beta-peltatin;
Camptothecine (S.+);
CGP-74514A hydrochloride;
Chelerythrine chloride;
Cholestan-3beta.5alpha.6beta-Triol;
Ciclopirox Olamine;
Clofazimine;
Colchicine;

Convallatoxin;
Crassin Acetate;
Crinamine;
Dequalinium analog. C-14 linker;
Dequalinium dichloride;
Digitoxin;
Digoxigenin;
Dihydrogambogic acid;
Dihydroouabain;
Erysolin;
Gambogic acid;
Mechlorethamine;
Meclizine hydrochloride;
MG 624;
Mitoxanthrone Hydrochloride;
Ouabain;
Oxybendazole;
Oxybendazole;
Paclitaxel;
Parthenolide;
Patulin;
Periplocymarin;
Peruvoside;
Primaquine diphosphate;
Quinacrine dihydrochloride;
Sanguinarine chloride; or
Tomatine.

In addition, and in some embodiments of the kit, at least one or more of the assay wells will include a volume of a pharmacologically active agent that is known and/or is in use as an anti-NB agent, such as ancitabine hydrochloride, doxorubicin hydrochloride, etoposide, or vincristine sulfate. In this manner, a positive control is provided in the assay plate for comparative purposes.

The following abbreviations are used throughout the description of the present invention:
AdGFP—green fluorescent protein expressing adenovirus;
AML—acute lymphoblastic leukemia;
ARF—ADP-ribosylation factor;
BDNF—brain-derived neurotrophic factor;
bHLH—basic HLH;
BrdU—bromodeoxyuridine;
cDNA—copy deoxyribonucleic acid;
CNPase—2'3'-cyclic nucleotide 3'-phosphodiesterase;
CNS—central nervous system;
DRG—dorsal root ganglia;
DNA—deoxyribonucleic acid;
ΔNp73—N-terminally truncated p73 (lacking the trans-activation domain)
EGF—epidermal growth factor;
FACS—fluorescence-activated cell sorting;
FGF—basic fibroblast growth factor 2;
GalC—galactosyl ceramide;
GD2—a disialoganglioside expressed on tumors of neuroectodermal origin;
GFAP—glial fibrillary acidic protein;
GFP—green fluorescent protein;
GTG-banding—G banding using trypsin and Giemsa;
HLH—helix-loop-helix;
H&E—hematoxylin and eosin
HSC—human stem cell;
LOH—loss of heterozygosity;
NB—neuroblastoma;
NCP—neural crest sympathoadrenal precursors;
NFM—neurofilament M;
NGF—nerve growth factor;
NOD/SKID—nonobese diabetic/severe combined immunodeficient;
NT—neural tube;
Rb—retinoblastoma;
RNA—ribonucleic acid;
RT-PCR—reverse transcription-polymerase chain reaction;
SCG—sympathetic superior cervical ganglia;
shRNA—short hairpin RNA;
siRNA—small interfering ribonucleic acid;
SKPs—skin-derived precursor cells;
SNP—single nucleotide polymorphisms;
TH—tyrosine hydroxylase;
TIC—tumor initiating cell;
TUNEL—terminal deoxynucleotidyltransferase-mediated dUTP nick end labeling;
YFP—yellowish-green fluorescent protein.

In yet another aspect, the invention provides a kit for the testing and/or screening of a patient of interest's tumor-initiating cells (TICs) from tumors such as melanoma, leukemia, brain, breast, and colon. In this manner, a sample of biological tissue enriched for a population of TICs from a patient of interest may be used to screen and/or identify a specific anti-TIC active agent or agents that are the most potent and/or active against a specific patient's TIC population, using the above compounds.

BRIEF DESCRIPTION OF THE DRAWINGS

The invention will be described in conjunction with the accompanying drawings, in which:

FIG. 3A-3C, according to some aspects of the invention, demonstrate (3A) that NB tumor spheres generate sympathetic neuron and Schwann-like cells under neurogenic conditions. Primary spheres were plated on laminin/lysine coated slides in the absence of growth factors, and after 14 days, immunostained for the neuronal markers TH or βIII-tubulin or the glial markers GFAP or s100β. (3B) Secondary sphere formation from dissociated NB bone marrow aggregates. The number of spheres formed is proportional to the number of cells plated, and the percent of cells forming spheres does not vary with the number of plated cells. (3C) NB tumor spheres generate tumors when injected subcutaneously in NOD/SCID mice. Tumors were excised, sectioned, and immunostained for the NB marker NB84 (arrows point to NB84-positive cells).

FIG. 6A-6D, according to some aspects of the invention, illustrates that high-grade NB tumor sphere cells exhibited increased self-renewal capacity and could be passaged multiple times when compared to low-grade tumors and SKPs (negative) controls. Serial dilutions of single cells from tumor spheres were plated into semi-solid methylcellulose and the percentage of single cells capable of forming a secondary sphere was calculated. This process was repeated until the sphere-forming cells were depleted. (6A) Average number of passages until self-renewal ability was depleted (+SEM) for ganglioneuroma tumors and low-grade NB tumor spheres (low) and high-grade NB tumor spheres (high). The number of spheres that formed was proportional to the number of cells plated and did not alter with passaging (6B) and growth curves indicated logarithmic growth of cultured primary tumors with time (+SEM) (6C). High-grade tumor spheres (patient 5) and adherent cells (patient 12) retained their immunophenotype for NB84 and TH with passaging (6D), scale represents 50 µm.

FIG. 7A-7C, according to some aspects of the invention, demonstrates that high-grade NB tumor sphere cells exhibited limited differentiation potential when compared to tumor spheres from low-grade NB tumors. Tumor spheres were differentiated under neurogenic conditions and immunostained with a variety of neuronal markers. Neuronal networks formed from both low and high-grade tumor spheres and retained expression of the clinical NB markers NB84 and TH (7A). Spheres from low-grade tumors differentiated into large nestin positive or βIII-tubulin positive neuronal networks (B, upper panel). High-grade NB tumor samples formed nestin positive and βIII-tubulin positive neurons and fewer neuronal networks (7B, lower panel). Scale represents 100 µm. Similar proportions of tumor spheres from both low and high-grade NB tumors formed single neurons upon differentiation whereas only low-grade NB tumor spheres were able to form complex neuronal networks upon differentiation (+SEM) (7C).

FIG. 8A-8E, according to some aspects of the invention, demonstrates that tumor spheres from a high-grade NB bone marrow aspirate (patient 5) were dissociated and injected orthotopically into the adrenal fat pads of SCID/Beige mice. (8A) H&E staining showing as few as 100 unselected cells injected orthotopically formed micro-tumors 3 weeks after injection, whereas $10^4$ cells formed large tumor masses in the same time period. Tumors stained positive immunohistochemically for the clinical NB markers NB84 and TH and for the neural progenitor cell marker nestin (arrow heads). (8B) H&E staining showing cells that had metastasized to the liver (left) and invaded the surrounding kidney (right). The time to morbidity decreased with increasing number of cells injected (8C) and the proportion of animals exhibiting tumors, either microscopic or gross (8D), and distant metastases (8E) increased with increasing cell dose. Error bars represent SEM.

FIG. 9A-9E, according to some aspects of the invention, provides a flow cytometry analysis of high-grade NB TICs. Cells were negative for the brain TIC marker CD133/1 (9A) and highly positive for the clinical NB marker NB84 (A) and CD271/p75 (9B). A small fraction of TICs stained positive for the metastatic marker $CD24^+$ (9B) in two independent high-grade NB tumor sphere populations (patients 5 and 14) and was not expressed by ganglioneuroma (patient 4) tumor spheres. Small numbers of brightly positive $CD24^+$ cells were observed in NB tumor spheres by immunocytochemistry (9C). Similarly, a small fraction of TICs stained positive for the progenitor cell marker $CD34^+$ (9D) in two independent high-grade NB tumor sphere populations (patients 5 and 14) and was not expressed by ganglioneuroma (patient 4) tumor spheres. Small numbers of brightly positive $CD34^+$ cells were observed in NB tumor spheres by immunocytochemistry (9E). The $CD24^+/CD34^+$ cell fraction from high-grade NB tumor spheres reduced the time to morbidity when injected orthotopically into immuno-compromised mice (+SEM) (9F), enriching the tumor-forming potential of these cells.

FIG. 13A-13E, according to one embodiment of the invention, presents the $IC_{50}$ values that were determined for the 64 selected candidate compounds. Compounds were chosen for further testing based on differential cell type selectivity, mechanism of action, and pharmacological interest. Tumor-initiating cells and normal cells were treated with 10 serial dilutions of compounds (5 μM to 9 nM). Representative graphs are shown in FIG. 13A (Complete Response), 13B (Partial Response), and 13C (Threshold Effect). Compounds that affected the tumor-initiating cells at a much lower dose than normal cells (13D graph, left) or compounds that had a greater effect on the tumor-initiating cells than normal cells (13E, right graph), were selected for secondary in vitro screens in addition to those compounds that only affected tumor-initiating cells. (FS90=normal cells; NB12=tumor-initiating cells).

FIG. 14A-14C, according to one embodiment of the invention, presents the results from secondary screens of the candidate compounds. Compounds of interest are being tested against additional normal primary cultures (FS89, FS105), a stage IV neuroblastoma primary culture (NB25), and a neuroblastoma cell line (KCNR) using a sphere formation assay. 14A presents a flow diagram of the secondary in vitro screen. The candidate compound is added at 0 days and at 3 days. Spheres are counted at 7 days. FIG. 14B presents a dose response curve of various cell lines (FS89, FS90, FS105, NB12, NB25 and KCNR) to amsacrine. FIG. 14C presents a dose response curve of various cell lines (FS89, FS90, FS105, NB12, NB25 and KCNR) to MG624.

DETAILED DESCRIPTION

Figure 1A:
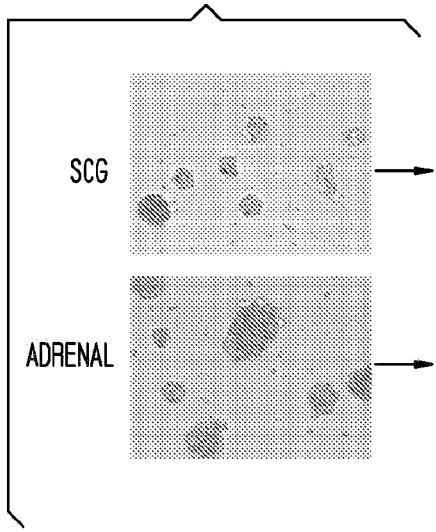
FIGS. 1A-1C, according to one embodiment of the invention, relates to the demonstration of the presence of SKP-like precursors in neonatal mouse adrenal gland and sympathetic ganglia. (1A) Phase illumination of spheres of proliferating cells obtained from neonatal adrenal gland and sympathetic superior cervical ganglia (SCG). (1B) Double-label immunocytochemical analysis of spheres demonstrated that they co express the SKP markers, nestin and fibronection. (1C) Double-label analysis of differentiated adrenal gland spheres demonstrated that they gave rise to morphologically complex cells with the characteristics of sympathetic neurons, such as co expression of neuron-specific βIII-tubulin and neurofilament M (NFM).
Figure 1B:
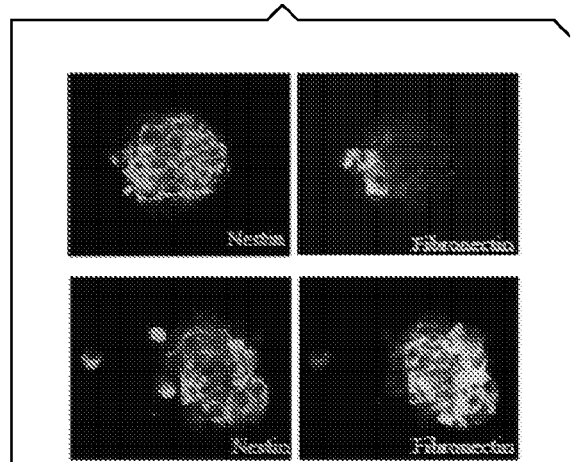

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, "a", "an" and "the" include reference to the plural unless the context as herein presented clearly indicates otherwise.

For purposes of the present invention, the term "active agent" is defined as a chemical entity, group of chemical entities or compound that is capable of providing an affect on NB TICs or NB cells in vitro or in vivo. The affect of the active agent may be a reduction in cytotoxicity relative to the level of cytotoxicity demonstrated in the absence of the active agent under similar conditions, or a cytostatic affect on NB or on NB TICs that results in a reduced rate of NB or NB TIC proliferation and/or growth, or a reduction of the rate or occurrence of differentiation into NB cell types, precursors, or any other cell type that is related to the progression of a NB pathology, or to an increase in the inducement of the differentiation of NB TICs into cell types (for example, neurons) that no longer proliferate (for example, retinoic acid is a common differentiation therapy for neuroblastoma that is used as an adjunct therapy after removal of a tumor, differentiation therapy).

For purposes of the present invention, the term, "effective amount" is defined as an amount of a compound that will inhibit and/or reduce NB TIC survival, proliferation, or that will promote the differentiation of NB TICs into benign cell types.

For purposes of the present invention, the term "enriched" is defined as containing a higher percentage of a particular cell type, such as a cancer stem cell, than is typically present in a native, non-enriched preparation. For example, as used in the definition of the present invention, an "enriched" preparation may be defined as a function of the percentage of tumor initiating cells capable of giving rise to tumor cells in a preparation. An enriched preparation of neuroblastoma tumor initiating cells comprises a greater percentage of neuroblastoma tumor initiating cells capable of giving rise to secondary neuroblastoma spheres compared to a non-enriched preparation. In some embodiments, an enriched preparation of neuroblastoma tumor cells may be described as comprising about 2% or greater, or about 3% to about 18% of the total cell population contained in a preparation. By way of comparison, a non-enriched preparation of neuroblastoma cells would include only about 0.2% to about 2.0% or less neuroblastoma tumor cells that are capable of giving rise to a secondary neuroblastoma sphere. In some embodiments, the enriched preparations comprise a 100-fold, 200-fold, 500-fold, 1,000-fold, or up to a 2,000-fold or 10,000-fold to 20,000-fold enriched preparation of neuroblastoma cells capable of giving rise to secondary neuroblastoma spheres. Since $2 \times 10^6$ cells from established NB cell lines are typically required to form tumors using the protocols described herein, an approximately 20,000-fold enrichment in tumor initiating cells is provided.

For purposes of the present invention, the term "neuroblastoma tumor initiating cell" (NB TIC) is defined as a cell that is capable of giving rise to NB or a tumor cell that is identifiable with a condition of NB, such as a tumor cell that may be identified to have particular identifiable cell surface markers associated with NB (such as NB84, CD44, TrkA, GD2, CD24, CD34, p75NTR, and/or versican) and/or is without cell surface markers that are characteristic of tumor cells that are not from NB (such as CD133, TrkB, and/or CD31). For purposes of the present invention, the term "neuroblastoma tumor-initiating cell inhibiting activity" is defined as an activity for affecting NB TIC survival, proliferation, or that promotes cell differentiation into benign cell types.

EXAMPLES

Example 1

Isolation and Characterization of Tumor Initiating Cells (TICs) in Neuroblastoma Tissue The present example demonstrates the utility of the present invention for providing an enriched preparation of TICs, particularity NB TICs, at a high concentration.

TICs comprise a relatively rare cell population within tumors. For example, brain tumors contain 0.3% to 25% TICs, depending on tumor grade (13, 14). The present example demonstrates the utility of the present invention for providing a highly enriched preparation of specific TICs that are derived from bone tissue, particularly bone tissue from a patient having been diagnosed with NB. The bone marrow employed to provide these enriched preparations of NB TICs had metastasized.

Materials and Methods

Neonatal adrenal gland and SCG were dissociated and cultured under SKP conditions.

Fourteen (14) neuroblastoma (NB) samples including 9 unfavorable prognosis (stages 3 and 4) and 5 favorable-prognosis tumors (ganglioneuroma or benign NB, and stages 1, 2, and 4S) were obtained. Samples were obtained from both tumor tissue and bone marrow metastases that were diagnosed cytomorphologically as clumps of neuroblasts.

NB TICs were isolated from bone marrow aspirates, since (a) they are a hallmark of the highest grade NB (20), (b) it is an accessible source obtained at serial time points before and after chemotherapy, (c) bone marrow contains no resident NCPs (16), and (d) bone marrow from NB patients is tumorigenic when injected into NOD/SCID mice.

The dissociated tumor or bone marrow cell clumps were cultured in human SKP conditions. Human SKP conditions in a culture using uncoated flasks containing defined medium, EGF and FGF (16, 18).

Figure 2A:
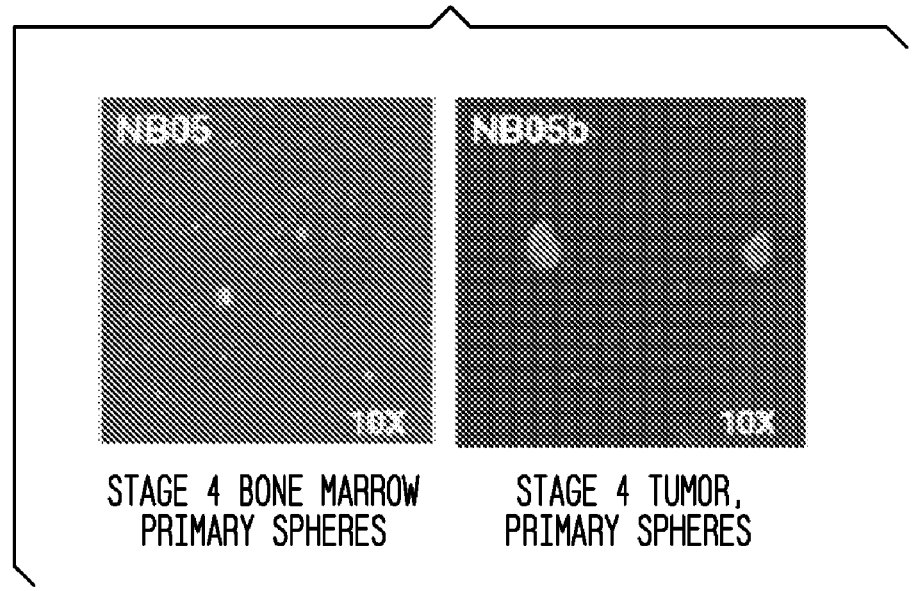
FIGS. 2A-2F, according to some aspects of the invention, illustrate tumor spheres from various stages of NB. They contain a cell that proliferates and self-renews under SKP conditions and expresses NB and SKPs markers. (2A) Photomicrographs of human NB tumor spheres generated from bone marrow (left) and tumor (right) from the same stage 4 patient. (2B-2F). Primary spheres from bone marrow aggregates or tumors were immunostained for the NB markers NB84 (2B, Left panel, lighter regions) and tyrosine hydroxylase (TH) (2B, Right panel, lighter regions) and the SKPs markers nestin (2C, lighter regions), vimentin (2D, lighter regions), fibronectin (2E, lighter regions), and versican (2F, lighter regions).
Figure 2B:
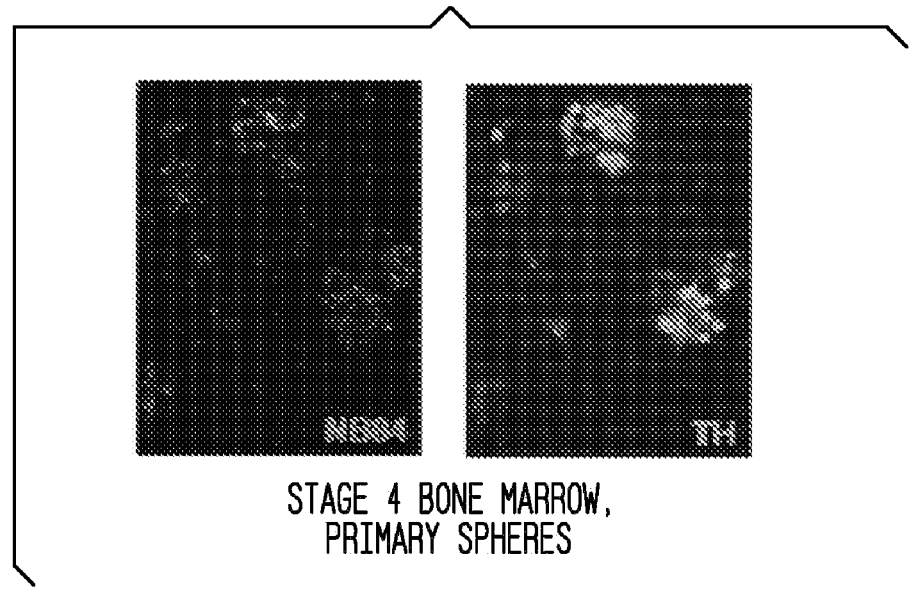
Figure 2C:
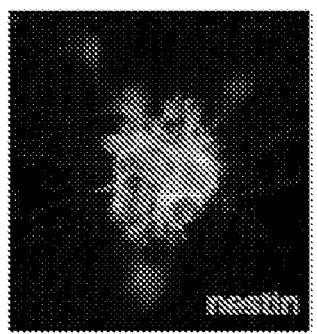
Figure 2D:
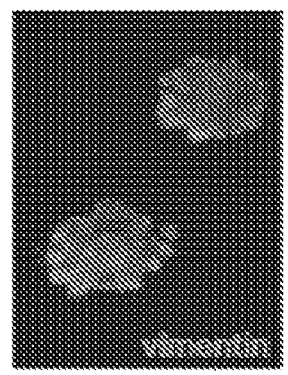
Figure 2E:
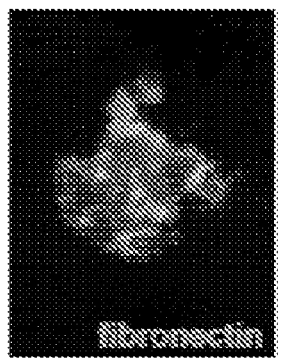
Figure 2F:

Over one week, spheres of proliferating cells appeared, as seen in phase illumination (See FIG. 1A). While many cells adhered to the plastic or died, within 1-10 weeks, spheres of proliferating cells formed (FIG. 2A) which upon dissociation and passaging proliferated and formed new spheres. The majority of samples formed primary tumor spheres, all of which expressed the NB markers NB84 and TH and the SKPs markers vimentin, versican, nestin and fibronectin (FIG. 2B-F). These tumor spheres were selected to provide the enriched preparation of NB TICs.

Example 2

Self-Renewal and Proliferation of NB Tumor Spheres

One of the characteristics of a TIC is that it self-renews over an extended period of time either in culture or in vivo. The present example demonstrates that the NB cancer stem cells, or NB TICs of the invention, posses the ability to self-renew over a defined period of time.

In the present example, a methylcellulose assay (colony sphere-forming ability of single cells is assessed in methylcellulose), and a limiting-dilution assay (growth of isolated single cells is assessed) will be used to demonstrate the activity of the NB TICs identified in the present invention. In self-renewing addition, the proliferative rate of the tumor spheres will also be determined by BrdU labeling.

Methylcellulose Assay:

The percentage of NB sphere-forming cells was assessed by plating in 0.8% methylcellulose. This technique has previously been used for rodent SKPs (17).

In initial studies, 0.2% to 2.0% of the starting tumor cell population formed spheres. A similar assessment of dissociated primary tumor spheres showed that up to 18% of these cells could form a secondary sphere, an enrichment of up to 100-fold in cells capable of growing as colonies in semi-solid medium. In both cases, the number of spheres formed was proportional to the amount of cells plated (FIG. 3B).

Limiting Dilution Assay:

Four (4) of the tumor sphere samples have been passaged 3 or more times, with frequencies ranging from 0.05% to 18% for a stage 1/4S verses stage 4 tumor, respectively. These data indicate that the tumor spheres can self-renew, a major criterion for TICs.

One of the tumor sphere samples derived from a bone marrow aspirate of a stage 4 tumor from relapsed disease (NB12) has now been dissociated and passaged 28 times in liquid culture over a 60 week period. In all cases, passaged and primary tumor spheres displayed the same phenotypic profile. All of the tumor sphere samples will undergo self-renewal analysis; (b) all self-renewal results will be confirmed using limiting dilutions assays, and (c) cell surface markers will be identified to prospectively-identify NB TICs by flow cytometry.

It is anticipated that tumor spheres from high stage tumors will self-renew for longer periods of time and at higher frequencies than those from more differentiated low stage and benign tumors. It is also anticipated that all of the tumor spheres will generate sympathetic neuroblasts at some frequency.

Example 3

NB Tumor Spheres Differentiate into Sympathetic Neuroblasts and Schwann Cells

NB tumor spheres differentiated into sympathetic neuroblasts, a cell type diagnostic for NB. The present example establishes that the cells isolated according to the present invention are TICs for NB, as they are shown herein to differentiate into sympathetic neuroblasts and Schwann cells, the hallmark NB cell type.

When differentiated in conditions used to generate sympathetic neurons from SKPs, tumor spheres from three low stage and one high stage tumor generated morphologically complex cells that were positive for TH, and the neuron-specific proteins III-tubulin and NFM (FIG. 3A). Moreover, a subpopulation of differentiated cells expressed the Schwann cell markers 100β, GFAP, and GalC. In contrast, spheres from two other stage 4 tumors remained largely undifferentiated, and generated only a few cells expressing neuronal or glial proteins. These phenotypes and expression patterns are typical of low and high stage NB. Thus, the NB tumor spheres can regenerate cell types of the original tumor, fulfilling another criterion for TICs.

Example 4

NB Tumor Spheres Form Tumors in vivo

Defining characteristics of TICs are that they (a) are highly enriched for tumor-forming ability relative to the initial tumor cell population and (b) can recapitulate the phenotype of the original tumor in vivo (4). The present example demonstrates that as few as 100 NB tumor sphere cells (the lowest number examined) isolated according to the present invention will form a NB tumor when injected subcutaneously in mice (FIG. 3C, 16, 17), as compared to the $10^6$ cells that are normally required. Since $2 \times 10^6$ cells from established NB cell lines are typically required to form tumors using this protocol (28), this represents an approximately 20,000-fold enrichment in TICs.

The tumor spheres will be used to identify the oncogenic events responsible for maintenance of the tumor phenotype.

Model 1:

To assess whether the NB tumor spheres could form tumors, ten primary spheres (2,500 cells) isolated from a needle biopsy of a tumor (sample designated NB05b) obtained from a patient newly diagnosed with stage 4 NB, were injected subcutaneously into the flanks of NOD/SCID mice, a xenograft model of NB (50).

Figure 3C:
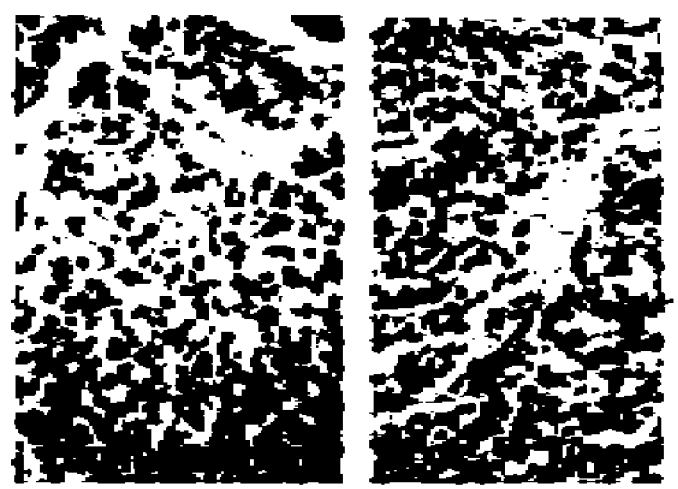

A large tumor arose that contained cells resembling immature neuroblasts with small refractile cell bodies and high nuclear to cytoplasmic ratios, and that immunostained with the NB marker NB84 (FIG. 3C). Since most NB xenograft models with subcutaneous injection require $10^5$-$10^6$ cells to form visible tumors, this result indicates that the NB05 tumor spheres were highly enriched for tumorigenicity, consistent with their identity as TICs. Cells from primary spheres of a second stage 4 bone marrow (NB12) also formed tumors in mice. Tumor formation will be assessed for all of the NB tumor sphere lines in an orthotopic model of NB tumor formation. A small piece of in vivo primary tumors from both NB05b and NB12 patients were used to re-implant and form secondary tumors in vivo.

Model 2—Orthotopic Model:

An orthotopic model of NB will be used to assess tumor formation by NB tumor sphere cells. In this model, injection of NB cells (between $1 \times 10^2$ and $1 \times 10^5$) into the mouse adrenal fat pad (a common site of NB) results in primary tumor growth in the adrenal and distant metastasis to sites such as bone marrow (28). Moreover, these tumors closely resemble human NB. Tumors in this model can be easily quantified 21 days after injection of NB cells. The initial analysis of the NB spheres is conducted by injecting dissociated tumor sphere cells from one stage 4 (NB12) and one ganglioneuroma (NB10) NB.

The different cell populations will be compared for tumorigenicity by injecting from $1 \times 10^2$ to $1 \times 10^5$ dissociated cells into the adrenal fat pad. Cells to be injected include (a) unsorted tumor spheres from different NB stages, (b) FACS-sorted tumor cells that are both positive and negative for tumor sphere markers, (c) cells that have been sorted for tumor sphere markers and then expanded as tumor spheres, and (d) acutely dissociated total NB cells. Tumor masses will be assessed at 1-24 weeks, time points based upon the study of Dirks with orthotopic transplants of brain TICs (14). Tumors will be assessed histologically for morphology typical of NB, by immunohistochemistry for NB84, TH, vimentin, nestin, and βIII-tubulin (all markers for NB neuroblasts), and for proliferation by immunostaining for Ki67. A portion of these secondary tumors will also be dissociated, the cells resorted by flow cytometry, and then either directly injected into mice to determine whether they can be serially passaged (a characteristic of other TICs), or expanded in sphere cultures and characterized as for the initial tumor cell population.

These studies demonstrate the existence of a tumor-initiating stem cell in NB, and provides a system that may be used to characterize how this tumor arises and progresses.

Example 5

NB Tumor Spheres Exhibit Abnormal Karyotypes

To confirm that the NB tumor spheres were derived from NB, metaphase spreads of multiple clones of tumor spheres from sample NB12 (one of the stage 4 samples that generated a tumor) were karyotyped.

Three populations of cells were identified, one 76% diploid and the others tetraploid, with and without double minutes, karyotypes typical of stage 4 NB.

A detailed assessment of clonal tumor sphere cells for DNA content, amplification of MYCN, and loss of heterozygosity (LOH) that often occurs in high stage NB, particularly deletion of 1 p, trisomy of 17 q, and 11 q LOH (1), will be undertaken.

The detailed genomic assessment will include an assessment of expanded clonal tumor spheres for DNA content, amplification of MYCN, and LOH that often occurs in high stage NB and particularly 1 p, 11 q and 17 q LOH (1). This will be accomplished on metaphase preparations of dissociated primary tumor spheres by GTG banding and by single nucleotide polymorphism (SNP) analysis using high-density oligonucleotide arrays. SNP analysis will be particularly valuable for assessing loss of heterozygosity that is common in high grade NB. Expansion of single clonal spheres of human SKP cells has already been achieved, and similar studies (18) have already been performed.

Example 6

Cell Surface Marker Expression

The present example shows that a subpopulation of cells from an original NB tumor can reform tumors, and that these reformed tumor cells possess identifiable cell surface markers associated with NB, including but not limited to NB84, CD44, TrkA, GD2, CD24, CD34, p75NTR, and/or versican.

Flow cytometry was used to identify cell surface markers for NB tumor spheres. These markers will be used to prospectively isolate potential TICs directly from the tumor. Antibodies known to recognize cell-surface proteins that are (a) most highly expressed in high grade NB tumors, including CD44, TrkB, and GD2 [the latter two specific to high grade or relapsed NB, (1,25)], (b) preferentially expressed on low-grade NB and human SKPs, including p75NTR (26,27), (c) are expressed on SKPs, but that have not been tested in NB, including versican, will be used, and (d) other markers of interest in neural crest development and cancers including NB, such as CD20, CD56 and CD29 (57-59).

Among the cell surface markers that are not expressed on SKPs or high grade NB and that will be tested for negative selection are CD106 (mesenchymal stem cell marker), TrkA, and CD31 (endothelial precursor marker). This strategy is anticipated to be highly selective, as NB tumor spheres have already been shown to express NB84 and versican, and a similar strategy has been used by flow cytometry to prospectively isolate SKPs from rodent dermis (26).

The "cell surface signature" identified according to this procedure for NB sphere-forming cells will be used to sort tumor cells into populations that are either positive or negative for these markers. The marker presence or absence will be confirmed using RT-PCR and immunocytochemistry. The positive and negative populations will then be assessed for (a) their capacity to self-renew, using the sphere assay, (b) karyotypic abnormalities characteristic of NB, and (c) their ability to re-form tumors in vivo. A subpopulation of NB TICs will be isolated that will express markers of SKPs and NB, and that will subsequently self-renew as spheres and reform tumors, while the negative population will neither self-renew nor form tumors.

The tumor-initiating ability of high-grade tumor spheres is highly enriched in the $CD24^+/CD34^-$ fraction of high-grade NB tumor spheres (FIG. 20). CD24 was chosen as a putative marker of NB TICs because it was reported to be expressed on renal cell carcinomas, small cell lung tumors, breast cancer TICs as well as NB (64-65). CD34 was chosen as a putative marker of NB TICs because it had been reported that patients relapsed with NB following CD34+ peripheral blood stem cell transplantation (62). The $CD24^+/CD34^+$ Fraction of NB TICs was found to be highly enriched for tumor-initiation in an orthotopic model of NB.

Example 7

Low Stage NB, High Stage NB, Bone Marrow Metastasis and Relapsed Tumor Characterization of TIC Populations Neuroblastoma TICs from different grades of NB, obtained from tumors and metastases, and before and after relapse, will be used to identify molecular differences between these cells and others, and to determine how NB initiates and progresses, and why some NB are benign and others are fatal. Identifying these differences will be used to define therapies specific for individual patient NB.

Marker and gene expression differences will be assessed on different populations of tumor spheres by (a) comparative immunocytochemistry, (b) RT-PCR, and (c) expression profiling using NB-specific cDNA microarray. For immunocytochemistry, NB tumor spheres will be analyzed for the NB markers NB84 and TH, the SKP markers versican, vimentin, nestin, and fibronectin, the neuronal markers NFM and βIII-tubulin, the Schwann cell markers s100β, GFAP and CNPase, and the cell surface antigens defined in flow cytometry studies.

For RT-PCR, expression of genes will be assessed that are (a) enriched in high-grade NB (as determined by cDNA microarray), (b) that regulate neural crest development such as hAsh, hTwist, and Id2 (29), (c) the unfavorable prognosis markers TrkB, MYCN, and mutant Phox2b, and (d) the favorable prognosis marker TrkA. Western blot analysis will be performed when antibodies are available that recognize the human proteins, such as for TrkA and TrkB. These data will be used to choose a limited number of samples for expression profiling, which will be accomplished using a NB-specific cDNA microarray reported (30). This analysis is expected to predict unfavorable and favorable NB at a very high accuracy.

Candidates will be selected based on further analysis of the data to identify candidate genes to test (30). Total RNA from $1 \times 10^7$ TICs, a number that can be obtained with at least two of the NB tumor sphere cultures. Genes preferentially expressed in TICs from high or low-grade NB and from bone marrow or following relapse, and that have been implicated in the control of cell growth, survival, metastasis or tumorigenicity will be assessed for their role in NB.

Example 8

Molecular Events in Transformation of Neural Crest Precursors into NB TICS, and Suppression of Tumorigenic Properties of NB TICs To identify the molecular events involved in the transformation of neural crest precursors into NB TICs, human NCPs and NB TICs will be genetically manipulated with oncogenes or siRNAs to potential tumor suppressors of NB, and re-implant these into (i) the adrenal fat pad in mouse where most NB tumors arise, and (ii) the chick neural crest migratory stream, a system where NCPs differentiate into neural crest progeny, thereby permitting the definition of the developmental stage at which potential oncogenes cause tumor formation.

Among the genes to be assessed will be the unfavorable prognosis NB markers MYCN, Id2, h-Twist, mutant Phox2b, and ΔNp73, and the favorable prognosis markers TrkA and overexpressed Phox2b. Genes will also be assessed that are preferentially expressed or suppressed in TICs from different stages of NB.

Example 9

Molecular Events in the Appearance and Progression of NB

The molecular events that regulate the appearance and progression of NB are relatively uncharacterized. Of the unfavorable prognosis markers, only MYCN has been shown to induce NB when over expressed in a transgenic model that targets sympathoadrenal precursors and their differentiated progeny (31). However, MYCN-induced NB in mice arises much later than human NB, and rarely metastasizes, suggesting that other oncogenic events are required to reproduce the full NB phenotype, or that events that induce NB differ in mouse and human.

The proliferative and tumor-inducing potential of several genes implicated in NB will be assessed, in the three cell types human NB tumor spheres, human SKPs, and rodent adrenal gland precursors. The genes that will be initially tested are MYCN, Id2, h-Twist, ΔNp73, Phox2b, TrkB, and TrkA. The rationale for choosing these genes is as follows.

(i) MYCN is the best-known poor prognosis marker in NB, correlating well with rapid tumor progression, poor outcome, and treatment failure (1). It is amplified and over expressed in 22% of high stage NB, and its inhibition is required for the cell cycle arrest of sensory precursor cells (1,32). MycN may function as a proliferative protein, or suppress the expression of genes important for cell cycle arrest and differentiation, such as TrkA. (ii) Expression of the Id2 inhibitory helix-loop-helix (HLH) protein strongly correlated in one study with poor outcome in NB (33) and MycN-mediated cell cycle progression requires the Id2-induced suppression of Rb activity (33). (iii) h-Twist is a bHLH transcription factor that is expressed primarily in MYCN amplified NB (34). It is required in at least one NB cell line to override the apoptotic activity of MYCN by suppressing ARF and p53 activity (34). MYCN is likely to be tumorigenic only in cells over expressing h-Twist, mutated p53 (rare in NB), or suppressors of p53 activity such as ΔNp73. (iv) Phox2b is a homeobox domain transcription factor that in mice is required for differentiation of noradrenergic neurons, and that together with Mash1, drives progenitors to become post-mitotic sympathetic neurons (35, 36). Frameshift germline Phox2b mutations (R100L) have been reported in a subset of familial NB, while over expression of wild type Phox2b correlates with favorable prognosis (3).

Mutations in Phox2b may therefore block the differentiation of sympathoadrenal precursors and contribute to NB, possibly by dimerizing with and inhibiting wild-type Phox2b. (v) ΔNp73, a p53 family member, is a major survival protein in the sympathoadrenal lineage (37). ΔNp73 expression strongly correlates with poor outcome in NB, and is detected in cells lines with amplified MYCN (38). Since this protein can ablate p53 activity (37), it may collaborate with MycN (the protein) to induce proliferation, and/or promote the survival of sympathoadrenal precursors containing unstable genomes. (vi) TrkA is a poor-prognosis NB marker that has been shown to induce survival, migration and invasion, and resistance to chemotherapeutic agents when expressed in NB cell lines (1, 39, 40). It was also observed that TrkB activation induces NB neuronal differentiation (41). However, TrkB-expressing NB cells continue to proliferate as they differentiate, which is similar to the neuroblast phenotype of NB tumors. Unfavorable tumors also express BDNF, the TrkB ligand (1). (vii) The expression of the TrkA Nerve Growth Factor (NGF) receptor is highly correlated with favorable NB outcome, lower stage, and absence of MYCN amplification (1). TrkA induces neuronal differentiation, suppression of MYCN levels, cell cycle arrest, and apoptosis in NB cell lines, depending upon its expression level (1, 42, 43). TrkA may function by promoting the terminal differentiation and death of inappropriately cycling neuroblasts.

The above data suggests that NB proto-oncogenes can be grouped into those that induce or maintain the proliferation of progenitors and block differentiation of their post-mitotic progeny such as MYCN, Id2, and mutant Phox2b, and those that prevent p53 function or that are potent survival proteins such as h-Twist, TrkB, and ΔNp73. The expression of any pair of pro-proliferation and survival proteins will transform SKPs or adrenal precursor cells to a NB fate. Likewise, over expression of TrkA or wild type Phox2b, or suppression of the expression of the above proteins via siRNA, will inhibit the proliferation and tumorigenesis of NB TICs and induce their differentiation.

The functional importance of genes preferentially expressed in TICs from high or low-grade NB, from bone marrow, and following relapse, will also be assessed.

Data, Model Systems

Figure 4A:
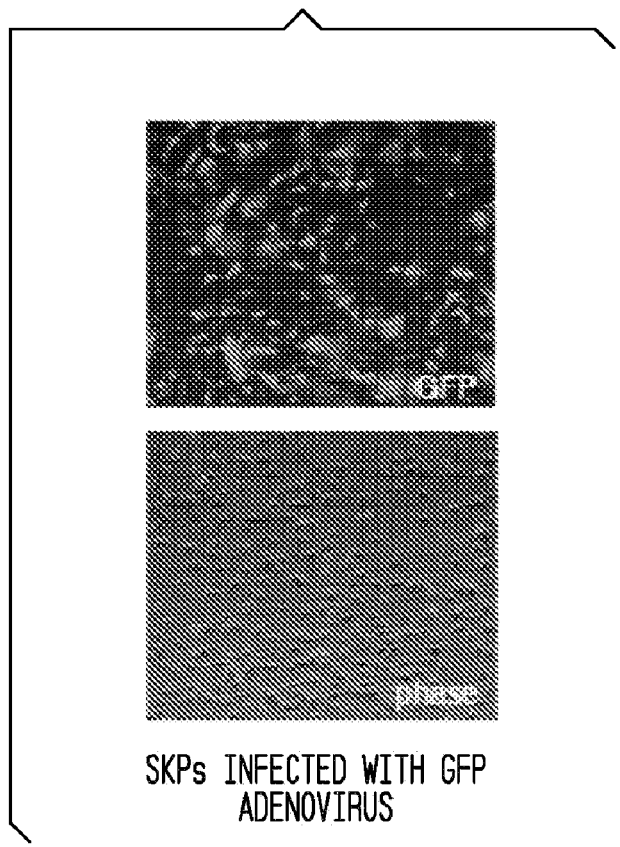
FIG. 4A-4E, according to some aspects of the invention, demonstrate SKPs infected with GFP adenovirus. (4A) SKPs spheres were dissociated, plated on laminin/lysine-coated slides, and infected with AdGFP. Virtually all cells in the culture expressed GFP. (4B-4E) SKPs (expressing YFP) migrate when transplanted in ovo into the developing chick neural crest. (4B) Picture of a single YFP-labeled SKP. (4C) YFP-labeled cells in the DRG. (4D, 4E) SKPs migrate into peripheral neural crest targets and differentiate into glia. (4D) SKPs that have migrated into the sympathetic ganglia (ganglia labeled with βIII-tubulin) (NT). (4E) SKPs migrating to the DRG label with the Schwann cell markers 100β.
Figure 4B:
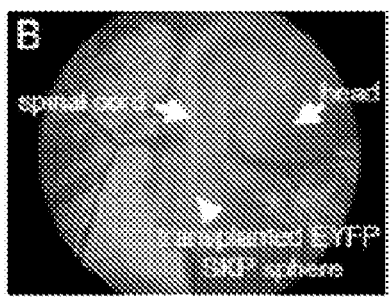
Figure 4C:
Figure 4D:
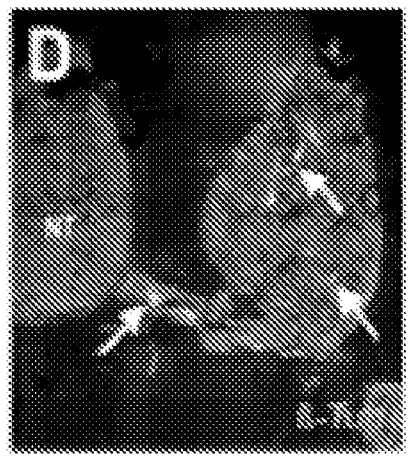
Figure 4E:
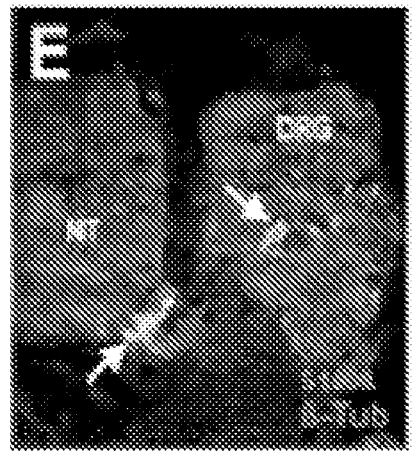

Three cell systems; human SKPs as a human NCP, mouse neonatal adrenal precursor cells, and human NB TICs will be used. The sorted, expanded NB cells for these studies will be used. The unsorted NB tumor spheres may also be used. These genes will be introduced into these cells using adenovirus or lentivirus. Several hundred recombinant adenovirus vectors encoding epitope-tagged genes and GFP have been constructed, and will be used for the functional analysis of proteins in neurons and progenitors, including MYCN, TrkA, TrkB, Id2, and ΔNp73 (37,43-46). Moreover, these genes have been for up to 7 days in SKPs using recombinant adenovirus (FIG. 4A). However, since gene function will be assessed in proliferating cells in vivo, the lentivirus vectors will also be used, which efficiently integrate into genomes and infect precursor cells at efficiencies of 80-90% (47, 48).

Example 10

In vivo Systems to Assess Tumorigenesis and Differentiation

The present example is presented to demonstrate the utility of the present invention for providing an in vivo model for mammalian neural crest differentiation. The methods thus posses the major advantage that the transplanted, transformed precursors will undergo the same differentiation steps that they would during human development, thereby potentially unmasking effects that are differentiation-stage specific. Aberrant growths arising from transformed CNS neural precursors within the chick spinal cord in ovo have previously been observed, even further establishing the feasibility of studying tumorigenesis in this system.

Genetically manipulated cells will be implanted into (i) the adrenal fat pad in mouse, and (ii) the embryonic chick neural crest migratory stream in ovo. Single SKP spheres transplanted into the latter system migrate into peripheral neural crest targets, including the spinal nerve, DRG, and sympathetic ganglia (the latter a site for NB), and differentiate into neural crest progeny (FIG. 4B-E, 17).

Example 11

Candidate NB Oncogenes and SKPs, Adrenal Precursor Cells, and/or Cells from Low-stage NB and Proliferation Activity in vitro, and in the Formation of Tumors NB neuroblasts and the NB tumor spheres continue to proliferate even as they express sympathetic neuron markers. SKPs, adrenal precursors, and cells from low-stage NB, will be used to express the proliferative NB oncogenes in combination with the pro-survival oncogenes that have been described above, and proliferation and differentiation of these cells will be monitored (a) under the sphere expansion conditions described herein, in FGF and EGF, and (b) under normal neural differentiation conditions as described herein, in the absence of mitogens. Note that SKPs will not form tumors when implanted into chick (17) or mice (49). For these studies, one proliferative and one prosurvival protein will be used per study (see FIG. 5).

Figure 1C:
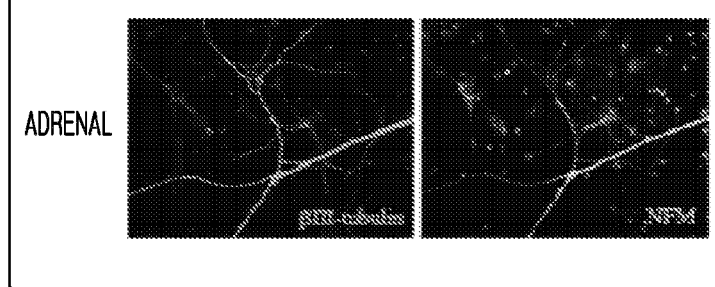

Cells will be co-transduced with GFP as a marker, and proliferation will be monitored by BrdU labeling and Ki67 immunocytochemistry, and differentiation into sympathetic neuroblasts or neurons by immunocytochemistry for nestin, vimentin, TH, βIII-tubulin, and NFM. Expression of the virally-expressed proteins will be confirmed by immunocytochemistry and Western blotting, as done for MYCN, Id2, and TrkB (43, 45,46). For TrkB, cells will be treated with BDNF, and TrkB tyrosine phosphorylation assessed (41). One or more combinations of these potential oncogenes, for example MYCN and Δp73, is anticipated to cause the appearance of proliferating cells with characteristics of sympathetic neurons i.e. NB neuroblasts. In contrast, control SKPs and adrenal precursors will differentiate into post-mitotic sympathetic neurons, as previously shown (18, FIG. 1C).

Having established which single/combinations of proto-oncogenes perturb proliferation or differentiation in culture, it will then be determined if these perturbations also cause human SKPs, rodent adrenal precursors, or cells from low-stage NB to form tumors in vivo. Human SKPs are genetically and phenotypically stable for over a year in culture (18), and neither rodent nor human SKPs form tumors in chick, mice or rats (17). However, it is not yet known whether the low-stage NB tumor sphere cells will form tumors; if they do, potential enhancement of tumor growth will be assessed. The genetic manipulations in these studies will be similar to those described for culture analysis, except that lentiviral transduction will be used.

For transplantation into the orthotopic adrenal fat pad model, $1\times10^2$ to $1\times10^4$ transformed, GFP-tagged cells will be implanted and tumor growth will be quantified for engraftment rate at 1-24 weeks post injection. Tumors will be assessed by histology for neuroblasts, and immunocytochemically for the NB markers NB84 and TH, the proliferation marker Ki67, and for the epitope tag on the expressed transduced protein(s) as described (50). For transplantation into the embryonic chick, the transduced cells will be grown as spheres, and implanted into the chick neural crest migratory stream (FIG. 4B-E, 17). Cell migration to peripheral neural crest targets will be confirmed by the presence of GFP-positive cells (FIG. 4B-E), and tumor masses identified as described herein.

Example 12

Overexpression of TrkA or Phox2b, NB TICs Dividing Activity, Differentiation, Apoptosis and Tumorigenicity A converse study will be conducted to (i); express TrkA or Phox2b in dissociated NB tumor sphere cells from stage 4 tumors, and observed for activity to differentiate or die and/or suppresses tumorigenicity. These studies will be performed in culture, and will transduce the cells and assess cellular proliferation and differentiation as described in (i) and apoptosis by TUNEL.

NGF will be added to cells expressing TrkA. From the gene expression array analysis, it will be determined which NB TICs express MYCN, Id2, h-Twist, mutant Phox2b, TrkB or ΔNp73. The levels of these putative proto-oncogenes will be selectively suppressed using shRNA viral vectors or siRNA in those cells. The cells will be examined to determine if this inhibits their proliferation and/or promotes their differentiation or death. Similar approaches have previously been used to manipulate primary CNS precursors in culture and in vivo (51).

To determine if these same manipulations inhibit NB tumor sphere tumorigenicity, the manipulated cells will be implanted into the mouse adrenal fat pad and the chick neural crest migratory stream, and tumorigenicity as described for (i) above will be assessed. One or more of these approaches will be examined to determine if they suppress the transformed phenotype of NB TICs. However, it is possible that the higher-grade NB TICs may carry so many genetic perturbations that single manipulations will be insufficient to reverse their phenotype. If this proves to be the case, then similar studies with lower-grade NB tumor spheres which carry fewer genetic perturbations will be conducted.

Isolation of NB TICs and of several types of NCPs will permit the characterization of molecular events regulating the transformation and progression of NB, and whether there are molecular and phenotypic differences in cells from different stages of NB.

Example 13

Screening Method to Detect Alterations in Cell Viability/Proliferation

The present example provides a description of the screening method use to identify the chemical entities capable of affecting NB cells reported in the present series of studies.

Malignant NB is the most common extra-cranial solid tumor in children. Survival of patients older than 1 year remains less than 30% with conventional therapies. Candidate NB TICs were isolated, and it was hypothesized that TICs are related to SKPs. Both SKPs and TICs originate from the neural crest, express similar neural crest markers, and differentiate in vitro into similar cell types. The availability of two neural crest stem cell sources, one from the NB tumor and the other from the skin of the same patient, affords us a unique opportunity for therapeutic target discovery.

Study 1 Screen:

Materials and Methods:

To identify compounds that suppress the growth and survival of NB TICs and not nontransformed normal cells (SKPs), a cell-based assay was established and used in which NB TICs from a multiple relapse NB patient (NB 12, passage 6-17) and normal SKPs (FS90passage 2-5) were tested in parallel to detect specific alterations of cell viability/proliferation. For each cell type, cells were passaged 5 days prior to screening. Three thousand (3000) cells in 100 μL of SKPs growth media (B27, FGF, EGF, P/S, FUNGIZONE™ (antifungal agent) in DMEM:F12 with 50% hFS conditioned media) were robotically plated in individual wells of uncoated 96 well plates and treated with test compound for 30 hours, prior to a 24 hour incubation in the presence of alamarBlue® and subsequent fluorometric reading. Under these conditions, the alamarBlue® signal displayed a linear response with time, background was minimal, and the dynamic range satisfactory (i.e., the alamarBlue® reading at 0 hours vs. 24 hours was>10 fold different).

The robustness of the screen was initially evaluated by using a collection of 1280 bioactive compounds (LOPAC™ library, Sigma). For both normal SKPs and NB TICs, variability of signals was low, with CV values ranging between 3.5-4.5% across the plates, and the dimensionless, statistical parameters Z' and Z factors were >0.5, suggesting an excellent assay quality. "Hits" were defined as the compounds whose signals were shifted away by at least 3× standard deviations (99.73% confidence interval) from the mean of the general sample population.

Results:

The screen of the LOPAC™ library at 5 μM yielded 13 "hits" which were found to affect both normal and NB cells. We also identified 18 compounds that selectively target NB cells. Four compounds selectively targeted normal cells.

TABLE 2

| 13 compounds that affect both normal and NB cells: |
| --- |
| Ancitabine hydrochloride |
| Brefeldin A from Penicillium brefeldianum |
| Calmidazolium chloride |
| CGP-74514A hydrochloride |

TABLE 2-continued

13 compounds that affect both normal and NB cells:

Dihydroouabain
Diphenyleneiodonium chloride
Emetine dihydrochloride hydrate
Idarubicin
Mitoxantrone
Ouabain
Quinacrine dihydrochloride
Ammonium pyrrolidinedithiocarbamate
Sanguinarine chloride

TABLE 3

18 compounds that selectively target NB cells.

Loratadine
MG 624
Melphalan
Podophyllotoxin
Ro 25-6981 hydrochloride
Rotenone
DL-Stearoylcarnitine chloride
Taxol
Vincristine sulfate
Vinblastine sulfate salt
Chelerythrine chloride
Colchicine
Cytosine-1-beta-D-arabinofuranoside hydrochloride
Dequalinium dichloride
(S)-(+)-Camptothecin
Dequalinium analog, C-14 linker
2,3-Dimethoxy-1,4-naphthoquinone
Etoposide

TABLE 4

4 compounds selectively target normal cells:

8-Methoxymethyl-3-isobutyl-1-methylxanthine
Oligomycin A
Sphingosine
Thapsigargin Study 2 Screen:

Materials and Methods

The PRESTWICK CHEMICAL LIBRARY® was screened at 5 µM using FS90 and NB12 and at 1 µM using NB12 only due to the high number of "hits" at 5 µM. This screen identified 9 compounds that selectively target NB12 and 15 compounds that affect both NB12 and FS90.

Results:

TABLE 5

9 compounds that selectively target NB12:

Azaguanine-8
Paclitaxel
Camptothecine (S.+)
Colchicine
Etoposide
Doxorubicin hydrochloride
Lanatoside C
Podophyllotoxin
Proscillaridin A

TABLE 6

15 compounds that affect both NB12 and FS90:

Disulfiram
Mitoxantrone dihydrochloride
Anisomycin
Cephaeline dihydrochloride heptahydrate
Digitoxigenin
Digoxin
Strophantine octahydrate
Puromycin dihydrochloride
Daunorubicin hydrochloride
Emetine dihydrochloride
Methyl benzethonium chloride
Strophanthidin
Cycloheximide
Thonzonium bromide
Sanguinarine Study 3 Screen:

Methods:

The results from the LOPAC™ and PRESTWICK CHEMICAL LIBRARY® screens were confirmed using FS90, FS105, and NB12. Thirty-six (36) compounds were confirmed that specifically affect NB12 and 29 compounds that affect FS90/105 and NB12. Thirty-two (32) compounds were selected for $IC_{50}$ determinations using FS90, FS105, and NB12. $IC_{50}$ for the remaining compounds of interest will be tested at a later date (in combination with hits from additional libraries).

Results

TABLE 7

36 compounds that specifically affect NB12

(S)-(+)-Camptothecin
2.3-Dimethoxy-1.4-naphthoquinone
Ancitabine hydrochloride
Antimycin A
Azaguanine-8
Benzethonium chloride
Camptothecine (S.+)
Chelerythrine chloride
Ciclopirox ethanolamine
Clofazimine
Colchicine
Colchicine
Cycloheximide
Cytosine-1-beta-D-arabinofuranoside hydrochloride
Dequalinium analog. C-14 linker
Dequalinium dichloride
Dequalinium dichloride
Digoxigenin
Diphenyleneiodonium chloride
DL-Stearoylcarnitine chloride
Doxorubicin hydrochloride
Etoposide
Etoposide
MG 624
Mycophenolic acid
Paclitaxel
Parthenolide
Podophyllotoxin
Podophyllotoxin
Primaquine diphosphate
Quinacrine dihydrochloride
Quinacrine dihydrochloride dihydrate
Scoulerine
Taxol
Vinblastine sulfate salt
Vincristine sulfate

TABLE 8

29 compounds that affect FS90/105 and NB12

Alexidine dihydrochloride
Ammonium pyrrolidinedithiocarbamate
Amodiaquin dihydrochloride dihydrate
Anisomycin
Brefeldin A from Penicillium brefeldianum
Calmidazolium chloride
Cephaeline dihydrochloride heptahydrate
CGP-74514A hydrochloride
Daunorubicin hydrochloride
Digitoxigenin
Digoxin
Dihydroouabain
Disulfiram
Emetine dihydrochloride
Emetine dihydrochloride hydrate
Idarubicin
Lanatoside C
Methyl benzethonium chloride
Mitoxantrone
Mitoxantrone dihydrochloride
Ouabain
Proscillaridin A
Puromycin dihydrochloride
Sanguinarine
Sanguinarine chloride
Strophanthidin
Strophantine octahydrate
Terfenadine
Thonzonium bromide

TABLE 9

32 compounds selected for IC50 determinations using FS90, FS105, and NB12:

(S)-(+)-Camptothecin
Ammonium pyrrolidinedithiocarbamate
Amodiaquin dihydrochloride dihydrate
Antimycin A
Avermectin B1
Azaguanine-8
Chelerythrine chloride
Clofazimine
Colchicine
Dequalinium analog, C-14 linker
Dequalinium dichloride (LOPAC compound)
Dequalinium dichloride (Prestwick compound)
Digoxin
Dihydroouabain
Diphenyleneiodonium chloride
DL-Stearoylcarnitine chloride
Etoposide
Idarubicin
Loratadine
MG 624
Myophenolic Acid
Paclitaxel
Parthenolide
Podophyllotoxin
Primaquine diphosphate
Quinacrine dihydrochloride
Sanguinarine chloride
Scoulerine
Strophanthidin
Terfenadine
Vinblastine sulfate salt
Vincristine sulfate Study 4—Screen Results at 5 μM:

The SPECTRUM™ collection was screened using the same protocol. At 5 μM, the initial screen identified 35 hits that affect NB12 and FS90, no hits that specifically target FS90, and 41 hits that specifically target NB12. The screen was repeated at 5 μM and 1 μM using NB12 and FS90 to confirm these hits and identified 34 hits that affect NB12 and FS90, no hits that specifically target FS90, and 33 hits that specifically target NB12. Following the SPECTRUM™ confirmatory screen, IC50 determinations for an additional 32 compounds were performed.

TABLE 10

34 hits that affect NB12 and FS90:

3-METHYLORSELLINIC ACID
5alpha-CHOLESTAN-3beta-OL-6-ONE
5-AZACYTIDINE
AKLAVINE HYDROCHLORIDE
CETRIMONIUM BROMIDE
CHELIDONINE (+)
COLCHICEINE
COLCHICINE
CYTARABINE
DACTINOMYCIN
DEOXYSAPPANONE B 7.3'-DIMETHYL ETHER
DIGITOXIN
DIHYDROGAMBOGIC ACID
DISULFIRAM
EMETINE
GENTIAN VIOLET
JUGLONE
LANATOSIDE C
LYCORINE
MITOMYCIN C
OXYPHENBUTAZONE
PATULIN
PERIPLOCYMARIN
PERUVOSIDE
PHENYLMERCURIC ACETATE
PUROMYCIN HYDROCHLORIDE
PYRITHIONE ZINC
PYRROMYCIN
RETUSOQUINONE
SANGUINARINE SULFATE
SARMENTOGENIN
STROPHANTHIDIN
THIMEROSAL
TOMATINE

TABLE 11

33 hits that specifically target NB12:

10-HYDROXYCAMTOTHECIN
4'-DEMETHYLEPIPODOPHYLLOTOXIN
ANDROGRAPHOLIDE
AMODIAQUINE DIHYDROCHLORIDE
AMSACRINE HYDROCHLORIDE
ANCITABINE HYDROCHLORIDE
BENZALKONIUM CHLORIDE
BENZETHONIUM CHLORIDE
BEPRIDIL HYDROCHLORIDE
beta-PELTATIN
CAMPTOTHECIN
CETYLPYRIDINIUM CHLORIDE
CHOLESTAN-3beta.5alpha.6beta-TRIOL
CICLOPIROX OLAMINE
CONVALLATOXIN
CRASSIN ACETATE
CRINAMINE
DIGOXIN
ERYSOLIN
GAMBOGIC ACID
IMIDACLOPRIDE
LIMONIN

TABLE 11-continued

33 hits that specifically target NB12:

MECHLORETHAMINE
MECLIZINE HYDROCHLORIDE
OUABAIN
OXYBENDAZOLE
PACLITAXEL
PARAROSANILINE PAMOATE
PARTHENOLIDE
PODOPHYLLOTOXIN ACETATE
STROPHANTHIDINIC ACID LACTONE ACETATE
TENIPOSIDE
VINBLASTINE SULFATE

TABLE 12

32 Compounds selected for IC50 Determinations:

Aklavine hydrochloride
AMSACRINE HYDROCHLORIDE
ANCITABINE HYDROCHLORIDE
ANDROGRAPHOLIDE
BEPRIDIL HYDROCHLORIDE
beta-PELTATIN
CGP-74514A hydrochloride
CHOLESTAN-3beta.5alpha.6beta-TRIOL
CICLOPIROX OLAMINE
CONVALLATOXIN
CRASSIN ACETATE
CRINAMINE
DIHYDROGAMBOGIC ACID
ERYSOLIN
Gambogic Acid
IMIDACLOPRIDE
JUGLONE
LIMONIN
MECHLORETHAMINE
MECLIZINE HYDROCHLORIDE
Mitomycin C
Mitoxantrone hydrochloride
OUABAIN
OXYBENDAZOLE
PARAROSANILINE PAMOATE
PERIPLOCYMARIN
PERUVOSIDE
Prenyletin
PYRITHIONE ZINC
TENIPOSIDE
Tomatidine hydrochloride
TOMATINE These results suggest that patient-specific therapeutics, as well as the molecular and biochemical alterations that lead to NB, can be identified using this assay.

Example 14

Identified Compounds that Affect Normal, Neuroblastoma or Neuroblastoma and Normal (Non-Neuroblastoma) Cells

The present example provides a description of the screening method used to identify and select chemical entities capable of affecting (i.e., reducing and/or inhibiting) NB cells. The screening method is used here with the LOPAC™ compound collection. (LOPAC™ library, Sigma).

Candidate NB TICs were isolated. These TICs were used in the screening assay for the identification of these kinds of compounds because they are related to SKPs. For example, both SKPs and TICs originate from the neural crest, express similar neural crest markers, and differentiate in vitro into similar cell types. The availability of two neural crest stem cell sources, one from the NB tumor and the other from the skin of the same patient, affords an approach for the therapeutic target discovery provided here.

Materials and Methods:

Methods:

To identify compounds that specifically target NB TICs, a cell-based assay in which TICs from a NB patient and normal human pediatric SKPs were tested in parallel. Cells were treated with test compound prior to incubation with a cell viability dye. For both cell sources, signal variability was low and the Z' and Z factors were >0.5, suggesting excellent assay quality. Hits were defined as compounds whose signals were shifted at least 3 standard deviations from the mean.

Results:

Compounds that Affect Neuroblastoma Cells and Normal Cells

From 3 libraries of compounds, the LOPAC™ collection, the PRESTWICK CHEMICAL LIBRARY® Collection and the SPECTRUM™ Collection, 46 compounds were found to affect both normal and NB cells. These 46 compounds are listed in Table 13.

TABLE 13

Normal and Neuroblastoma Hits

3-METHYLORSELLINIC ACID
5alpha-CHOLESTAN-3beta-OL-6-ONE
5-AZACYTIDINE
AKLAVINE HYDROCHLORIDE
Alexidine dihydrochloride
Ammonium pyrrolidinedithiocarbamate
Anisomycin
Brefeldin A from Penicillium brefeldianum
Calmidazolium chloride
Cephaeline dihydrochloride heptahydrate
CETRIMONIUM BROMIDE
CHELIDONINE (+)
COLCHICEINE
DACTINOMYCIN
Daunorubicin hydrochloride
DEOXYSAPPANONE B 7.3'-DIMETHYL ETHER
Digitoxigenin
Digoxin
DIHYDROGAMBOGIC ACID
Dihydroouabain
Disulfiram
EMETINE
GENTIAN VIOLET
JUGLONE
LANATOSIDE C
LYCORINE
Methyl benzethonium chloride
MITOMYCIN C
Mitoxantrone
OXYPHENBUTAZONE
PATULIN
PERIPLOCYMARIN
PERUVOSIDE
PHENYLMERCURIC ACETATE
Proscillaridin A
Puromycin dihydrochloride
PYRITHIONE ZINC
PYRROMYCIN
RETUSOQUINONE
Sanguinarine
SARMENTOGENIN
Strophanthidin
Terfenadine
THIMEROSAL
Thonzonium bromide
TOMATINE Table 14: 54 Identified Compounds that Affect NB Cells Fifty-four (54) compounds selected from the LOPAC™ collection, PRESTWICK CHEMICAL LIBRARY® Collection and the SPECTRUM™ Collection, were found to selectively target NB cells. These 54 compounds appear in Table 14.

TABLE 14

| Neuroblastoma Specific Hits |
| --- |
| 10-HYDROXYCAMTOTHECIN |
| 2.3-Dimethoxy-1.4-naphthoquinone |
| 4'-DEMETHYLEPIPODOPHYLLOTOXIN |
| Amodiaquin dihydrochloride dihydrate |
| AMSACRINE HYDROCHLORIDE |
| Ancitabine hydrochloride |
| ANDROGRAPHOLIDE |
| Antimycin A |
| Azaguanine-8 |
| BENZALKONIUM CHLORIDE |
| Benzethonium chloride |
| BEPRIDIL HYDROCHLORIDE |
| beta-PELTATIN |
| Camptothecin (S.+) |
| CETYLPYRIDINIUM CHLORIDE |
| CGP-74514A hydrochloride |
| Chelerythrine chloride |
| CHOLESTAN-3beta.5alpha.6beta-TRIOL |
| Ciclopirox ethanolamine |
| Clofazimine |
| CONVALLATOXIN |
| CRASSIN ACETATE |
| CRINAMINE |
| Cycloheximide |
| Cytosine-1-beta-D-arabinofuranoside hydrochloride |
| Dequalinium analog. C-14 linker |
| Dequalinium dichloride |
| Diphenyleneiodonium chloride |
| DL-Stearoylcarnitine chloride |
| Doxorubicin hydrochloride |
| ERYSOLIN |
| Etoposide |
| GAMBOGIC ACID |
| Idarubicin |
| IMIDACLOPRIDE |
| LIMONIN |
| Loratadine |
| MECHLORETHAMINE |
| MECLIZINE HYDROCHLORIDE |
| MG 624 |
| Mycophenolic acid |

TABLE 14-continued

| Neuroblastoma Specific Hits |
| --- |
| Ouabain |
| OXYBENDAZOLE |
| Paclitaxel |
| PARAROSANILINE PAMOATE |
| Parthenolide |
| Podophyllotoxin |
| Primaquine diphosphate |
| Quinacrine dihydrochloride |
| Scoulerine |
| Taxol |
| TENIPOSIDE |
| Vinblastine sulfate salt |
| Vincristine sulfate |

Four (4) compounds selected from the LOPAC™ collection, PRESTWICK CHEMICAL LIBRARY® Collection and the SPECTRUM™ Collection, were found to successfully treat a NB patient and were selected as NB specific hits according to the assay criteria provided herein. These compounds serve as positive controls in the selection and screening methods. These results emphasize the validity of the assay in identifying active agents for treating NB. These 4 compounds are listed in Table 15.

TABLE 15

| 4 Identified Compounds that are used to Treat the Neuroblastoma Patient |
| --- |
| Patient Hits (i.e. drugs that were used to treat patient AND were selected as NB specific hits) |
| Ancitabine hydrochloride (aka cyclocytidine) |
| Doxorubicin hydrochloride (aka adriamycin) |
| Etoposide |
| Vincristine sulfate |

These results suggest that patient-specific therapeutics as well as novel molecular effectors of NB can be identified using this assay.

Example 15

Cumulative Screening Assay Selection Results

The present example presents the tabulated data obtained with the various chemical library screens conducted.

TABLE 16

| Library | Name | Repeated | NB hit only | NB + FS hit | IC50 test? | target/mechanism |
| --- | --- | --- | --- | --- | --- | --- |
| S | 10-HYDROXYCAMTOTHECIN | X | X | | | modified camptothecin |
| L | 2.3-Dimethoxy-1.4-naphthoquinone | X | X | | | ROS modulator/Redox cycling agent used to study role of ROS |
| S | 3-METHYLORSELLINIC ACID | X | | X | | *Aspergillus terreus* fungal metabolite; possible antioxidant |
| S | 4'-DEMETHYLEPIPODOPHYLLOTOXIN | X | X | | | |
| S | 5alpha-CHOLESTAN-3beta-OL-6-ONE | X | X | | | Cholesterol oxidation product; cytotoxic due to oxidative stress or cytoskeleton disruption |

TABLE 16-continued

| Library | Name | Repeated | NB hit only | NB + FS hit | IC50 test? | target/mechanism |
|---|---|---|---|---|---|---|
| S | 5-AZACYTIDINE | X | | X | | |
| S | ACRIFLAVINIUM HYDROCHLORIDE | | | | | intercalating agent that interferes with DNA replic/transcription; antitumor, antiproliferative |
| S | ACRISORCIN | | | | | topical anti-infective from 1960s |
| S | AKLAVINE HYDROCHLORIDE | X | | X | X | natural product; anti-infective; related structures have broad activity against NIH tumor lines |
| P | *Alexidine dihydrochloride* | X | | X | | phospholipase inh; oral gingivitis rinse |
| S | ALEXIDINE HYDROCHLORIDE | | | | | |
| P | Alprostadil | | | | | vasodilator; erectile dysfunction, pallative care for neonatal congenital heart defects |
| L | *Ammonium pyrrolidinedithiocarbamate* | X | | X | X | blocks NOS mRNA translation |
| P | !Amodiaquin dihydrochloride dihydrate | X | X | | X | antimalarial; treatment of CNS degeneration (Alzheimer, MS) |
| S | !AMODIAQUINE DIHYDROCHLORIDE | X | X | | | antimalarial; 4-aminoquinoline family; narrow therapeutic/toxic window in children |
| S | AMSACRINE HYDROCHLORIDE | X | X | | X | topo II inh; used in AML; may also be active vs malaria |
| L | Ancitabine hydrochloride | X | X | | | cyclocytidine HCl; DNA-synthesis inhibitor (cytosine analog); antileukemic |
| S | ANCITABINE HYDROCHLORIDE | X | X | | X | |
| S | ANDROGRAPHOLIDE | X | X | | X | Chinese herbal medicine; anti-inflamm; immune boosting?; anti-cancer vs HL60, MCF7, others through G0/G1 block and apoptosis induction |
| P | Anisomycin | X | | X | | protein synthesis inh thru peptidyl transferase of 80S ribosome; treatment activates p54, MAPK, SAPK |
| P | #Antimycin A | X | X | | X | antifungal, antimicrobial; blocks e-transport between cytochrome B and cytochrome C; bind the BH3 domain of Bcl-xL and induce apoptosis in cells overexpressing Bcl-2 and Bcl-xL |
| P | !Avermectin B1 | | | | X | antiworm/insecticide |
| P | Azaguanine-8 | X | X | | X | purine analog |
| S | BENZALKONIUM CHLORIDE | X | X | | | cationic detergent; v common antiseptic and preservative |
| P | +Benzethonium chloride | X | X | | | topical antimicrobial used in cosmetics as preservative |
| S | +BENZALKONIUM CHLORIDE | X | X | | | |
| S | !BEPRIDIL HYDROCHLORIDE | X | X | | X | nonselective Ca channel blocker used for treatment of chronic angina pectoris; alters potential dep and receptor-operated Ca channels and inhibits fast Na inward currents |

TABLE 16-continued

| Library | Name | Repeated | NB hit only | NB + FS hit | IC50 test? | target/mechanism |
|---|---|---|---|---|---|---|
| S | beta-PELTATIN | X | X | | X | extracted from Mayapple rhizome (like podophyllotoxin); some evidence of in vitro anti-tumor f/x but vague |
| L | Brefeldin A from Penicillium brefeldianum | X | | X | | fungal metabolite that disrupts Golgi structure and function |
| L | Calmidazolium chloride | X | | X | | Potent inhibitor of calmodulin activation of phosphodiesterase; strongly inhibits calmodulin-dependent Ca2+-ATPase |
| S | CAMPTOTHECIN | X | X | | | |
| L | Camptothecin (S.+) | X | X | | | topo 1 inh |
| P | Camptothecine (S.+) | X | X | | X | |
| P | Cephaeline dihydrochloride heptahydrate | X | | X | | ipecac alkaloid |
| S | CETRIMONIUM BROMIDE | X | | X | | cationic detergent; quaternary ammonium compound used in hair conditioner and as a antimicrobial; tested as a lavage during colon resections . . . no benefit and potentially toxic |
| S | CETYLPYRIDINIUM CHLORIDE | X | X | | | active ingredient in Scope; antiseptic used in oral rinses |
| L | CGP-74514A hydrochloride | X | X | | X | Cdk1 inh |
| L | Chelerythrine chloride | X | X | | X | PKC inhibitor; affects translocation of PKC from cytosol to plasma membrane |
| S | CHELIDONINE (+) | X | X | | | G2/M arrest associated with increased cycB1 levels, cdc2 activity and SAPK/JNK activity; weak tubulin interaction; induced apoptosis at 1 uM in Jurkat cells |
| S | CHOLESTAN-3beta.5alpha.6beta-TRIOL | X | X | | X | Cholesterol oxidation product; cytotoxic due to oxidative stress or cytoskeleton disruption |
| P | Ciclopirox ethanolamine | X | X | | | topical antifungal, anti-inflammatory |
| S | CICLOPIROX OLAMINE | X | X | | X | |
| P | Clofazimine | X | X | | X | leprosy treatment; anti-inflammatory f/x; disrupts cc by binding DNA, may bind K+ transporters |
| S | COLCHICEINE | X | | X | | metabolite of colchicine; less toxic to hepatocytes; less binding to tubulin but presumably has similar modeof action |
| L | Colchicine | X | X | | | binds tubulin/blocks mitosis by preventing spindle formation; bioactive doses would be toxic |
| P | Colchicine | X | X | | X | |
| S | COLCHICINE | | | | | |
| S | #CONVALLATOXIN | X | X | | X | derived from lily of the valley; digitalis-like action |
| S | CRASSIN ACETATE | X | X | | X | antineoplastic vs P388 leukemia and HT29 colon cancer cells in vitro; extracted from marine invertebrates |
| S | CRINAMINE | X | X | | X | |
| P | Cycloheximide | X | X | | | protein synthesis inh |

TABLE 16-continued

| Library | Name | Repeated | NB hit only | NB + FS hit | IC50 test? | target/mechanism |
|---|---|---|---|---|---|---|
| S | CYCLOHEXIMIDE | | | | | |
| S | CYMARIN | | | X | | |
| S | CYTARABINE | X | | | | Ara-C; DNA damage, S-phase block; inh DNA/RNA pol |
| L | Cytosine-1-beta-D-arabinofuranoside hydrochloride | X | X | | | Ara-C; selective inh of DNA synthesis |
| S | DACTINOMYCIN | X | | X | | |
| P | Daunorubicin hydrochloride | X | | X | | DNA intercalator; neuroblastoma treatment |
| S | DEOXYSAPPANONE B 7.3'-DIMETHYL ETHER | X | | X | | flavanoid derived from Caesalpinia sappan tree; Chinese med treatment for tumor, diarrhea; aldose reductase inhibitor?; one study suggesting activity vs head and neck cancer cell line |
| L | *Dequalinium analog. C-14 linker* | X | X | | X | Protein kinase C-alpha (PKC-alpha) inhibitor |
| P | !Dequalinium dichloride | X | X | | X | Selective blocker of apamin-sensitive K+ channels |
| L | !Dequalinium dichloride | X | X | | X | Member of delocalized lipophilic cations (DLCs), a family of compounds that accumulate in mitochondria driven by the negative transmembrane potential; inhibitor of NADH-ubiquinone reductase; A novel mitochondria delivery system is based on dequalinium. This DLC forms liposome-like aggregates termed 'DQAsomes'. DQAsomes are being tested as mitochondria drug delivery systems for small molecules such as paclitaxel |
| P | #Digitoxigenin | | X | X | | Digitalis derivative; blocks Na+/K+ pump |
| S | #DIGITOXIN | | | | | |
| P | #Digoxigenin | X | X | | | Digitalis derivative; blocks Na+/K+ pump |
| P | #Digoxin | X | | X | X | Digitalis derivative; blocks Na+/K+ pump |
| S | #DIGOXIN | X | | X | | |
| S | DIHYDROGAMBOGIC ACID | X | | X | X | |
| L | !Dihydroouabain | X | | X | X | Na+/K+ pump inhibitor |
| L | *Diphenyleneiodonium chloride* | X | X | | X | eNOS inh (endothelial NOS) |
| S | DISULFIRAM | X | X | | | |
| P | Disulfiram | X | | X | | antabuse, rxn with alcohol use |
| L | *DL-Stearoylcarnitine chloride* | X | X | | X | PKC inh |
| P | Doxorubicin hydrochloride | X | X | | | DNA synthesis inh; stabilizes topo II complex after strand cleavage |
| S | EMETINE | X | | X | | |
| P | Emetine dihydrochloride | X | | X | | ipecac alkaloid; inh protein synthesis by blocking Rb movement on mRNA; inhibit DNA replication in S phase |
| L | Emetine dihydrochloride hydrate | X | | X | | Apoptosis inducer; RNA-Protein translation inhibitor |

TABLE 16-continued

| Library | Name | Repeated | NB hit only | NB + FS hit | IC50 test? | target/mechanism |
|---|---|---|---|---|---|---|
| S | ERYSOLIN | X | X | | X | organic isothiocyanate found in cruciferous veggies; increases accumulation of chemo drugs in PANC-1, MCF-7, NCI-H460 cell lines |
| P | Etoposide | X | X | | X | topo II inh |
| L | Etoposide | X | X | | | |
| P | Fosfosal | | | | | salicylic acid derivative/ anti-inflammatory |
| S | *GAMBOGIC ACID* | X | X | | X | principle pigment of gambage resin (bright orange), caspase activator (not well characterized); growth/ tumor inhibitory vs HeLa, HEL, gastic cancer, lung carcinoma cell lines |
| S | GENTIAN VIOLET | X | | X | | |
| L | Idarubicin | X | X | | X | antineoplastic, DNA metabolism |
| S | !IMIDACLOPRIDE | X | X | | X | a4b2 nAChR agonist; activates ERK pathway; insecticide |
| S | JUGLONE | X | | X | X | Pin1 inh; alkylates thioredoxin reductase; PI3K inh?; inhibits growth of HCT-15, HeLa, HL60 cell lines |
| P | Kaempferol | | | | | antioxidant/flavenoid |
| P | #Lanatoside C | X | | X | | Digitalis derivative; blocks Na+/K+ pump |
| S | #LANATOSIDE C | X | | X | | |
| S | LIMONIN | X | X | | X | isolated from citrus fruit seeds; inhibits HIV1 protease activity; antinociceptive, inhibits MCF7 growth but not other cancer cell lines |
| L | *Loratadine | X | X | | X | H1 Histamine R antagonist |
| S | LYCORINE | X | | X | | |
| P | +Mebendazole | | | | | anthelmintic; blocks glucose/nutrient uptake in adult worm intestine; reported to be a mitotic spindle poison (resulting in chromosomal nondisjunction) |
| S | MECHLORETHAMINE | X | X | | X | mustard gas derivative; polyfunctional alkylating agent = DNA breaks and crosslinks; non cc phase specific |
| S | *MECLIZINE HYDROCHLORIDE | X | X | | X | antivert/bonine; motion sickness/vertigo treatment; piperazine class of antihistamines |
| L | Melphalan | | | | | Antineoplastic; forms DNA intrastrand crosslinks by bifunctional alkylation in 5'-GGC sequences; used in NB megatherapy |
| P | Menadione | | | | | vitamin K3 (vitK2 precursor); reacts with -SH/soaks up GSH = high ROS = altered Ca2+ = Ca-dep DNA fragmentation; toxic at high doses so vitK2 currently being used in cancer trials |
| P | +Methiazole | | | | | anthelmintic |
| P | +Methyl benzethonium | X | | X | | topical antimicrobial |

TABLE 16-continued

| Library | Name | Repeated | NB hit only | NB + FS hit | IC50 test? | target/mechanism |
|---|---|---|---|---|---|---|
| S | +METHYLBENZETHONIUM CHLORIDE | X | | X | | |
| L | !MG 624 | X | X | | X | Nicotinic acetylcholine receptor antagonist; selectively inhibits alpha-bungarotoxin sensitive receptors that contain the alpha7 subunit |
| S | MITOMYCIN C | X | | X | X | |
| S | MITOXANTHRONE HYDROCHLORIDE | | | | X | |
| L | Mitoxantrone | X | | X | | topo II inh; used in ALL, breast cancer, non-hodgkin's lymphoma |
| P | Mitoxantrone dihydrochloride | X | | X | | |
| P | Mycophenolic acid | X | X | | X | immunosuppressant; blocks de novo purine biosynthesis |
| S | NERIIFOLIN | | | | | |
| L | #Ouabain | X | | X | | Blocks movement of the H5 and H6 transmembrane domains of Na+-K+ ATPases |
| S | #OUABAIN | X | | X | X | |
| S | +OXYBENDAZOLE | X | X | | X | benzimidazole anthelmintic used in horses and other ruminants |
| S | OXYPHENBUTAZONE | X | | X | | Anti-inflammatory (Tandearil); binds phospholipase A2, human neutrophil elastase |
| P | Paclitaxel | X | X | | X | taxol |
| S | PACLITAXEL | X | X | | | taxol |
| S | PARAROSANILINE PAMOATE | X | | X | X | |
| P | Parthenolide | X | X | | X | feverfew extract; NFkB inh, p53 activ, increased ROS, JNK activ (indep of NFkB and ROS), inh of MAPK/ERK pathway |
| S | PARTHENOLIDE | X | X | | | seems to work best as a chemosensitizer...studies in breast, skin, pancreatic, thoracic cell lines |
| S | PATULIN | X | | X | | |
| S | #PERIPLOCYMARIN | X | | X | X | digoxin relative |
| S | #PERUVOSIDE | X | | X | X | inhibitor of Na+K+-ATPase; cardiac glycoside class |
| S | PHENYLMERCURIC ACETATE | X | | X | | |
| P | Podophyllotoxin | X | X | | X | etoposide precursor/Antineoplastic glucoside; inhibitor of microtubule assembly; G2/M cc arrest |
| L | Podophyllotoxin | X | X | | | |
| S | PODOPHYLLOTOXIN ACETATE | X | | X | | |
| P | !Primaquine diphosphate | X | X | | X | antimalarial/inh of DNA, RNA, protein synthesis/muscarinic AChR inh |
| P | #Proscillaridin A | X | | X | | Na+/K+ ATPase inh; digitalis related |
| P | Puromycin dihydrochloride | X | | X | | protein synthesis inh, premature strand termination |
| S | PUROMYCIN HYDROCHLORIDE | X | | X | | |
| S | PYRITHIONE ZINC | X | | X | X | |
| S | PYRROMYCIN | X | | X | | anthracycline derivative; monosaccharide; induces erythroid diff in K562 |

TABLE 16-continued

| Library | Name | Repeated | NB hit only | NB + FS hit | IC50 test? | target/mechanism |
|---|---|---|---|---|---|---|
| P | +Pyrvinium pamoate | | | | | pinworm treatment; prevents glucose uptake; antitumor activity vs pancreatic cell line in SCID model, see decrease Akt phos |
| L | !Quinacrine dihydrochloride | X | X | | X | Monoamine oxidase (MAO) inhibitor; antimalarial |
| P | !Quinacrine dihydrochloride dihydrate | X | X | | | Antimalarial, causes female sterility |
| S | RETUSOQUINONE | X | | X | | ? |
| P | !Sanguinarine | X | | X | | Inhibitor of Mg2+ and Na+/K+-ATPase; isolated from the leaves and stems of Macleaya cordata and microcarpa |
| L | !Sanguinarine chloride | X | | X | X | |
| S | !SANGUINARINE SULFATE | X | X | | | |
| S | SARMENTOGENIN | X | | X | | |
| P | !Scoulerine | X | X | | X | opium intermediate/alkaloid; a1-adrenoreceptor inh (G-protein coupled R found on PNS sympathetic nerve terminals, CNS postsynaptically; target of catecholamines) |
| P | !Strophanthidin | X | | X | X | blocks Na+/K+ ATPase at high conc; opposite f/x at low dose (Quabain) |
| S | !STROPHANTHIDIN | X | | X | | |
| S | !STROPHANTHIDINIC ACID !LACTONE ACETATE | X | X | | | |
| P | !Strophantine octahydrate | X | | X | | |
| L | Taxol | X | X | | | Antitumor agent; promotes assembly of microtubules and inhibits tubulin disassembly process |
| S | TENIPOSIDE | X | X | | X | common NB treatment; semisynthetic podophyllotoxin derivative related to etoposide; topo II inh; induced single strand DNA breaks; activity in late S and G2 phases |
| P | *Terfenadine | X | | X | X | nonsedating antihistimine off market due to cardiac f/x |
| S | THIMEROSAL | X | | X | | |
| S | THIRAM | | | | | |
| P | Thonzonium bromide | X | | X | | cationic detergent |
| S | TOMATINE | X | | X | X | |
| P | Verteporfin | | | | | photoreactive dye used in treatment of macular generation; anti-angiogenic |
| S | VINBLASTINE SULFATE | X | X | | | |
| L | Vinblastine sulfate salt | X | X | | X | Inhibitor of microtubule assembly |
| L | Vincristine sulfate | X | X | | X | Inhibitor of microtubule assembly |
| | | 132/151 repeated (87%) | | | | |

BOLD: DNA damage/protein synthesis inhibitor/cell cycle block
italics: protein inhibitor/activator
*: antihistamine
: digoxin derivative
+: metabolic f/x
!: ion channel inhibitor/neuro R inhibitor

Example 16

Selected Compounds of Interest

The present example demonstrates the utility of the present invention for providing a composition suitable for the inhibition of NB survival, proliferation, or induction of differentiation, and for the treatment of NB.

Forty-seven (47) compounds were selected based on differential cell toxicity and compound mechanism of action. Forty are novel compounds for the treatment of NB. None of these 40 compounds have been used clinically in NB therapy nor have they been examined in clinical trials. Seven compounds have been previously used for NB treatment (marked with asterisk), and serve as positive controls in the selection and screening process of new chemical entities that may be used in the treatment of NB according the present invention.

TABLE 17

| Compounds of Interest: | NB12 IC50 (nM) | Notes: |
|---|---|---|
| 2.3-Dimethoxy-1.4-naphthoquinone | nd | ROS modulator/Redox cycling agent used to study role of ROS |
| AKLAVINE HYDROCHLORIDE | 778.5 | natural product; anti-infective; related structures have broad activity against NIH tumor lines |
| Amodiaquin dihydrochloride dihydrate | 790 | antimalarial; treatment of CNS degeneration (Alzheimer, MS); 4-aminoquinoline family; narrow therapeutic/toxic window in children; 4-Aminoquinolines depress cardiac muscle, impair cardiac conductivity, and produce vasodilatation with resultant hypotension |
| AMSACRINE HYDROCHLORIDE | 1214 | topo II inh; used in AML; may also be active vs malaria |
| *ANCITABINE HYDROCHLORIDE | 519.7 | cyclocytidine HCl; DNA-synthesis inhibitor (cytosine analog); antileukemic |
| Azaguanine-8 | 331 | purine analog |
| beta-PELTATIN | 1949 | extracted from Mayapple rhizome (like podophyllotoxin); some evidence of in vitro anti-tumor f/x but vague |
| Camptothecine (S.+) | 183.3 | topoisomerase 1 inh |
| CGP-74514A hydrochloride | | Cdk1 inh |
| Chelerythrine chloride | 2553 | PKC inhibitor; affects translocation of PKC from cytosol to plasma membrane |
| CHOLESTAN-3beta.5alpha.6beta-TRIOL | 2410 | Cholesterol oxidation product; cytotoxic due to oxidative stress or cytoskeleton disruption |
| CICLOPIROX OLAMINE | 2048 | topical antifungal, anti-inflammatory via inhibition of 5-lipoxygenase and cyclo-oxygenase; hydroxypyridone family; Loprox |
| Clofazimine | 1417 | leprosy treatment; anti-inflammatory f/x; disrupts cc by binding DNA, may bind K+ transporters |
| Colchicine | 29.3 | binds tubulin/blocks mitosis by preventing spindle formation; bioactive doses would probably be toxic |
| CONVALLATOXIN | 73.17 | derived from lily of the valley; digitalis-like action |
| CRASSIN ACETATE | 1947 | antineoplastic vs P388 leukemia and HT29 colon cancer cells in vitro; cembranolides (14-member ring diterpenoid lactones) derived from Caribbean gorgonians (marine invertebrates) |
| CRINAMINE | 1735 | HIF-1alpha inhibitor; affinity to the serotonin reuptake transport protein |
| Dequalinium analog. C-14 linker | 1112 | Protein kinase C-alpha (PKC-alpha) inhibitor |
| Dequalinium dichloride | 3617 | Selective blocker of apamin-sensitive K+ channels; mitochondria toxicity |
| Digitoxin | nd | Na+/K+ pump inhibitor |
| Digoxigenin | nd | Na+/K+ pump inhibitor |
| Digoxin | 542.2 | Digitalis derivative; blocks Na+/K+ pump |
| DIHYDROGAMBOGIC ACID | 1687 | |
| Dihydroouabain | 1540 | Na+/K+ pump inhibitor |
| ERYSOLIN | 3276 | organic isothiocyanate found in cruciferous veggies; increases accumulation of chemo drugs in PANC-1, MCF-7, NCI-H460 cell lines |
| *Etoposide | 693.7 | topoisomerase II inh |
| GAMBOGIC ACID | 1695 | principle pigment of gambage resin (bright orange); caspase activator (not well characterized); growth/tumor inhibitory vs HeLa, HEL, gastic cancer, lung carcinoma cell lines |
| *Idarubicin | 203.7 | antineoplastic, DNA metabolism |

TABLE 17-continued

| Compounds of Interest: | NB12 IC50 (nM) | Notes: |
|---|---|---|
| MECHLORETHAMINE | 438.2 | mustard gas derivative; polyfunctional alkylating agent = DNA breaks and crosslinks; non cell cycle phase specific |
| MECLIZINE HYDROCHLORIDE | 2537 | "antivert/bonine"; motion sickness/vertigo treatment; piperazine class of antihistamines |
| MG 624 | 848 | Nicotinic acetylcholine receptor antagonist; selectively inhibits alpha-bungarotoxin sensitive receptors that contain the alpha7 subunit |
| MITOXANTHRONE HYDROCHLORIDE | 60.46 | topo II inh; used in ALL, breast cancer, non-hodgkin's lymphoma |
| OUABAIN | 122.6 | Blocks movement of the H5 and H6 transmembrane domains of Na+-K+ ATPases |
| OXYBENDAZOLE | nd | benzimidazole anthelmintic used in horses and other ruminants |
| Paclitaxel | nd | aka taxol; Antitumor agent; promotes assembly of microtubules and inhibits tubulin disassembly process |
| Parthenolide | 2261 | feverfew extract; NFkB inh, p53 activ, increased ROS, JNK activ (indep of NFkB and ROS), inh of MAPK/ERK pathway; seems to work best as a chemosensitizer . . . studies in breast, skin, pancreatic, thoracic cell lines |
| PATULIN | nd | polyketide lactone, produced by certain fungal species of *Penicillium, Aspergillus* and *Byssochlamys* growing on fruit, including apples, pears, grapes; crosslinks DNA, causes p38 and JNK phosphorylation in HEK cells |
| PERIPLOCYMARIN | 2703 | digoxin relative |
| PERUVOSIDE | 222.5 | inhibitor of Na+K+-ATPase; cardiac glycoside class |
| *Podophyllotoxin | 135 | etoposide precursor/Antineoplastic glucoside; inhibitor of microtubule assembly; G2/M cc arrest |
| Primaquine diphosphate | nd | antimalarial/inh of DNA, RNA, protein synthesis/muscarinic AChR inh |
| Quinacrine dihydrochloride | 2556 | Monoamine oxidase (MAO) inhibitor; antimalarial |
| Sanguinarine chloride | 1795 | Inhibitor of Mg2+ and Na+/K+-ATPase; isolated from the leaves and stems of *Macleaya cordata* and *microcarpa* |
| *TENIPOSIDE | 705.5 | common NB treatment; semisynthetic podophyllotoxin derivative related to etoposide; topo II inh; induced single strand DNA breaks; activity in late S and G2 phases |
| TOMATINE | nd | alkaloid found in leaves of tomato and unripe fruit; tetrasaccharide tomato glycoalkaloid alpha-tomatine, trisaccharide beta(1)-tomatine, disaccharide gamma-tomatine, monosaccharide delta-tomatine, and their common aglycon tomatidine; inhibit the growth of human colon (HT29) and liver (HepG2) cancer cells |
| *Vinblastine sulfate salt | 113 | Inhibitor of microtubule assembly |
| *Vincristine sulfate | 61.95 | Inhibitor of microtubule assembly |

Tables 7, 11, 14, and 17 identify parthenolide, a compound that specifically targets NB TICs, as a compound previously identified to target human acute myelogenous leukemia stem and progenitor cells (55).

Example 17

Secondary Screening

In vitro testing of compounds of interest will be conducted on NB TICs from different patients using a methylcellulose assay (or 96 well liquid culture) with drug dose response curve to assess stem cell killing, proliferation, or differentiation, and conducted on the following cell lines:

NB12, NB10 (GN), NB19, NB25, NB05 (TICs or primary sphere-forming cells from NB patients)

FS90, FS105, FS99, FS107, FS81 (pediatric human SKPs)

KCNR (human established NB cell line)

In addition, a combination treatment with the most promising compounds and currently-used chemotherapeutic agents will be conducted determine if compounds of interest will act synergistically with the currently-used compounds to induce cell death, stop cell proliferation, or induce differentiation into neural cell types.

Chemical Optimization

Structurally similar compounds to those identified above will be tested to determine if they will induce TIC or NB death at lower effective doses.

Animal Models

TICs will be injected orthotopically into the mouse adrenal fat pad (the site of the majority of human NB), tumors allowed to initiate for seven days, mice injected with a range of doses of compounds, and suppression of tumor size determined by histological analysis and immunohistochemistry for TH and NB84, for tumor cell death by the expression of cell death markers cleaved caspase and by TUNEL assay, cessation of cell proliferation by anti-MIB-1 immunohistochemistry, and inhibition of metastasis by histological and immunohistochemical examination of liver, bone marrow, and kidney by anti-NB84 and tyrosine hydroxylase.

TICs will be injected into the mouse inguineal fat pad, tumors allowed to initiate for seven days, and mice injected with a range of doses of compounds, tumors allowed to initiate for seven days, mice injected with a range of doses of compounds, and suppression of tumor size determined by histological analysis and immunohistochemistry for TH and NB84, for tumor cell death by the expression of cell death markers cleaved caspase and by TUNEL assay, cessation of cell proliferation by anti-MIB-1 immunohistochemistry, and inhibition of metastasis by histological and immunohistochemical examination of liver, bone marrow, and kidney by anti-NB84 and TH.

TICs will be injected into mice that have NB as a result of expression of the MYCN oncogene (31), tumors allowed to initiate for seven days, and mice injected with a range of doses of compounds, tumors allowed to initiate for seven days, mice injected with a range of doses of compounds, and suppression of tumor size determined by histological analysis and immunohistochemistry for TH and NB84, for tumor cell death by the expression of cell death markers cleaved caspase and by TUNEL assay, cessation of cell proliferation by anti-MIB-1 immunohistochemistry, and inhibition of metastasis by histological and immunohistochemical examination of liver, bone marrow, and kidney by anti-NB84 and TH.

Example 18

Tumor Initiating Cells in Childhood Neuroblastoma

The present example demonstrates the utility of the present invention for providing a method for providing an enriched population of human NB TICs, and in particular, from a child having NB. In addition, the present example demonstrates the utility of The present example demonstrates the utility of the present invention for providing present invention for providing a method by which therapeutic agents suitable for the treatment of a human, particularly a child, having NB may be selected.

Materials and Methods:

Primary Culture of Tumor Spheres from Tumors and Bone Marrow Aspirates

Tumor samples and bone marrow aspirates were obtained from consented patients, as approved by the Hospital for Sick Children's Research Ethics Board. Bone marrow aspirates were filtered through a 40-μm cell strainer and tumor cells collected by inverting and washing the filter with Hank's balanced salt solution (HBSS; Invitrogen, Carlsbad, Calif.), while tumor samples were collected and cut into 2-3 mm$^2$ pieces. All samples were then enzymatically dissociated with LIBERASE® Blendzyme 1 (an enzyme blend) (0.62 Wunsch U/ml; Roche, Indianapolis, Ind.) in HBSS for 15-45 minutes at 37° C. and 10% Fetal Bovine Serum (FBS; HyClone, Logan, Utah) added to inhibit enzyme activity. Tumor cells were then mechanically dissociated in medium and the suspension poured through a 40 μm cell strainer. Dissociated cells were pelleted and resuspended in Dulbecco's modified Eagle's medium [DMEM]-F12 (3:1) (Invitrogen) containing 1% penicillin/streptomycin, 2% B27 supplement (Gibco, Carlsbad, Calif.), 40 ng/ml FGF and 20 ng/ml EGF (both from Collaborative Research, Bedford, Mass.), from herein referred to as proliferation media, and cultured in 25 cm$^2$ flasks (Falcon) in a 37° C., 5% $CO_2$ tissue-culture incubator. Cells were fed fresh proliferation medium weekly.

Tumor spheres were passaged by mechanical dissociation and split 1:6 with 50% fresh proliferation medium and 50% conditioned medium from the initial flask. Human SKPs, which are of neural crest origin, were used as normal comparative cells in our experiments, and were isolated and cultured according to protocols established in the laboratory (18).

Tumor Sphere Self-Renewal Assay and Growth Curves

Self-renewal is a fundamental feature of stem cells, either of normal or tumor origin, and can be tested by serial passage (58, 14). The self-renewal capacity of tumor spheres was assessed in the present example using a semi-solid methylcellulose medium. After primary spheres formed, spheres were mechanically dissociated into single cells and plated into uncoated 24-well tissue culture plates (Falcon) containing 1 ml of 0.9% methylcellulose (Sigma, St Louis, Mo.), 10% conditioned medium and growth factors as described for the proliferation medium. Final plating densities ranged from 25 000 cells/ml to 100 cells/ml. Cultures were fed 150 μl proliferation media twice weekly for 21 days, when the number of spheres for each plating density was counted. Self-renewal capacity was calculated as the percentage of single cells that were able to form spheres.

Growth curves were established by mechanically dissociating passaged tumor spheres, plating $8.3 \times 10^4$ single cells in 12.5 cm$^2$ flasks and performing cells counts 3, 5 and 7 days after plating. The mean cell count of 3 independent experiments was graphed and SEM calculated.

Neurogenic Differentiation of Tumor Spheres

Five to ten tumor spheres were plated onto poly-D-lysine/laminin-coated 8-well chamber slides (Nalge Nunc, Rochester, N.Y.) expanded in medium containing DMEM-F12 (3:1), 10 ng/ml FGF and 15% FBS for 5-10 days and then differentiated in Neurobasal medium (Invitrogen) containing 2% B27 supplement, 1% FBS, 1% N2 supplement (Gibco), 16 μg/ml NGF (Cedarlane, Hornby, ON), and 8 ng/μl NT3 (Peprotech, Rocky Hill, N.J.) for a further 14 days. Half media was replaced every second day throughout the assay.

Immunocytochemistry and Quantification

Immunocytochemical analysis of cells was performed using coated glass slides and the Shandon CYTOSPIN® system (a cytocentrifuuge) (Thermo, Waltham, Mass.) for tumor spheres or cells differentiated on chamber slides as described (16; 18). The following primary antibodies were used: NB84 monoclonal (1:50; Novocastra, Newcastle upon Tyne, UK); anti-THpolyclonal (1:150; Chemicon, Temecula, Calif.); anti-βIII-tubulin monoclonal (1:500; Tuj1 clone; Covance, Berkeley, Calif.); anti-neurofilament-M polyclonal (NFM) (1:200; Chemicon); s100β monoclonal (1:1000; Sigma); anti-GFAP polyclonal (1:200; DAKO, Copenhagen, Denmark); Galactocerebroside C (GalC) polyclonal (1:200;

Chemicon); anti-Nestin monoclonal (1:400; Chemicon); anti-Nestin polyclonal (1:400, Chemicon); anti-fibronectin polyclonal (1:400; Sigma). The following secondary antibodies were used: Alexa 488-conjugated goat-anti-mouse (1:1000) and Alexa 555-conjugated goat-anti-rabbit (1:1000), both were from Molecular Probes (Eugene, Oreg.).

Differentiation was quantified by calculating the percentage of spheres that formed either neuronal networks or neurons. Data was pooled for good (stages 1-3 and 4S) and poor prognosis (stage 4) NB tumors and the overall mean and SEM calculated.

Orthotopic Assay of in vivo Tumorigenicity and Immunohistochemistry

Four to 5 week-old female SCID/Beige mice (Taconic; Hudson, N.Y.) were housed in pathogen-free conditions and cared for in accordance with the National Institutes of Health Animal Care and Use Committee. Animals were acclimatized for 1 week prior to surgery. Surgical sites were prepared by shaving and cleansing with Betadine scrub solution and 70% sterile alcohol. Anesthesia was induced using 5% isoflurane/1.5 L oxygen and maintained 3% isoflurane/1.5 L oxygen inhalation. In vitro passaged primary NB cells (passages 4-5) were harvested and brought to final cell densities of $3 \times 10^6$, $3 \times 10^5$ or $3 \times 10^3$/ml in HBSS for both orthotopic adrenal and heterotopic subcutaneous injections. Cells were kept at 4° C. until ready for injection and mixed 1:3 with basement membrane extract (Trevigen, Gaithersburg, Md.) just prior to injection (final cell doses $10^5$, $10^4$ and $10^2$). Orthotopic and heterotopic injections were performed as previously described (28). Animals were monitored thrice weekly for evidence of tumor formation and associated morbidity.

All mice that were sacrificed underwent complete necropsy examination and tissues fixed in 10% formalin for 24 hours prior to paraffin embedding and staining with hematoxylin and eosin (H&E) or a small piece of tumor collected and re-implanted to follow secondary tumor formation. The endpoints evaluated were the percent tumor-take that is the percentage of animals that developed primary tumors and tumor latency, which is the time from tumor cell injection to the detection of a primary tumor.

The following antibodies were used for immunohistochemical analysis of orthotopic adrenal tumors: NB84 monoclonal (1:20), anti-TH polyclonal (1:150), and anti-nestin polyclonal (1:200). Sections were incubated with polyclonal swine anti-goat, mouse, rabbit biotinylated secondary antibody (1:500) (DAKO) and then tertiary staining was performed with peroxidase-conjugated strepavadin (1:500) (DAKO). Staining was visualized using 3, 3'-diaminobenzidine (DAB) as a chromogen and counterstained with hematoxylin.

Flow Cytometry and Fluorescence Activated Cell Sorting

Cultured primary NB cells were collected, washed twice in HBSS and resuspended as single cells in buffer (0.5% bovine serum albumin in PBS). If unconjugated primary antibodies were used, cells were initially blocked in human IgG (Jackson ImmunoResearch, West Grove, Pa.) and then incubated in primary antibody for 30 minutes at 4° C. If an unconjugated primary antibody was used, cells were pelleted, resuspended in buffer and incubated with Alexa Fluor 488-conjugated goat anti-mouse secondary antibody (Molecular Probes, Invitrogen) for 20 minutes at 4° C. Cells were then washed twice in buffer and resuspended and fixed in buffer/2% paraformaldehyde. Approximately $10^5$ cells were stained and analyzed on a Becton Dickinson FACSCalibur 4-color analyzer.

Monoclonal antibodies against human CD133/1 (biotin) and CD271 (FITC) were purchased from Miltenyi Biotech (Bergisch Gladbach, Germany); the monoclonal antibody against human CD56 (PE) was purchased from DAKO; the monoclonal antibody against human NB84 (FITC) was purchased from Novocastra; the monoclonal antibodies against human CD24 (PE), CD29 (PECy5), CD81 (APC), CD34, CD44, CD45, CD20 and CD117, and rat monoclonal antibody CD49f (PE) were purchased from BD biosciences (Oakville, ON). Isotype matched mouse or rat purified, PE- or FITC-conjugated antibodies (BD Biosciences) were used as controls.

Fluorescence-activated cell sorting (FACS) was done on a DAKO CYTOMATION® MOFLO® 9-color cell sorter. Sorting was performed on double stained cells. Cells were stained with purified monoclonal CD34 and Alexa Fluor 488-conjugated goat anti-mouse secondary antibody followed by PE-conjugated monoclonal CD24 antibody.

Results:

Neuroblastoma Cells from Tumors and Bone Marrow Aspirates Form Non-adherent Spheres When Grown in Serum-Free Conditions:

Neuroblastoma cells from tumors and bone marrow aspirates form non-adherent spheres when grown in serum-free conditions.

Seventeen tumor samples were used in the study including 6 high stage (stage 4) and 7 low stage NB tumors and 4 ganglioneuroma tumors, a benign cousin of NB (See Summary of Patient Population Table).

Summary of Patient Population Table

| PATIENT # | SEX | AGE AT DX. | DX. | SAMPLE TYPE |
|---|---|---|---|---|
| 1 | F | >18 m | Stage 4 neuroblastoma | Relapse bone marrow |
| 2 | F | >18 m | Ganglioneuroblastoma | Tumour |
| 3 | M | >18 m | Stage 4 neuroblastoma | Relapse bone marrow |
| 4 | F | >18 m | Ganglioneuroma | Tumour |
| 5 | F | >18 m | Stage 4 neuroblastoma | Relapse bone marrow |
| 6 | M | >18 m | Stage 1 neuroblastoma | Tumor |
| 7 | F | <18 m | Stage 1 neuroblastoma | Tumor |
| 8 | F | >18 m | Ganglioneuroma | Tumor |
| 9 (matched to 13) | F | >18 m | Stage 1 neuroblastoma | Bone marrow |
| 10 | M | >18 m | Ganglioneuroma | Bone marrow |
| 11 | F | >18 m | Stage 2 neuroblastoma | Tumor |
| 12 | M | >18 m | Stage 4 neuroblastoma | Tumor |
| 13 (matched to 9) | F | >18 m | Stage 1 neuroblastoma | Tumor |
| 14 | M | <18 m | Stage 1/4S neuroblastoma | Metastasis |
| 15 | M | >18 m | Stage 4 neuroblastoma | Relapse bone marrow |

| PATIENT # | SEX | AGE AT DX. | DX. | SAMPLE TYPE |
|---|---|---|---|---|
| 16 | M | >18 m | Ganglioneuroma | Tumor |
| 17* | F | <18 m | Stage 4 neuroblastoma | Bone marrow |

*borderline MYCN-amplified, patient died.

A serum-free growth medium was used to isolate a putative TIC from the acutely dissociated tumor cells. Serum free growth medium favors stem cell growth (16, 18). Within 1-7 weeks (median time 2 weeks), a primary sphere formation was observed in the cultures as previously described (56). Samples that remained as single cells following acute dissociation and several weeks of culture were excluded from this study. These samples included many low-grade (stage 1 and 4S) and some heavily treated NB tumor samples.

Figure 5A:
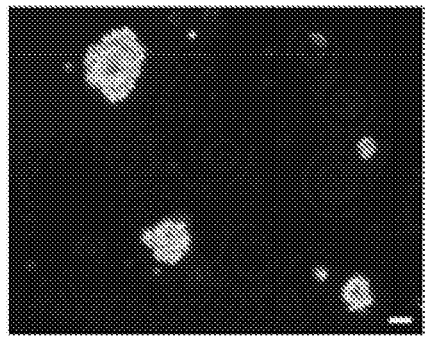
FIG. 5A-5F, according to some aspects of the invention, demonstrates the phenotype of cultured primary NB tumors of different disease phenotypes grown in serum-free culture conditions containing FGF and EGF. Sphere-like clusters formed in the majority of tumor phenotypes following acute dissociation. Following passaging, high-grade tumor spheres from tumors (5A) and bone marrow aspirates (5B) were capable of reforming and growing as spheres, with the exception of a single high-grade tumor sample which acquired adherent growth characteristics upon passaging (5C). Tumors with good prognosis including ganglioneuroma tumors, a benign cousin of NB (5D), and low-grade NB tumors (5E) acquired adherent growth characteristics upon passaging. Scale represents 100 µm. (5F) Undifferentiated primary tumor spheres from all NB phenotypes were immunostained for characteristic clinical markers of NB (NB84 and TH) and the characteristic SKPs stem cell markers fibronectin and nestin. Scale represents 50 µm.
Figure 5B:
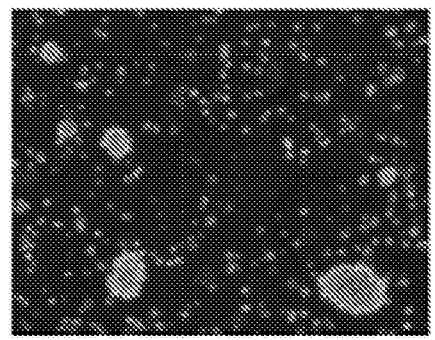
Figure 5C:
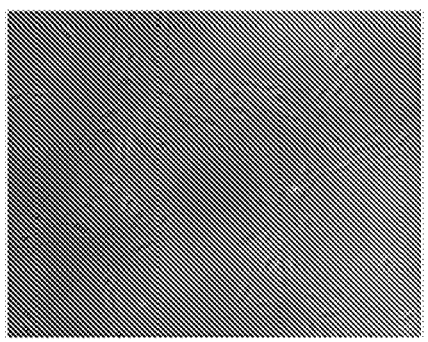
Figure 5D:
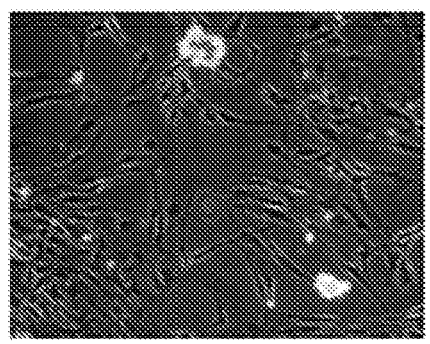
Figure 5E:
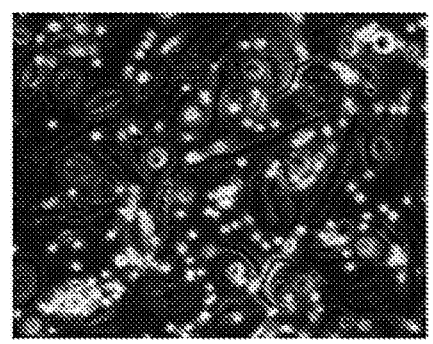

Upon passaging, the majority of primary spheres from high-grade tumors (FIG. 5A) and bone marrow samples (FIG. 5B) formed secondary spheres. However primary ganglioneuroma tumor spheres (FIG. 5D) and primary tumor spheres from low-grade NB samples (FIG. 5E) tended to form adherent cultures when passaged. A single high-grade NB tumor sample became adherent when primary tumor spheres were passaged (FIG. 5C).

Figure 5F:
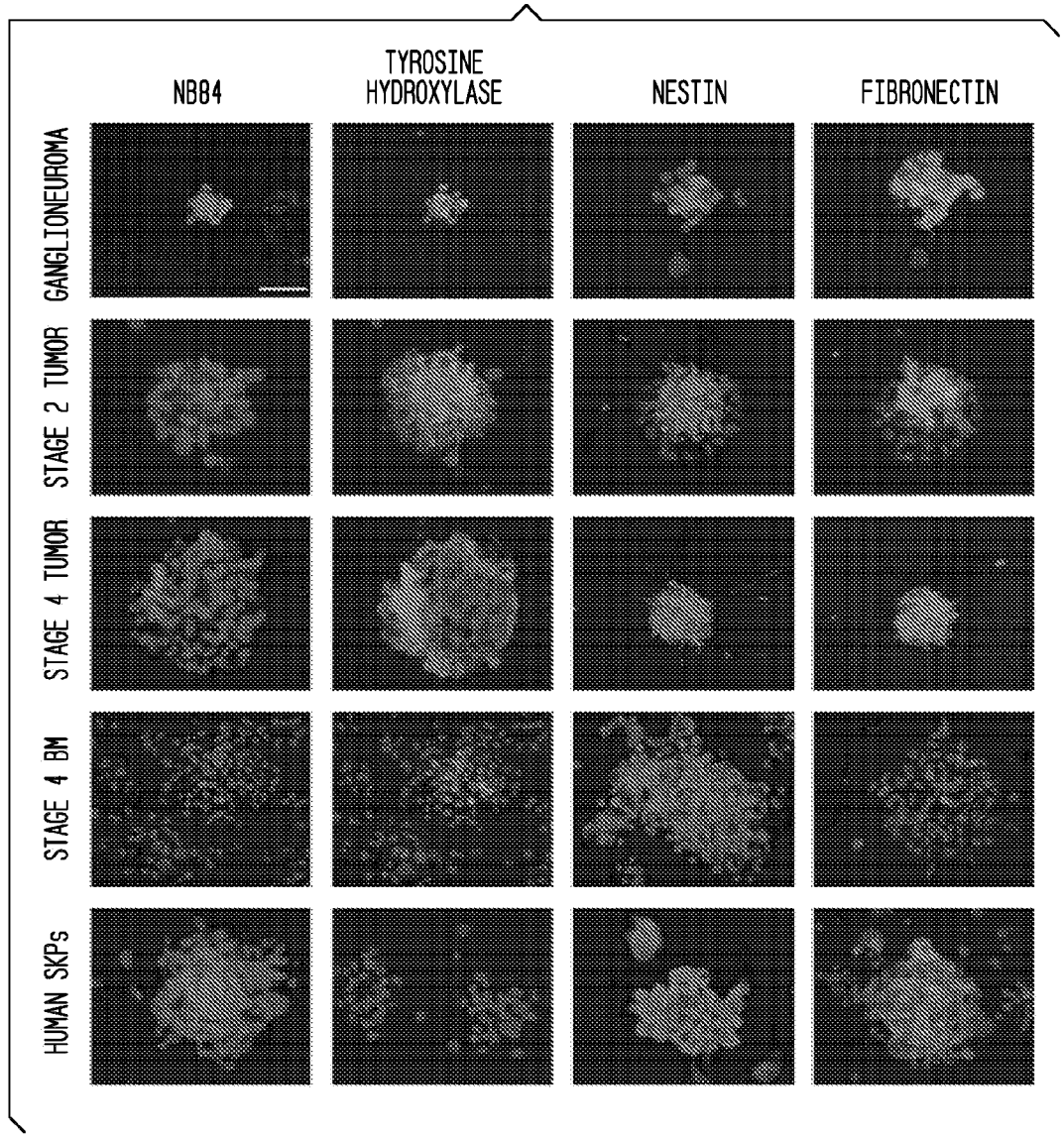

To characterize and aid preliminary identification of the primary tumor spheres grown in serum-free media, clinically recognized standard neuroblastic markers NB84 and TH were used, and the characteristic SKPs progenitor cell markers fibronectin and nestin were used as identifiers of neuroblastic progenitor origin prior to passaging and undertaking further characterization assays (FIG. 5F).

Low-grade Tumor Neuroblastoma Spheres Exhibit Limited Potential for Self-renewal.

Figure 6A:
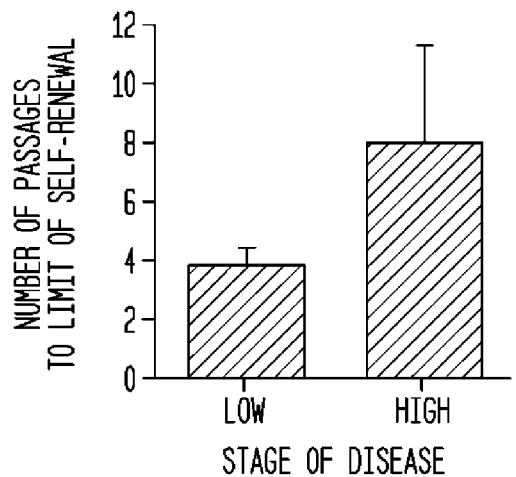

The self-renewal capacity of primary tumor spheres was evaluated by mechanical dissociation of the spheres and plating serial dilutions of cells in semi-solid methylcellulose down to 100 cells/ml. All tumor sample that formed primary tumor spheres in liquid culture were tested in this manner. Tumor spheres from all NB phenotypes, ganglioneuroma tumors and control SKPs formed secondary tumor spheres in methylcellulose. Secondary tumor spheres and SKPs spheres were dissociated and re-plated in methylcellulose until sphere-forming cell populations were depleted. Secondary spheres from low-grade NB and ganglioneuroma tumors formed tumor spheres 0-6 more times (average 3.91), high-grade NB samples formed tumor spheres 3-21 more times (average 8.00) when passaged in methylcellulose (FIG. 6A), and SKPs formed subsequent spheres 1-4 more times.

Figure 6B:
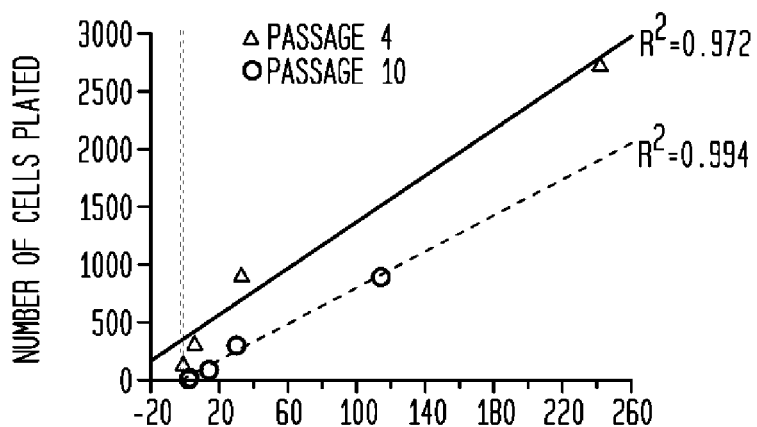
Figure 6C:
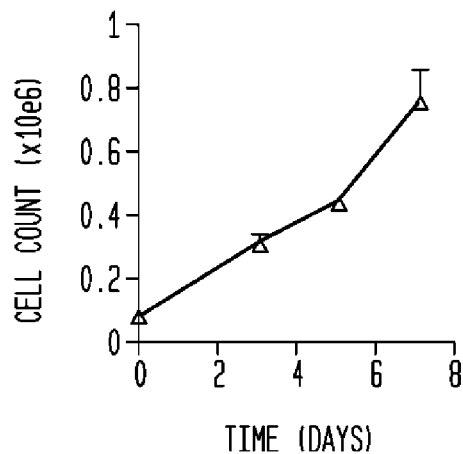

A minimum of three plating densities in the dilution series were counted to determine the average self-renewal for each passage. Linear regression analysis of plating densities showed that the number of resultant spheres was proportional to the number of single cells plated, and did not alter with passaging (FIG. 6B). Growth curves were performed on high-grade tumor spheres showing high growth rates in cultured primary tumors cells (patient 5, passage 7) (FIG. 6C).

The morphology of secondary and subsequent tumor spheres was identical to that of primary spheres. Cells retained their expression of the NB markers NB84 and TH with passaging (FIG. 6D). All tumors studied contained a sub-population of cells that had the capacity to self-renew, however reflecting the clinical aggressiveness of the tumor phenotypes, aggressive NB tumors had increased potential to self-renew with three primary lines from high-grade NB tumor samples continuing to grow and expand extensively.

High-grade Tumor Spheres Exhibit Limited Differentiation Potential Under Neurogenic Conditions Neuroblastoma is a tumor resembling tissues derived from the embryonic neural crest; therefore conditions were used to differentiate SKPs, a normal neural crest-derived human precursor cell, to test the multi-potency of the primary tumor spheres isolated as described herein. (18). After differentiation in neurogenic conditions for two weeks, immunocytochemistry was performed on the differentiated tumor spheres using dual sympathetic neuronal markers (TH, βIII-tubulin, NFM and nestin) or dual markers of glial cells (s100β, GFAP, GalC) to confirm identity of arising cell types. Differentiated cells from both low and high-grade NB tumor spheres retained expression of the NB marker, NB84 and the catecholamine biosynthetic pathway marker, a unique feature of NB, TH with differentiation (FIG. 7A).

Ganglioneuroma tumor spheres and tumor spheres from all NB tumor phenotypes were capable of differentiating into neuronal lineages expressing nestin and βIII-tubulin, neuronal lineage marker commonly observed in peripheral neurons (FIG. 7B) (16; 17:18). The neurogenic conditions under which the tumor spheres were differentiated were not designed to promote differentiation of cells along glial lineages. However rare, spontaneous Schwann-like cells were observed that immunostained with the glial lineage markers s100β, GFAP and GalC, and showed an appropriate phenotype in high-grade NB tumor spheres. Schwann-like cells were not observed in tumor spheres from low-grade NB or ganglioneuroma patients.

Differentiation assays were performed on whole tumor spheres under neuronal conditions and differentiation potential was determined by calculating the percentage of tumor spheres that gave rise to TH, βIII-tubulin, NFM or nestin-positive neurons, either as individual neurons or large neuronal networks. High-grade NB tumor spheres (n=5) showed limited differentiation potential when compared to low-grade tumor spheres (n=5), specifically in their ability to form neuronal networks (FIG. 7C). Ganglioneuroma tumor spheres (n=4) showed similar overall differentiation potential (mean±SEM) (34.97±19.85%) to low-grade NB spheres (47.33±19.63%), but similarly low potential for forming neuronal networks (2.27±2.27%) as observed in high-grade NB tumor spheres (1.45±1.45%). Tumor spheres derived from the bone marrow of 1 ganglioneuroma and 2 high-grade NB patients failed to differentiate under any conditions (patients 5, 10 and 15).

Bone Marrow-derived Tumor Spheres are a Naturally Enriched Source of Tumor-initiating Cells In vivo assays have become the standard for evaluating both tumor propagation and self-renewal (60). An orthotopic adrenal model for assessing tumor propagation was used with these cells in mice since NB tumors most frequently arise in the adrenal medulla.

Between $10^2$ and $10^5$ dissociated high-grade NB tumor sphere cells were injected into the adrenal fat pads of immune-compromised mice and waited until palpable tumors or tumor-associated morbidity was observed. Micro-tumors were observed in several animals injected with $10^2$ cells within 3 weeks of injection by planned sacrifice and observed much larger tumors when a greater cell number was used (FIG. 8A). Furthermore, these tumors contained cells resembling immature neuroblasts with small refractile cell bodies and a high nuclear to cytoplasmic ratio and stained positive for the clinical NB markers NB84, TH, and the stem cell marker nestin (arrow heads, FIG. 8A). High-grade NB tumor sphere cells metastasized to distant sites including the lung, liver, spleen and contralateral adrenal and kidney and invaded local organs (arrow heads, FIG. 8B), similar to tumor behavior in children. Time to morbidity was shorter with higher cell doses (FIG. 8C). The percentage of animals with evidence of tumors, and similarly those with distant metastases increased according to cell dose (FIGS. 8D and 8E, respectively) the animals received. Tumors and metastases were not observed when $10^2$ cells were injected heterotopically into immune-compromised mice.

A small piece of in vivo tumor was taken at sacrifice and re-implanted into immune-compromised mice to follow secondary tumor formation of these cells. Subsequent tumor formation was observed in two independent high-grade NB tumor spheres, suggesting long term self-renewal potential of high-grade NB tumor spheres exists both in vitro and in vivo.

Tumor-initiating Ability of High-grade Tumor Spheres is Highly Enriched in the CD24$^+$/CD34$^+$ Fraction of High-grade Neuroblastoma Tumor Spheres.

Figure 9C:
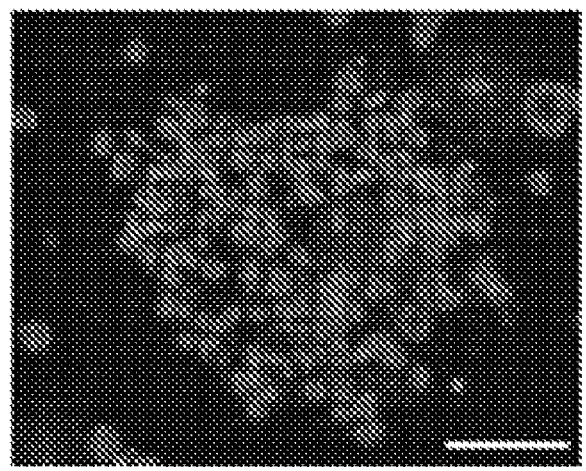
Figure 9E:
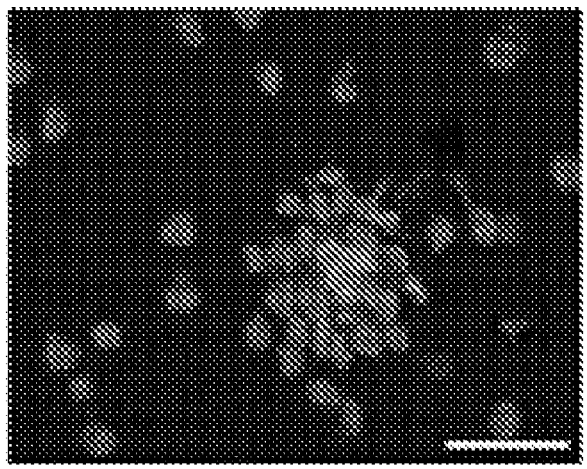

Cells were negative for the previously published brain TIC marker CD133/1 (56) (FIG. 9A), and highly positive for the melanoma tumor-initiating enrichment marker CD20 (61) the clinical NB marker NB84 (FIG. 9A) and CD271/p75 (FIG. 9A), so were not used as candidate unique identifiers in NB. The presence of a small fraction of CD24$^+$ and CD34$^+$ cells was observed in our high-grade NB tumor spheres derived from bone marrow aspirates (patients 5 and 14) (FIGS. 9B and 9D, respectively), that were otherwise absent in NB cell lines and ganglioneuroma (patient 4) tumor spheres. Further, bone marrow-derived high-grade NB tumor spheres were immunocytochemically stained for CD24 and CD34 confirming that a few cells within the tumor sphere that stained positive for our potential markers (FIGS. 9C and 9E, respectively).

The enrichment capacity of these markers was examined for tumor formation by orthotopic injection of each population of a CD24$^+$/CD34$^+$ double sort (total, CD24$^-$/CD34$^-$, CD24$^+$/CD34$^-$, CD24$^-$/CD34$^+$, CD24$^+$/CD34$^+$ cell populations). While all cellular fractions formed tumors in immune-compromised mice, CD24$^+$/CD34$^+$ tumors formed in half the time of all other cellular fractions (mean±SEM) (19.0±0.0 days compared with 34.0±0.72 days) (FIG. 9F), suggesting that the CD24$^+$/CD34$^+$ enriches the tumor-forming potential of bone marrow-derived NB tumor spheres.

Example 19

Screening Kits and Personalized Medicine Cancer Stem Cell Screening Kits

The present example is provided to demonstrate the utility of the present invention as providing a screening kit that may be used for the identification of specific anti-NB TIC compounds and chemical entities.

The invention provides a kit for the testing and/or screening of a patient of interest's NB TICs. In this manner, a sample of biological tissue enriched for a population of NB TICs from a patient of interest may be used to screen and/or identify a specific anti-NB TICs active agent or agents that are the most potent and/or active against a specific patient's NB TICs population. In this manner, potential therapeutic agents may be selected that is custom tailored to a particular patient.

In some embodiments, the kit would comprise an assay plate that includes a plurality of wells, each well of said assay plate being suitable for containing a pharmacologically active agent of interest, such as a potentially anti-NB TICs pharmacologically active agent. By way of example, the assay plate may comprise 40, 50, 60, 70, 80, 90, 100 or more wells. In some embodiments, the assay plate will include 96 wells, such as is customary in assay plates. As part of the kit described herein, 5, 10, 20, 25, 30, or 40 of the wells may include a different anti-NB TIC compound, such as a volume of one or more of each of the compounds listed below:

2.3-Dimethoxy-1.4-naphthoquinone,
Aklavine Hydrochloride,
Amodiaquin dihydrochloride dehydrate;
Amsacrine Hydrochloride;
Azaguanine-8;
beta-peltatin;
Camptothecine (S.+);
CGP-74514A hydrochloride;
Chelerythrine chloride;
Cholestan-3beta.5alpha.6beta-Triol;
Ciclopirox Olamine;
Clofazimine;
Colchicine;
Convallatoxin;
Crassin Acetate;
Crinamine;
Dequalinium analog. C-14 linker;
Dequalinium dichloride;
Digitoxin;
Digoxigenin;
Dihydrogambogic acid;
Dihydroouabain;
Erysolin;
Gambogic acid;
Mechlorethamine;
Meclizine hydrochloride;
MG 624;
Mitoxanthrone Hydrochloride;
Ouabain;
Oxybendazole;
Oxybendazole;
Paclitaxel;
Parthenolide;
Patulin;
Periplocymarin;
Peruvoside;
Primaquine diphosphate;
Quinacrine dihydrochloride;
Sanguinarine chloride, or Tomatine.

In this manner, a positive control is provided in the assay plate for control and/or comparative purposes.

In addition, and in some embodiments of the kit, at least one or more of the assay wells will include a volume of a pharmacologically active agent that is known and/or is in use as an anti-NB agent, such as ancitabine hydrochloride, doxorubicin hydrochloride, etoposide, or vincristine sulfate, or these agents in combination with one or more of a different anti-NB TIC compound, such as a volume of one or more of each of the compounds listed below:

2.3-Dimethoxy-1.4-naphthoquinone,
Aklavine Hydrochloride,
Amodiaquin dihydrochloride dehydrate;
Amsacrine Hydrochloride;
Azaguanine-8;
beta-peltatin;
Camptothecine (S.+);
CGP-74514A hydrochloride;
Chelerythrine chloride;
Cholestan-3beta.5alpha.6beta-Triol;
Ciclopirox Olamine;
Clofazimine;
Colchicine;
Convallatoxin;
Crassin Acetate;
Crinamine;
Dequalinium analog. C-14 linker;
Dequalinium dichloride;
Digitoxin;
Digoxigenin;
Dihydrogambogic acid;
Dihydroouabain;
Erysolin;
Gambogic acid;
Mechlorethamine;
Meclizine hydrochloride;
MG 624;
Mitoxanthrone Hydrochloride;
Ouabain;
Oxybendazole;
Oxybendazole;
Paclitaxel;
Parthenolide;
Patulin;
Periplocymarin;
Peruvoside;
Primaquine diphosphate;
Quinacrine dihydrochloride;
Sanguinarine chloride; or Tomatine.

Example 20

Personalized Medicine Cancer Stem Cell Drug Kit

The present example demonstrates the utility of the present invention for providing a personalized medicine cancer stem cell drug kit.

In some embodiments, the kit will include a multi-well assay plate, such as a standard 96-well assay plate. A volume of a potential anti-NB and/or anti-NB TIC compound/chemical entity will then be added to each well of a standard multi-well assay plate. In addition, the kit will include one or more wells to which no anti-NB or anti-NB TIC compound has been added, and will serve as the positive control in the assay.

A volume of NB TIC isolated from a patient being screened will then be added to each well of the assay plate, along with a cell viability indicator agent, such as a cell viability indicator dye, Alamar Blue. The cells will be allowed to incubate for a period of time, after which time the intensity of the cell viability indicator agent will be assessed. The wells that demonstrate the greatest inhibition of cell proliferation or survival relative to the control well will be selected for use in treating the patient having NB.

In other embodiments, and as an added control for assessing potential toxicity to normal cells, the assay multi-well plate may include 2 or more wells that will include a volume of each potential anti-NB compound of interest. To one of each of these wells will be added a number of the patients' isolated NB TIC, and to one or more of the wells will be added a number of the patients' normal cells, such as human pediatric neural-crest derived stem cells from the dermis (i.e., SKPs). A cell viability indicator agent, such as the cell viability indicator dye, Alamar Blue, will then be added to each well, and the cells allowed to incubate. The intensity of the indicator agent will then be assessed as described above. In this way, a potential anti-NB compound may be selected that causes the least amount of normal cell proliferation inhibiting activity.

In other embodiments, and as an added control for assessing potential toxicity to normal cells, the assay multi-well plate may include 2 or more wells that will include a volume of each potential anti-NB compound of interest. To one of each of these wells will be added a number of the patients' isolated NB TIC, and to one or more of the wells will be added a number of the patients' normal cells, such as human pediatric neural-crest derived stem cells from the dermis (i.e., SKPs). A cell viability indicator agent, such as the cell viability indicator dye, Alamar Blue, will then be added to each well, and the cells allowed to incubate. The intensity of the indicator agent will then be assessed as described above. In this way, a potential anti-NB compound may be selected that causes the least amount of normal cell proliferation inhibiting activity.

In yet another aspect, the invention provides a kit for the testing and/or screening of a patient of interest's TICs from tumors such as leukemia, melanoma, brain, breast, and colon. Note that Tables 7, 11, 14, and 17 identify parthenolide, a compound that specifically targets NB TICs, as a compound previously identified to target human acute myelogenous leukemia stem and progenitor cells (28), and therefore compounds identified that target NB TICs can also target TICs from other tumors.

In this manner, a sample of biological tissue enriched for a population of TICs from a patient of interest may be used to screen and/or identify a specific anti-TIC active agent or agents that are the most potent and/or active against a specific patient's TIC population, using the above compounds.

Example 21

Dual Screening Method for Compounds having Activity for Neuroblastoma and Neuroblastoma Tumor Initiating Cells The present example demonstrates the utility of the present invention as a dual screening method effective in the screening of a library of compounds and the identification of compounds for the treatment of NB, and compounds that are specifically cytostatic or cytotoxic toward NB TICs.

The screening method is a dual screening method because it employs both normal cells and NB TICs to assess the activity of a compound.

While virtually any normal cell line may be used as the normal cell population in the assay, a particular normal cell line that may be used are the FS90 and FS105 "normal" control cell lines (human Skin-derived precursors (SKPs)).

While virtually any NB TIC line may be used in the dual screen assay, a particular NB TIC line that may be used in the assay is NB12, a stage IV NB cell line that was obtained from a patient having been heavily treated for NB and having experienced multiple relapses of the disease.

Alternatively, the assay may be conducted wherein a NB patients' own normal tissue cells may be used as a control tissue in the screening assay, such as a preparation of SKPs of the NB patient. In particular, these normal tissue cells are human pediatric neural crest-derived stem cells from the dermis (SKPs) of a patient, or derived from bone cells, nerve cells or muscle cells from the same patient.

Figure 10:
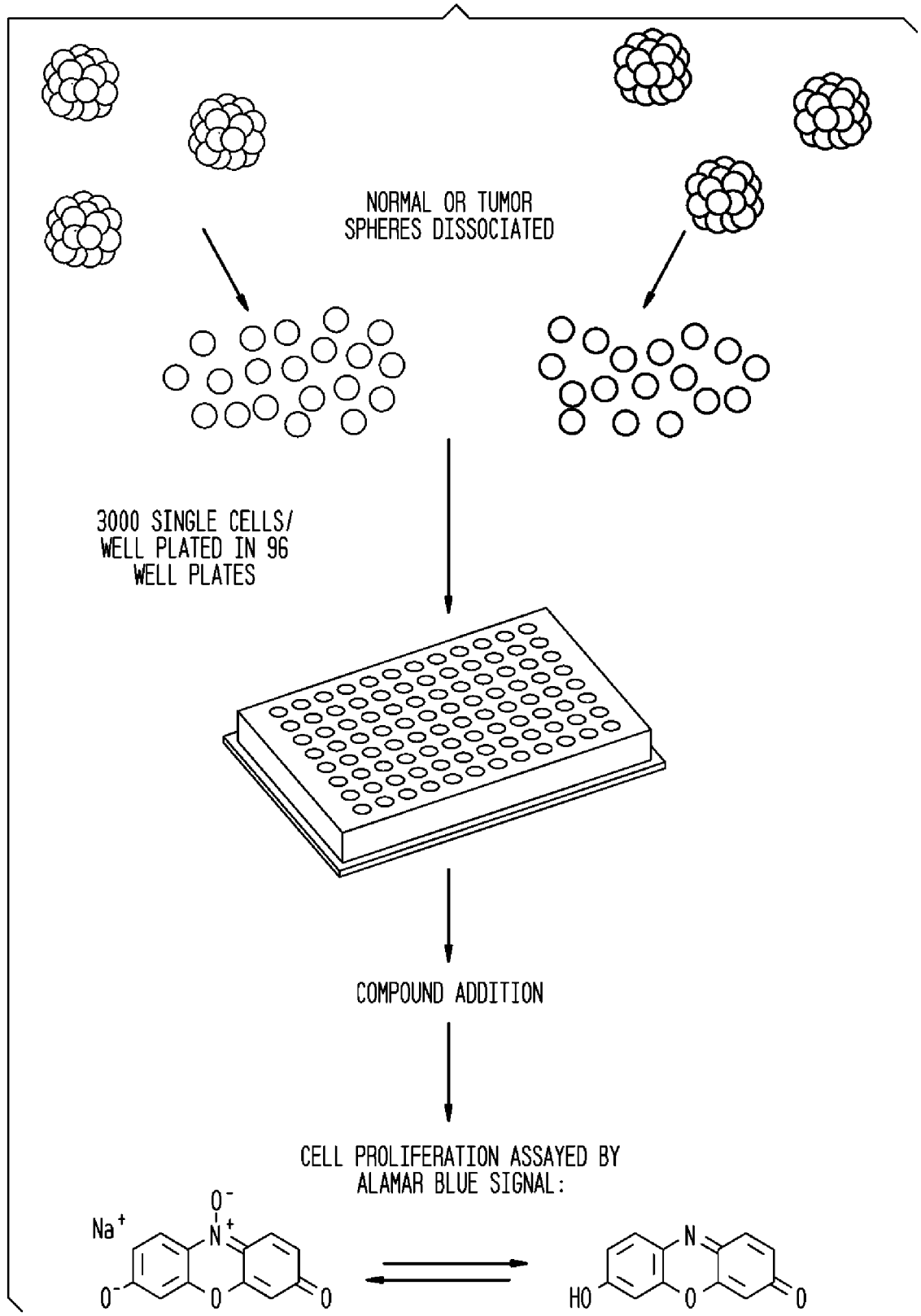
FIG. 10, according to one embodiment of the method, presents a diagrammatic flow chart demonstrating the design of the high throughput, dual-cell (Normal or Tumor cells) screening assay employed in the selection of candidate test compounds that target NB TICs. Normal or TIC spheres are dissociated; 3,000 single cells/well are plated in 96 well plates; candidate test compound is added; cell proliferation assayed by Alamar Blue signal. Blue/nonfluorescent compound is converted to a red/fluorescent compound under reducing conditions such as those produced by live cells. The magnitude of the fluorescent signal is proportional to the metabolic activity of the cell sample.
Figure 11:
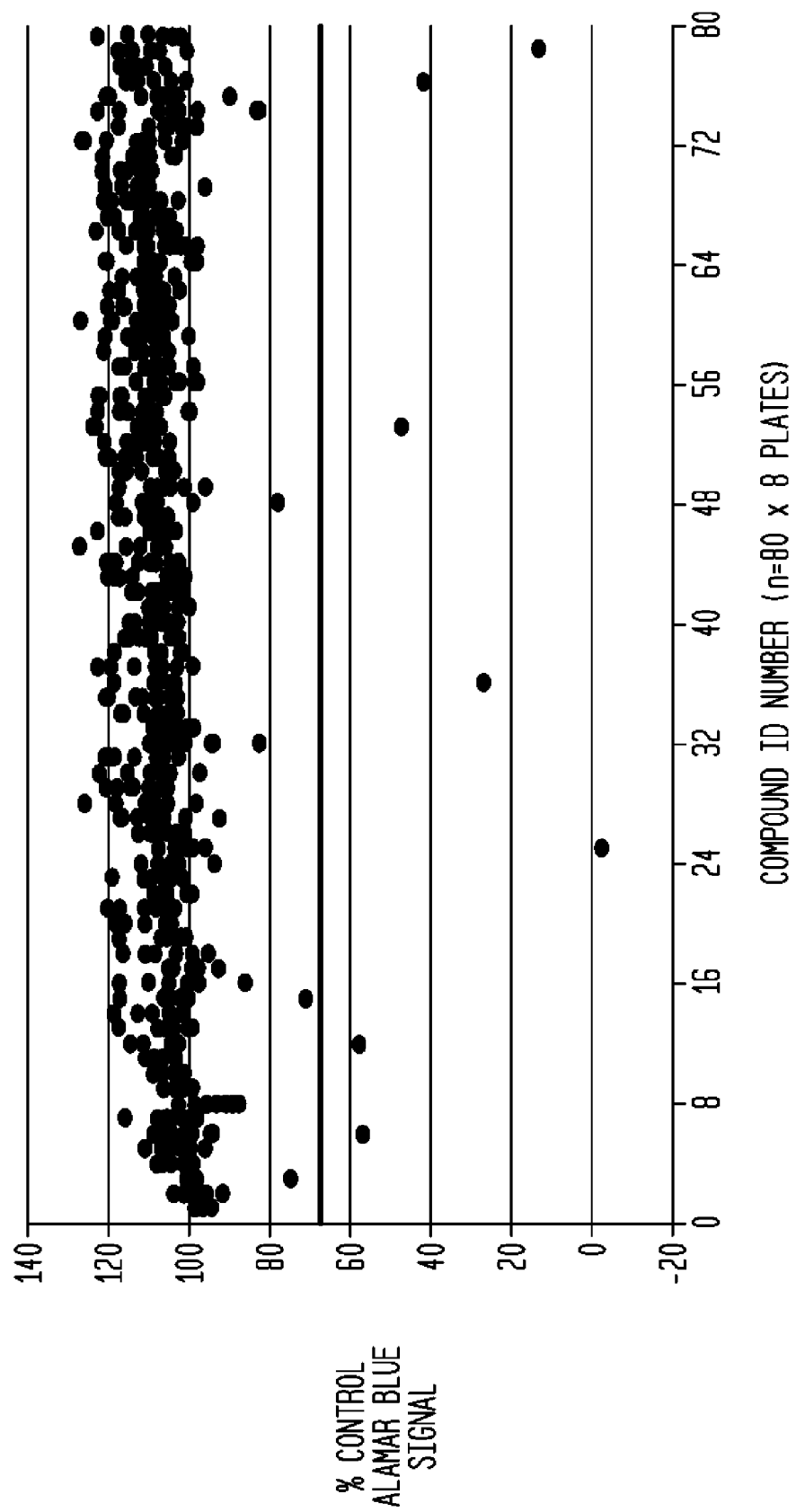
FIG. 11, according to one embodiment of the invention, presents the results from a study wherein FS90 (normal human SKPs, passage 3) cells were treated with the LOPAC™ library of chemical compounds. alamarBlue® (a cell viability and proliferation indicator) was added after 30 hours and fluorescence intensity read after an additional 24 hours. The hit cutoff is indicated in the graph by the thick line across the graph at the Y axis value of about 69.00% Control alamarBlue® Signal (which corresponds to 3 standard deviations from the mean of all test samples). Nine compounds whose alamarBlue® signals fall below this line were identified as primary hits in this study. (X axis presents the Compound ID number (n=80×8 plates); Y axis presents the % Control alamarBlue® Signal).
Figure 12A:
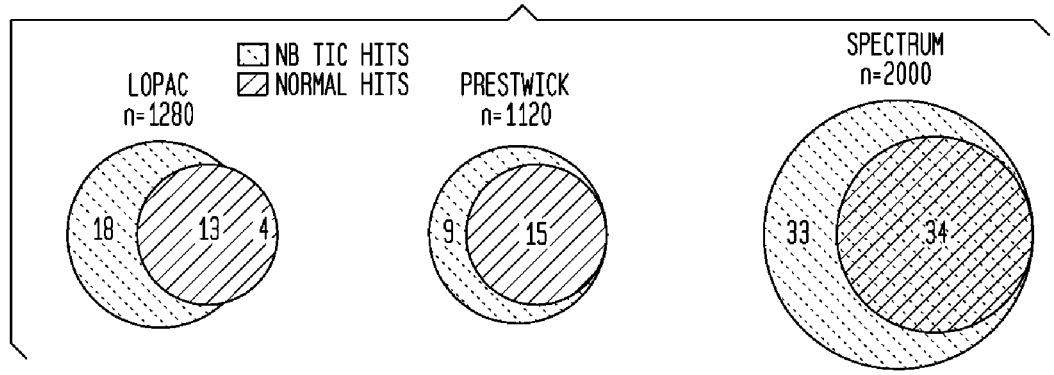
FIG. 12A-12C, according to one embodiment of the invention, presents the study results from primary screens of the chemical libraries examined. 12A presents the results of the primary screen in Venn diagram form. The Venn diagrams depict the primary hits from each library. Compounds in the gray-bordered circles (left circle) affected the tumor-initiating cells, while compounds in the black-bordered circles (right circle) affected normal cells. Compounds that affected both cell types lie in the overlap region. Note that there is some compound redundancy between the libraries. 12B presents the confirmed primary hits in Venn diagram form. Primary hits were retested against NB12, FS90 and FS105 (normal human SKPs). 87% of the primary hits were confirmed in this step, yielding 54 unique compounds that target tumor-initiating cells, 4 unique compounds that target normal cells, and 46 compounds that have activity against both normal and tumor cells (overlap region). 12C presents in a pie-format the classification of primary hits by mechanism of action. (Solid light gray area=DNA damaging agents/cell cycle inhibitors; Solid dark gray area=Na+/K+ ATPase inhibitors; Diagonal striped area=Neuronal receptor effectors; Vertical striped area=Other; Solid white area=Metabolic inhibitor; Checkerboard area=Neuronal channel effectors; Dotted area=Specific protein effectors).
Figure 12B:
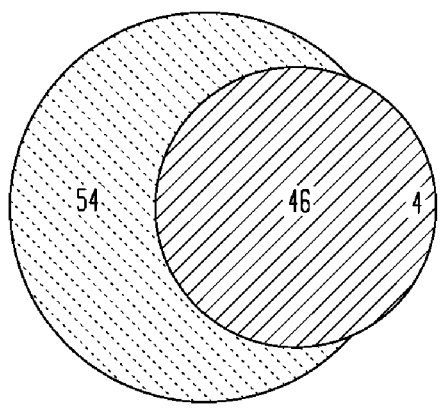
Figure 12C:
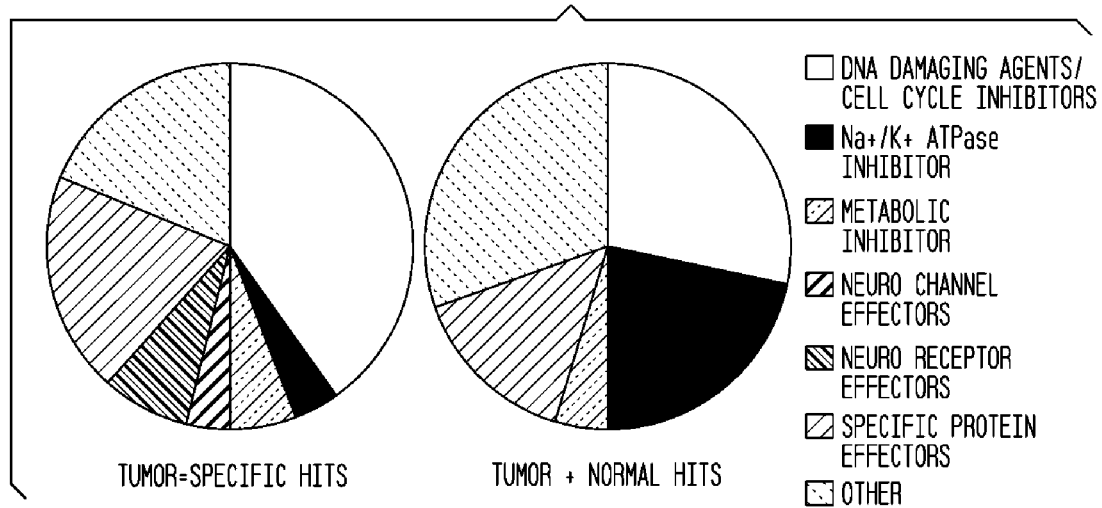
Figure 14B:
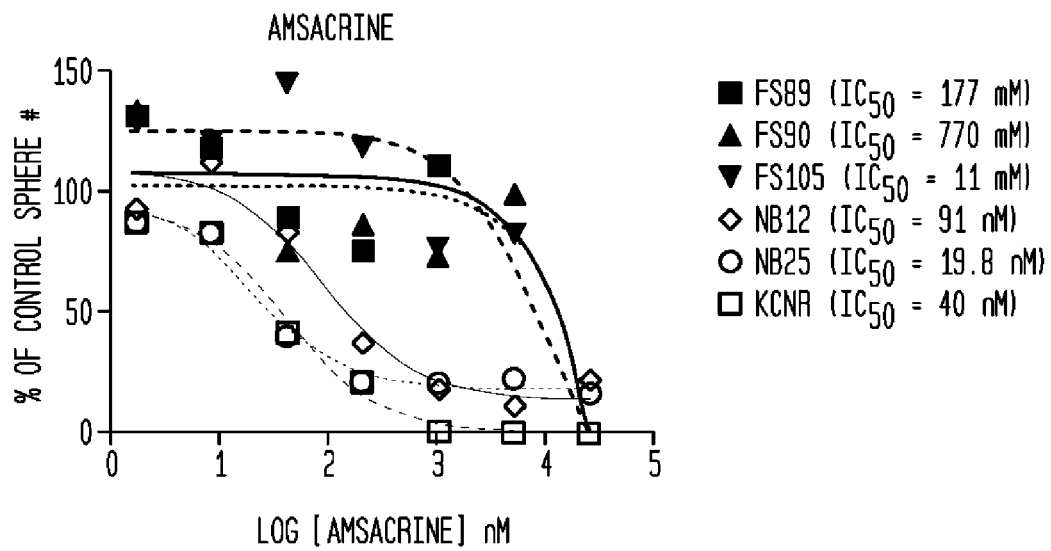
Figure 14C:
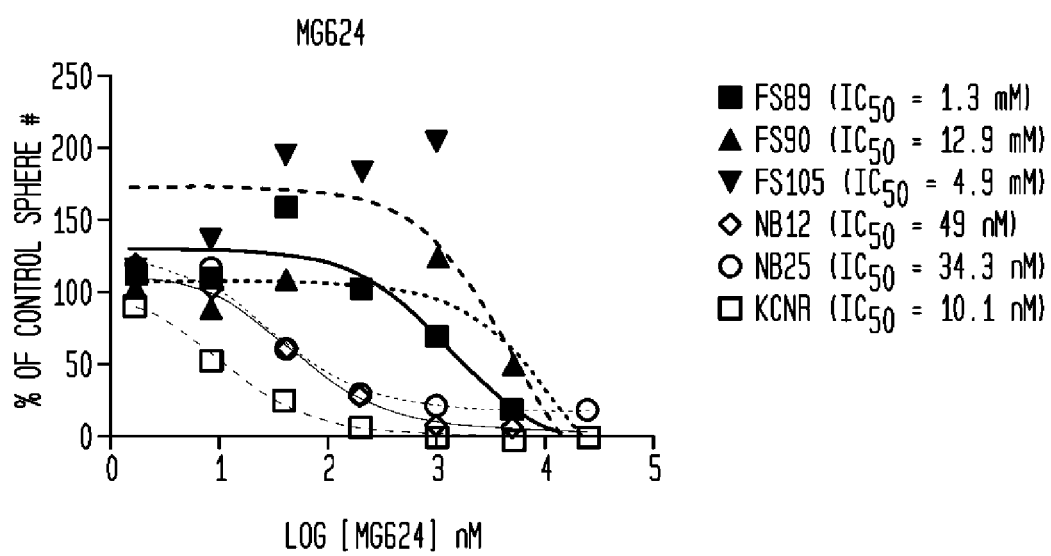
Figure 15A:
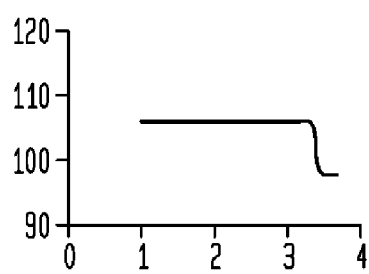
FIG. 15A-15FF, according to one embodiment of the invention, presents $IC_{50}$ values for 32 selected compounds from the LOPAC™ and PRESTWICK CHEMICAL LIBRARY® collections. Tumor-initiating cells (NB12) and normal cells (FS90) were treated with 10 serial dilutions of compounds ranging from 5 μM to 9 nM. Cell survival/growth was assayed using alamarBlue® and the percentage of control alamarBlue® signal was plotted versus log[compound] nM. IC50 values for NB12 are given above each plot.
Figure 15B:
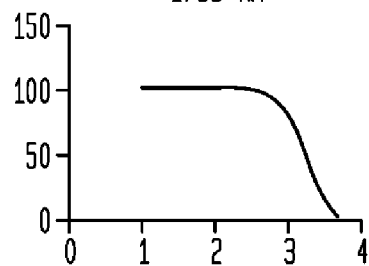
Figure 15C:
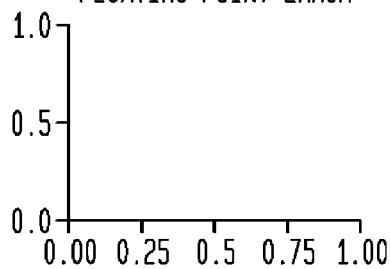
Figure 15D:
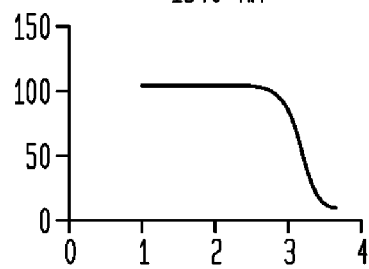
Figure 15E:
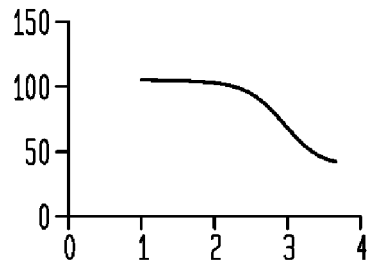
Figure 15F:
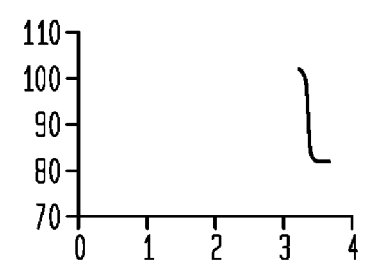
Figure 15G:
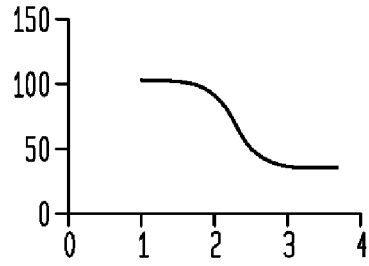
Figure 15H:
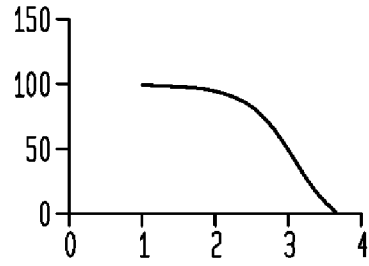
Figure 15I:
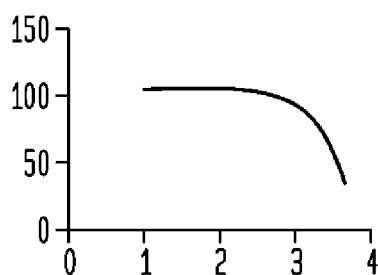
Figure 15J:
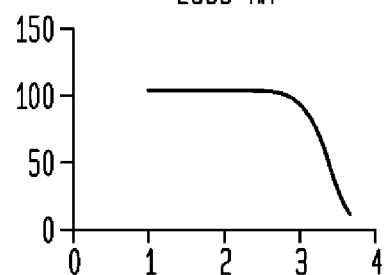
Figure 15K:
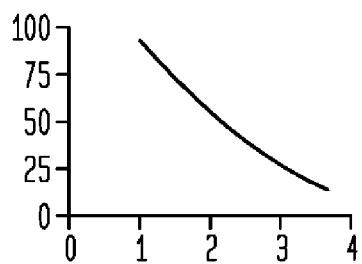
Figure 15L:
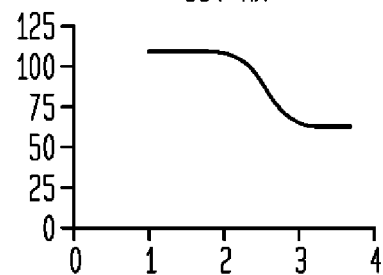
Figure 15M:
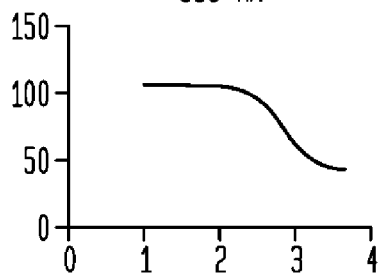
Figure 15N:
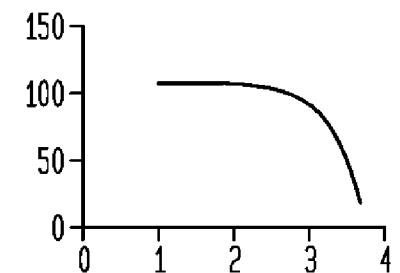
Figure 15O:
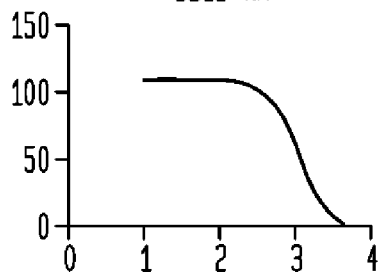
Figure 15P:
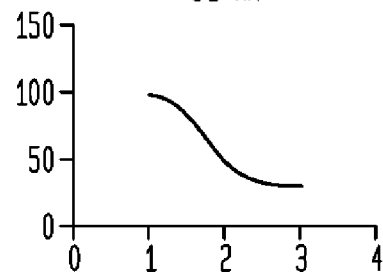
Figure 15Q:
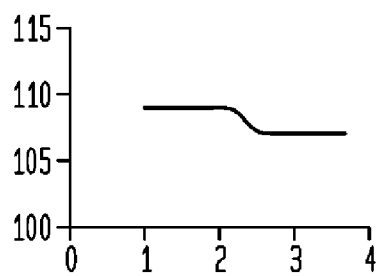
Figure 15R:
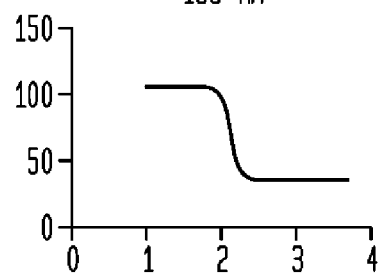
Figure 15S:
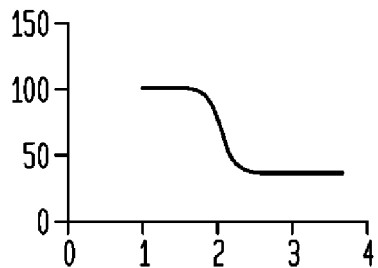
Figure 15T:
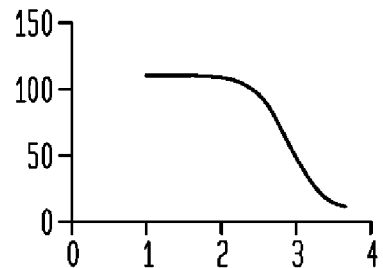
Figure 15U:
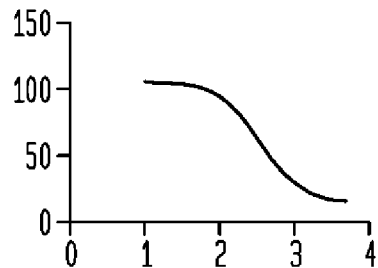
Figure 15V:
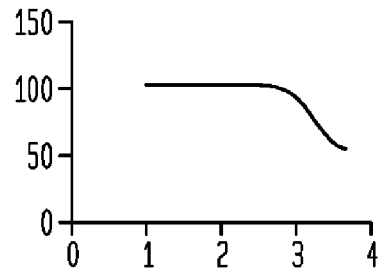
Figure 15W:
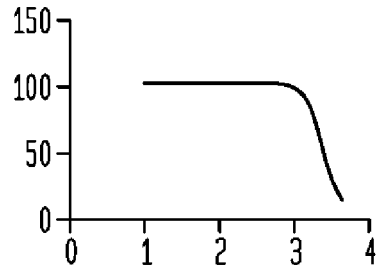
Figure 15X:
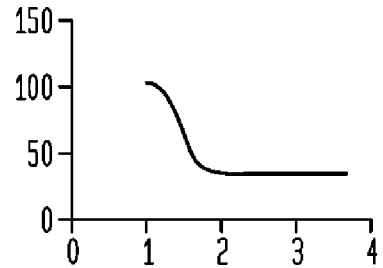
Figure 15Y:
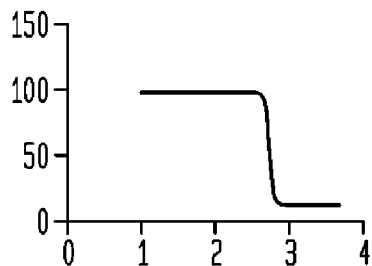
Figure 15Z:
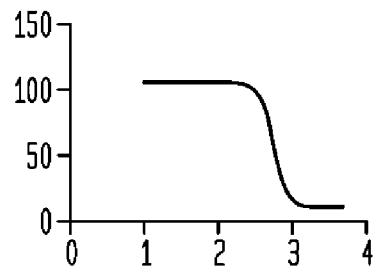
Figure 15A:
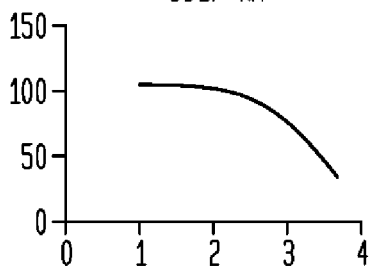
Figure 15B:
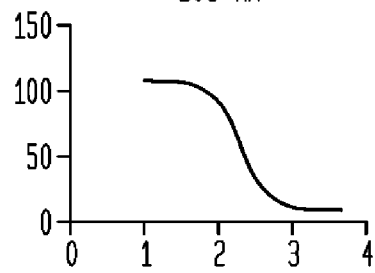
Figure 15C:
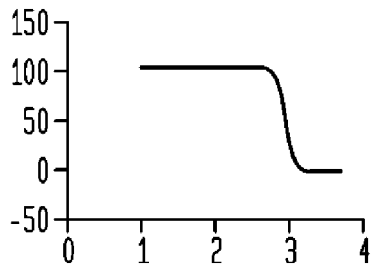
Figure 15D:
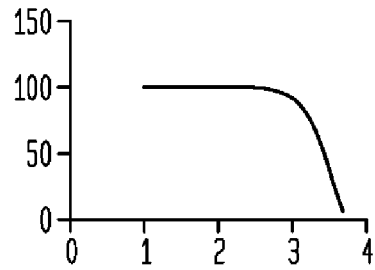
Figure 15E:
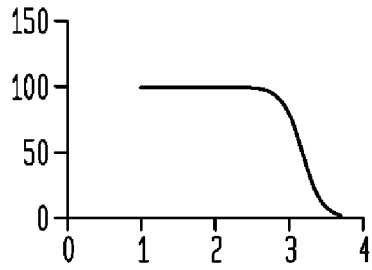
Figure 15F:
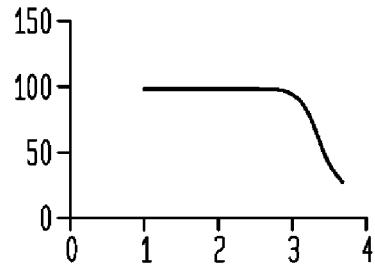
Figure 16B:
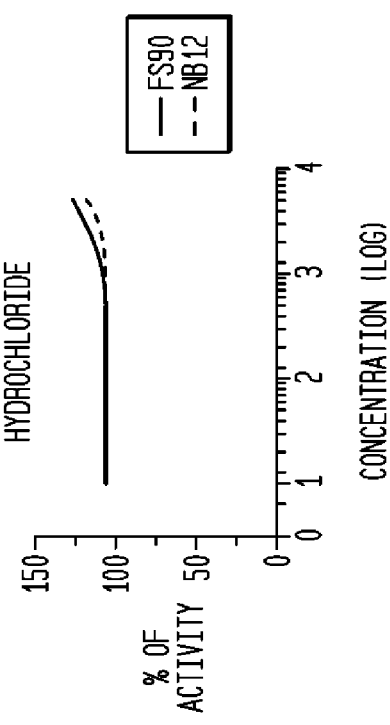
FIG. 16A-16FF, according to one embodiment of the invention, represents $IC_{50}$ values determined for 32 selected compounds from the LOPAC™, PRESTWICK CHEMICAL LIBRARY®, and SPECTRUM™ collections. Tumor-initiating cells (NB 12) and normal cells (FS90) were treated with 10 serial dilutions of compounds ranging from 5 μM to 9 nM. Cell survival/growth was assayed using alamarBlue® and the percentage of control alamarBlue® signal was plotted versus log[compound] nM (FS90 in dashed line, NB12 in bolded line). $IC_{50}$ values for NB12 and FS90 are given beside each plot.
Figure 16D:
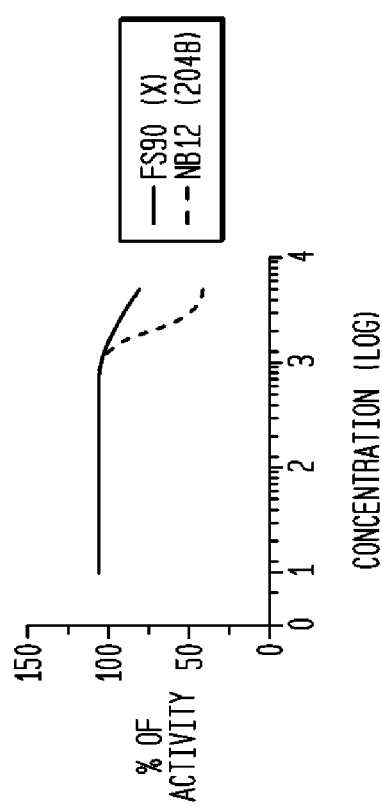
Figure 16A:
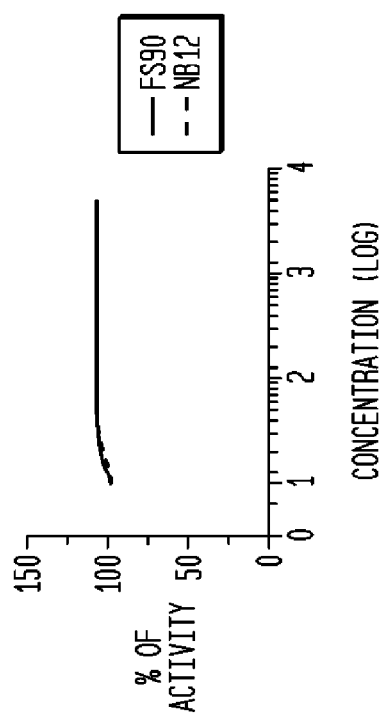
Figure 16C:
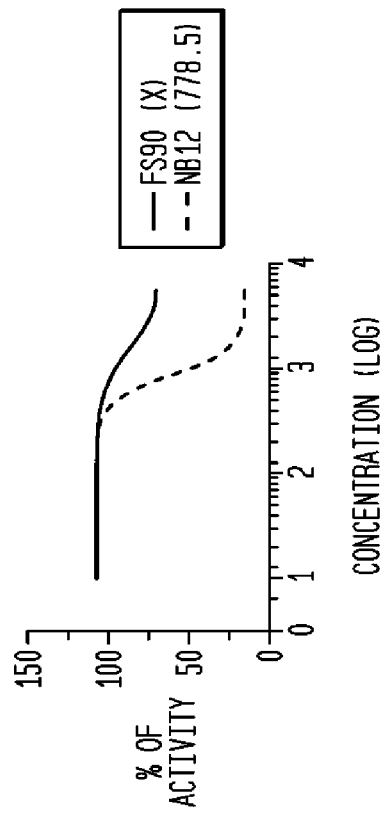
Figure 16F:
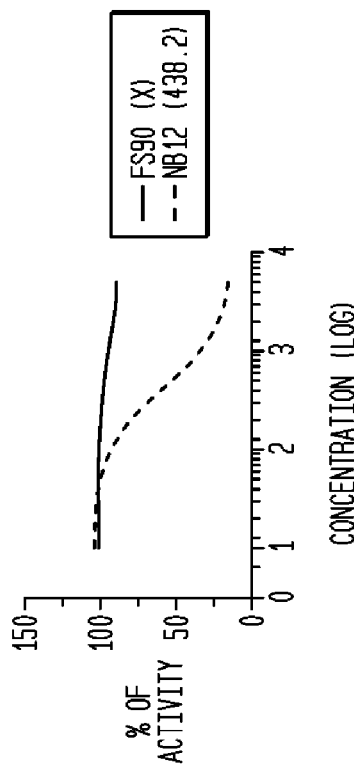
Figure 16H:
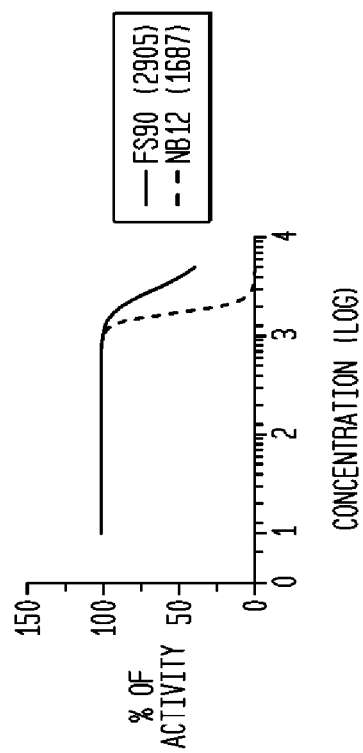
Figure 16E:
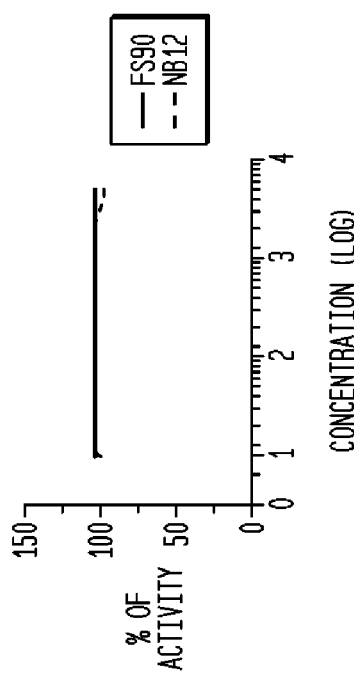
Figure 16G:
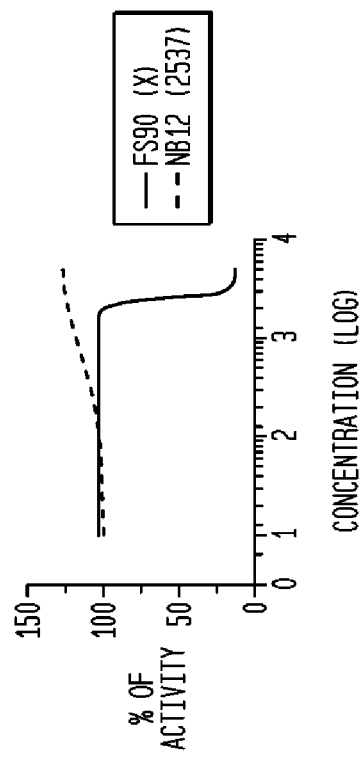
Figure 16I:
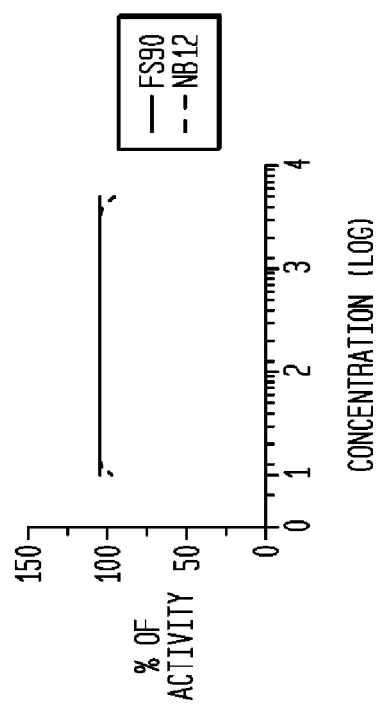
Figure 16J:
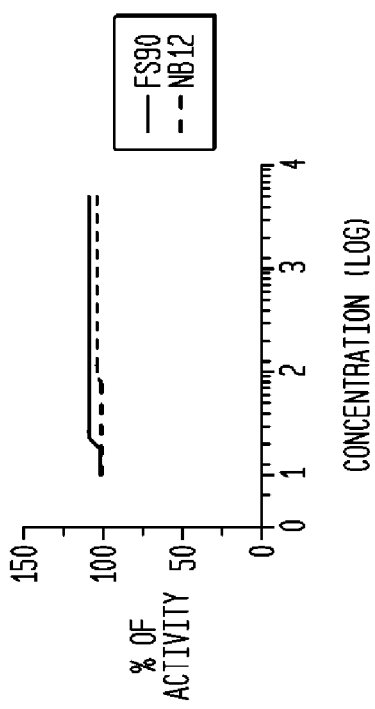
Figure 16K:
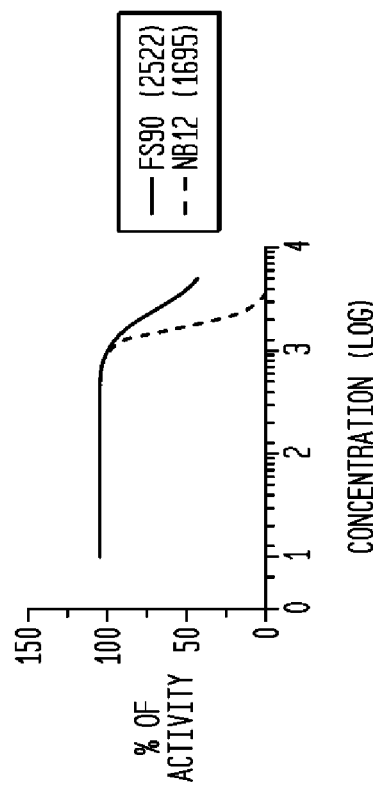
Figure 16L:
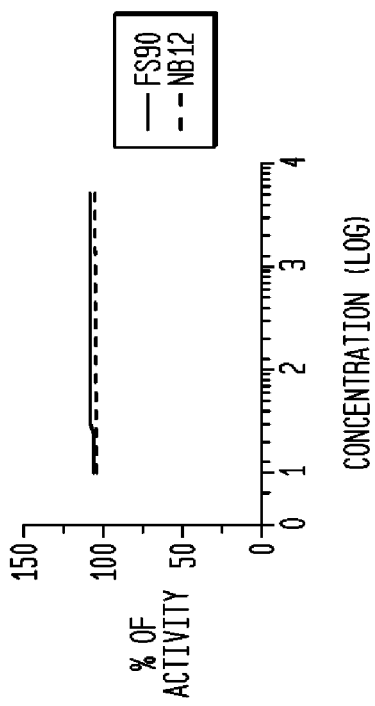
Figure 16N:
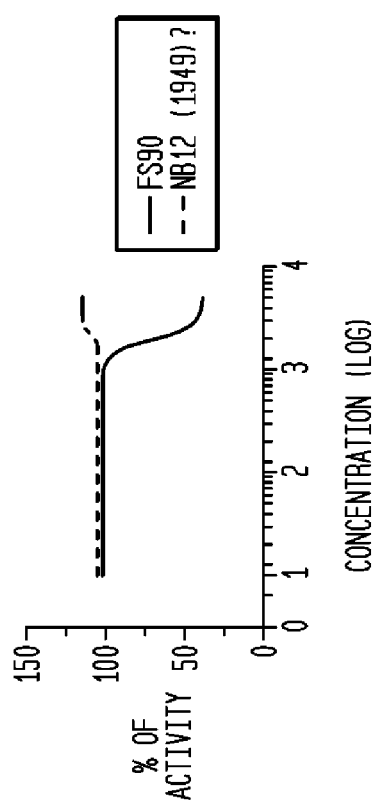
Figure 16P:
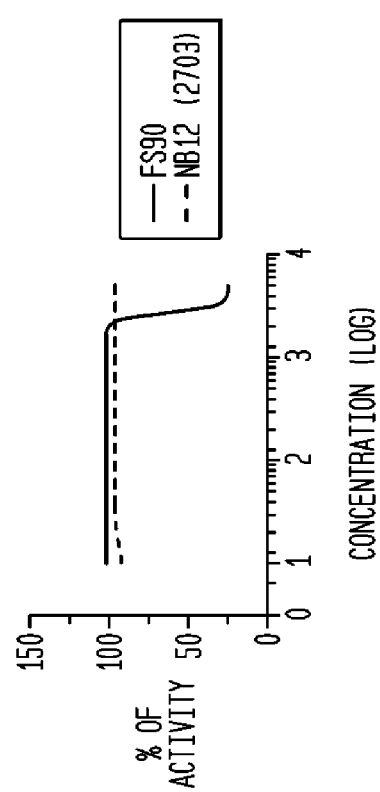
Figure 16M:
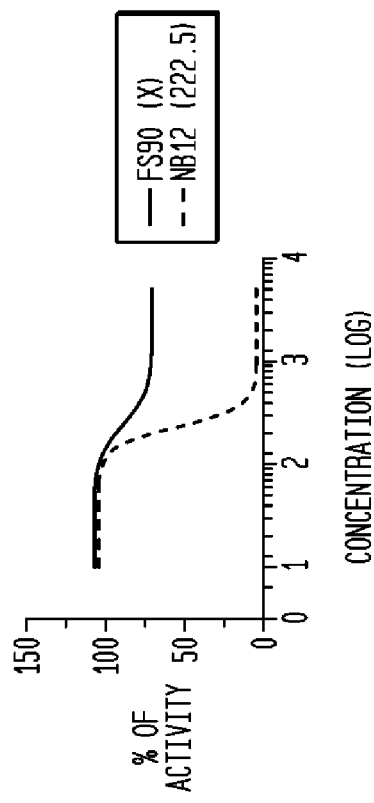
Figure 16O:
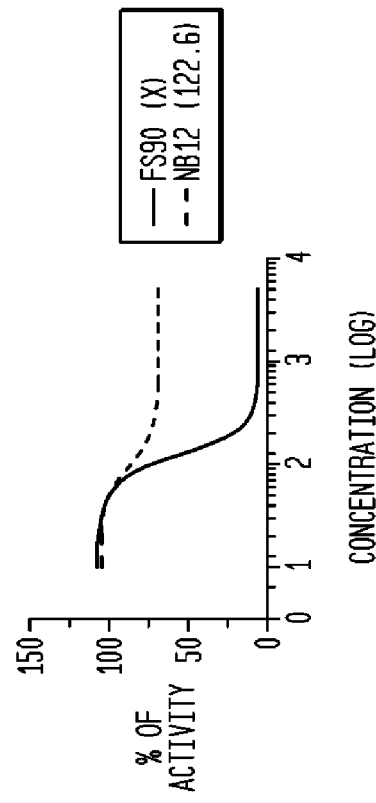
Figure 16U:
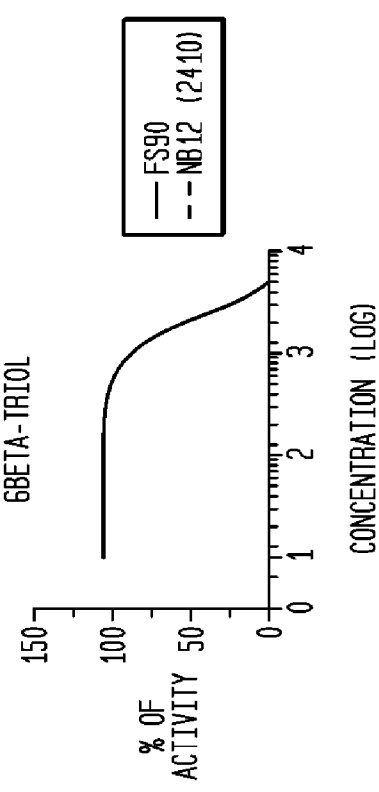
Figure 16V:
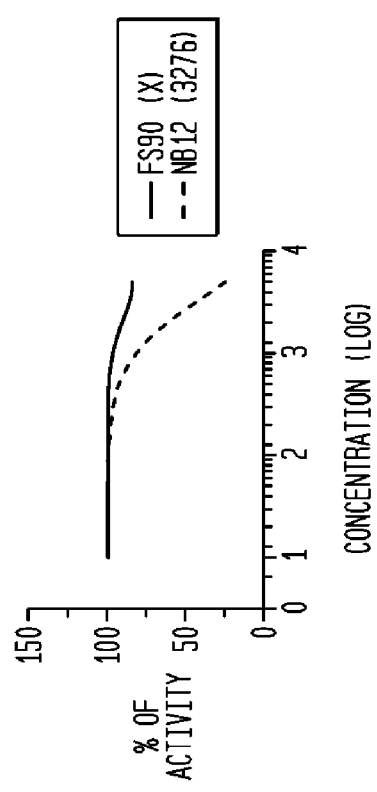
Figure 16W:
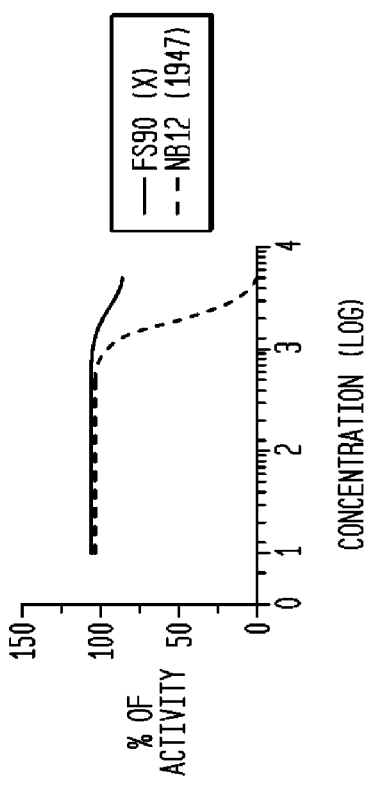
Figure 16X:
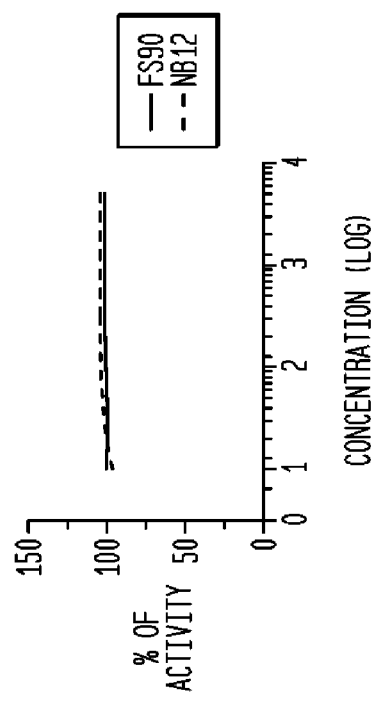
Figure 16Z:
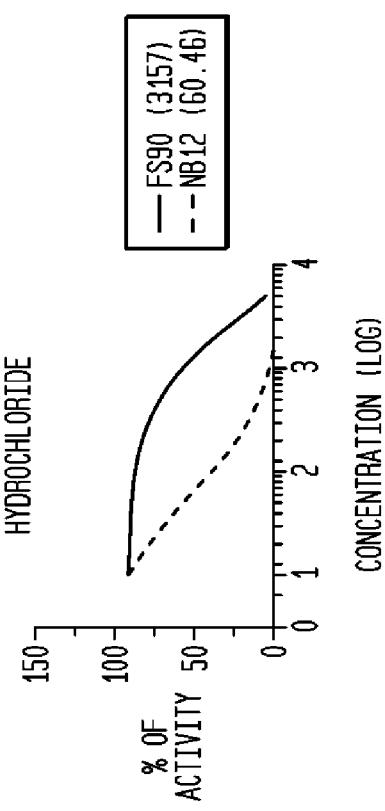
Figure 16B:
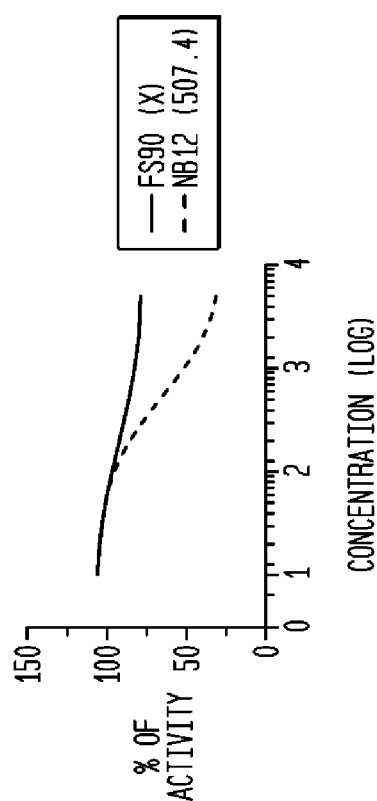
Figure 16Y:
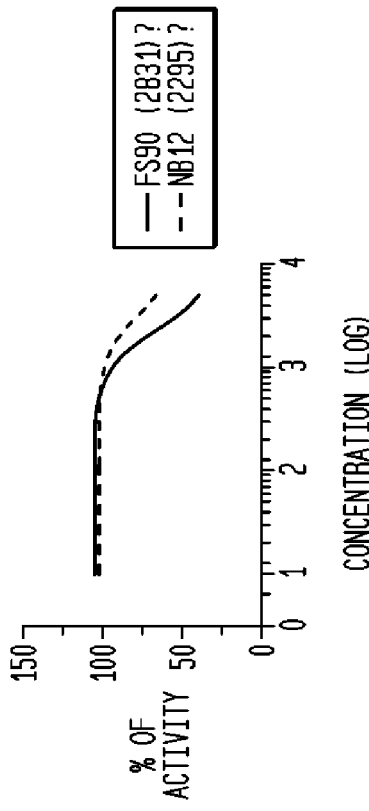
Figure 16A:
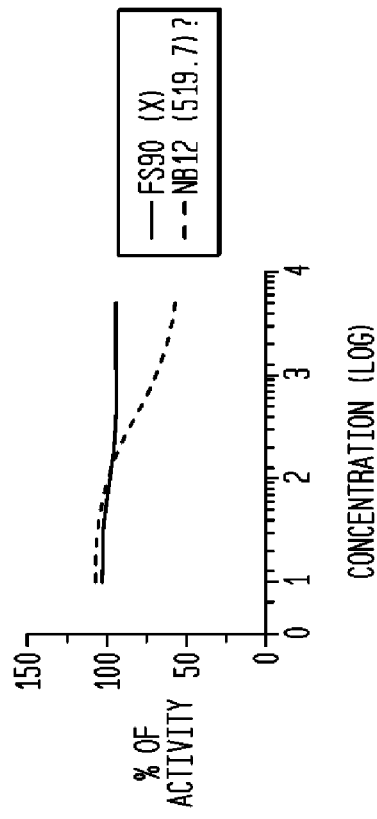
Figure 16C:
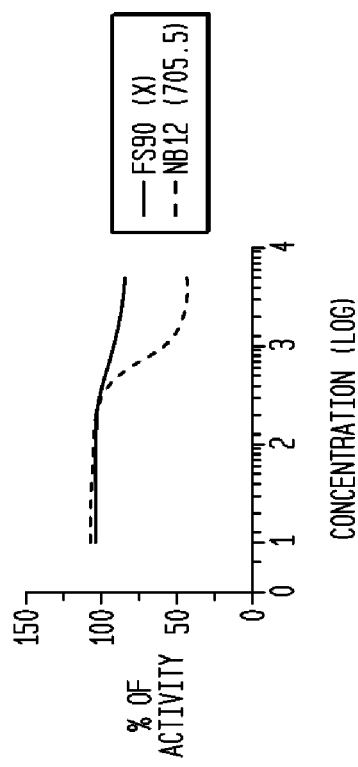
Figure 16E:
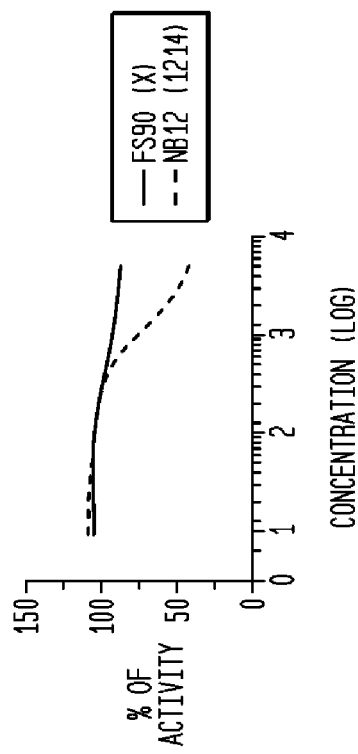
Figure 16D:
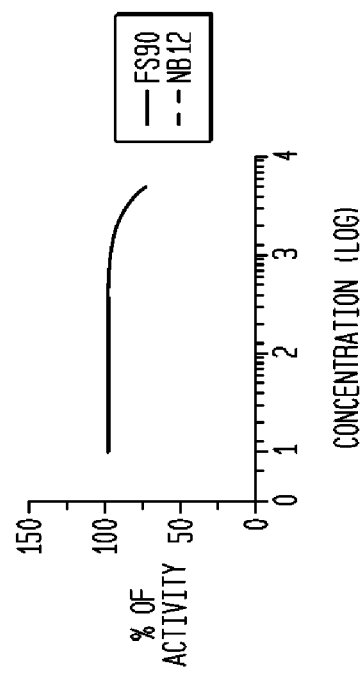
Figure 16F:
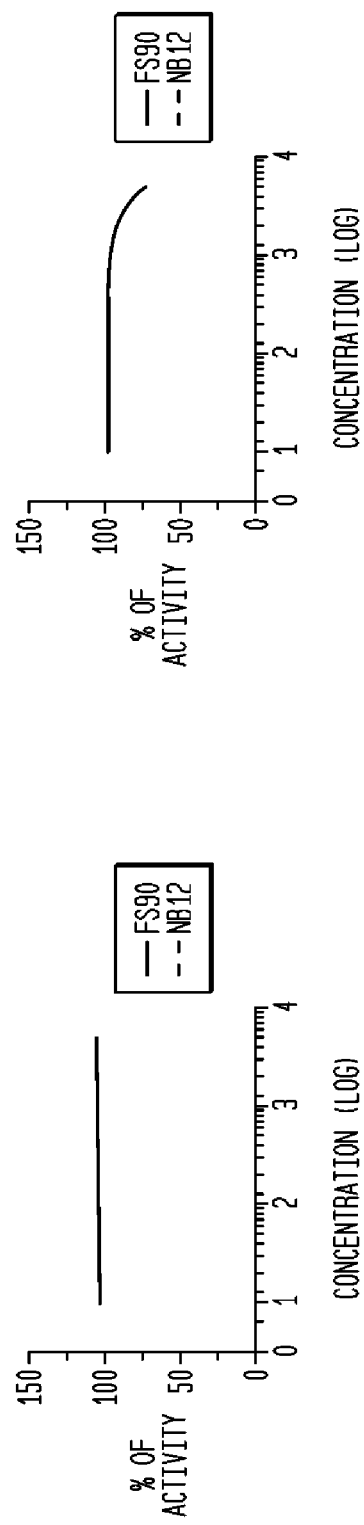

Turning now to the diagram provided at FIG. 10, a sample of normal tissue cells is dissociated into spheres to provide a control cell dissociated sample of cells; a sample of NB tumor cells is dissociated into spheres to provide a test cell dissociated sample of cells; depositing a number of cells from the control cell dissociated sample of cells into a desired number of wells of a multi-well assay plate to provide control cell wells; depositing the same number of cells from the test cell dissociated sample of cells into a desired number of wells of the multi-well assay plate to provide test cell wells; adding a volume of a potential anti-NB compound to each of said control cell wells and to each of said test cell wells to provide a loaded multi-well assay plate; incubating said loaded multi-well assay plate; adding a cell proliferation or survival indicator agent to each well of said loaded multi well assay plate; and assessing indicator agent intensity in each well of said loaded multi-well assay plate, and selecting potential anti-NB compounds that elicit a cell proliferation or survival indicator agent intensity that is two (2) fold or more less intense than the indicator agent intensity observed in the control wells.

In some embodiments, the cell proliferation or survival indicator agent is a cell viability dye, such as alamarBlue®. In these embodiments, cell proliferation is assesed as with alamarBlue® intensity used in an alamarBlue® assay. In application the alamarBlue® signal observed was linear with time, there was minimal background, and there was low variability between wells and plates (CV 3.5-4.5%, Z>0.5), and there was a greater tan 10-fold difference between control and background fluorescence readings. In the trials run, the anti-NB compounds that were selected ("hits") elicited a signal indicator intensity that was shifted three (3) standard deviations from the mean signal indicator intensity.

The screening assay may also include positive control compound wells, wherein a known anti-NB TIC or known anti-NB therapeutic agent, is added to one or more wells containing control cells and to one or more wells containing NB cells. By way of example, such known anti-NB therapeutic agents are ancitabine hydrochloride, doxorubicin hydrochloride, etoposide, or vincristine sulfate. In this manner, each assay will have its own positive control reference for assessing viability in the assay run.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

Bibliography

The references listed below as well as the references cited throughout the specification are incorporated herein by reference to the extent that they supplement, explain, provide a background for or teach methodology, techniques and/or compositions employed herein.

1. Brodeur G M. (2003), *Nat Rev Cancer*, 3:203-16.
2. Maris J M. (2005), *Curr Opin Pediatr*, 17:7-13.
3. van Limpt V., et al. (2005), *Cancer Lett*, 228:59-63.
4. Pardal, R., et al. (2003), *Nat Rev Cancer*, 3:895-902.
5. Beachy, P. A., et al. (2004), *Nature*, 432:324-31.
6. Warner, J. K., et al. (2004), *Oncogene*, 23:7164.
7. Hamburger, A. & Salmon, S. E. (1997), *J Clin Invest*, 60:846-54.
8. Heppner, G. H. (1984), *Cancer Res*, 44:2259-65.
9. Singh, S. K., et al. (2004), *Oncogene*, 23:7267-73.
10. Al-Hajj, M. & Clarke, M. F. (2004), *Oncogene*, 23:7274-82.
11. Lapidot T, et al. (1994), *Nature*, 367:645-8.
12. Bonnet D, Dick J E. (1997), *Nat Med*, 3:730-7.
13. Al-Hajj, M., (2003), *Proc Natl Acad Sci USA*, 100:3983-8.
14. Singh, S. K. et al. (2004), *Nature*, 432:396-401.
15. van Noesel M M, et al. (1997), *Cancer*, 80:834-43.
16. Toma, J. G. et al. (2001), *Nat Cell Biol*, 3:778-84.
17. Fernandes K J, et al. (2004), *Nat Cell Biol*, 6:1082-93.
18. Toma J G, et al. (2005), *Stem Cells*, 23:727-37.
19. Christiansen J H, (2000), *Curr Opin Cell Biol*, 12:719-24.
20. Ambros P F, et al. (2003), *Cancer Lett*, 197:29-34.
21. Miettinen M, et al. (1998), *Am J Surg Pathol*, 22:327-32.00.
22. LaBrosse E H, et al. (1976), *J Natl Cancer Inst*, 57:633-80
23. Barnabe-Heider F, Miller F D. (2003), *J Neurosci*, 23:5149-60.
24. Marsh H N, et al. (2003), *J Cell Biol*, 163:999-1010.
25. Lo Piccolo M S, Cheung N K, Cheung I Y. (2001), *Cancer*, 92:924-31.
26. Fernandes K J, et al. (2006), *Exp Neurol*, 201:32-48.
27. Hafer R, et al. (1999), *J Neuroimmunol*, 96:201-6.
28. Khanna C, et al. (2002), *In Vivo*, 16:77-85.
29. Nakagawara A, Ohira M. (2004), *Cancer Lett*, 204:213-24.
30. Ohira M, et al (2005), *Cancer Cell*, 7:337-50.
31. Weiss W A, et al. (1997), *EMBO J*, 16:2985-95.
32. ElShamy W M, Fridvall L K, Ernfors P. (1998), *Neuron*, 21:1003-15.
33. Lasorella A, et al (2002) *Cancer Res*, 62:301-6.
34. Valsesia-Wittmann S, et al. (2004), *Cancer Cell*, 6:625-30.
35. Dubreuil V, et al. (2000), *Development*, 127:5191-201.
36. Pattyn A, (2000), *Mol Cell Neurosci*, 15:235-43.
37. Pozniak C D,(2000), *Science*, 289:304-6.
38. Casciano I, et al. (2002), *Cell Death Differ*, 9:246-51.
39. Matsumoto K, etal. (1995), *Cancer Res*, 55:1798-806
40. Jaboin J, et al. (2002), *Cancer Res*, 62:6756-63.
41. Kaplan D R, et al. (1993), *Neuron*, 11:321-31.
42. Lucarelli E, et al. (1997), *Eur J Cancer*, 33:2068-70.
43. Lavoie J F, et al. (2005), *J Biol Chem.*, 280:29199-207.
44. Wartiovaara K, et al. (2002), *J Neurosci*, 22:815-24.
45. Atwal J K, et al (2000), *Neuron*, 27:265-77.
46. Toma J G, et al. (2000), *J Neurosci*, 20:7648-56.
47. Ellis J, Yao S. (2005), *Curr Gene Ther*, 5:367-73.
48. Ellis J., (2005), *Human Gene Ther*, 16:1241-6.
49. Mckenzie I A, et al. (2006), *J Neurosci*, 26:6651-60.
50. Torkin R, et al. (2005), *Mol Cancer Ther*, 4:1-11.
51. Barnabe-Heider F, et al. (2005), *Neuron*, 48: 253-65.
52. U.S. Pat. No. 6,787,355—Miller, et al. (2004).
53. Guzman, M L., et al.(2005), *Blood*, 105(11): 4163-9.
54. Singh S K, et al. (2003), *Cancer Res*, 63:5821-28.
55. Reynolds B A & Weiss S. (1996), *Dev Biol;* 175:1-13.
56. Clarke M F, et al. (2006), *Cancer Res*, 66:9339-44.
57. Fang D, et al. (2005), *Cancer Res;* 65:9328-37.
58. Nagai J, et al. (2000), *J Pediatr Hematol Oncol*, 22:20-6.
59. Bata-Csorgo Z, et al. (1993), *J Exp Med* 8:1271-81.
60. Akashi T, et al. (1994), Virchows Arch, 425:399-406.
61. Ponti D, et al. (2005), *Cancer Res*, 65:5506-11.
62. Choi H S, et al. (2005), *Pediatr Blood Cancer*, 45:68-71.

What is claimed is:

1. A composition comprising an enriched population of neuroblastoma tumor-initiating cells (TICs) derived from a bone marrow aspirate or a tumor sample taken from the body of an individual having neuroblastoma disease, wherein the enriched population of neuroblastoma TICs comprise a non-adherent sphere of cells grown in serum-free conditions.

2. The composition of claim 1, wherein the non-adherent sphere of cells are grown in serum-free conditions from at least one cell of the bone marrow aspirate.

3. The composition of claim 2, wherein the at least one cell of the bone marrow aspirate is derived from a bone marrow metastasis present in the bone marrow aspirate, and wherein the bone marrow metastasis is captured on a cell strainer by filtering the bone marrow aspirate through the cell strainer.

4. The composition of claim 3, wherein the at least one cell of the bone marrow aspirate is dissociated from other cells of the bone marrow metastasis by enzymatic digestion or mechanical disruption prior to being grown in serum-free conditions to form the non-adherent sphere of cells.

5. The composition of claim 1, wherein the non-adherent sphere of cells are grown in serum-free conditions from at least one cell of the tumor sample.

6. The composition of claim 5, wherein the at least one cell of the tumor sample is dissociated from other cells of the tumor sample by enzymatic digestion or mechanical disruption prior to being grown in serum-free conditions to form the non-adherent sphere of cells.

7. The composition of claim 1, wherein the non-adherent sphere of cells are grown in a defined medium containing fibroblast growth factor (FGF) and epidermal growth factor (EGF).

8. The composition of claim 1, wherein greater than 2% of cells of the enriched population of neuroblastoma TICs are each able to form a secondary sphere of cells in a methylcellulose assay.

9. The composition of claim 8, wherein between about 3% and about 18% of cells of the enriched population of neuroblastoma TICs are each able to form a secondary sphere of cells in a methylcellulose assay.

10. The composition of claim 1, wherein the enriched population of neuroblastoma TICs are enriched about 100-fold in their ability to form secondary spheres in a methylcellulose assay compared to non-enriched cells from the bone marrow aspirate or the tumor sample.

11. The composition of claim 1, wherein about 1% of the cells of the enriched population of neuroblastoma TICs are each able to form tumors in vivo in an animal xenograph model.

12. The composition of claim 11, wherein the animal xenograph model comprises injecting cells subcutaneously into mice.

13. The composition of claim 11, wherein the animal xenograph model comprises injecting cells into the adrenal fat pad of mice.

14. The composition of claim 1, wherein the enriched population of neuroblastoma TICs are enriched at least about 100-fold in their ability to form tumors in vivo in an animal xenograph model compared to a non-enriched population of cells of the bone marrow aspirate or the tumor sample.

15. The composition of claim 1, wherein the enriched population of neuroblastoma TICs are enriched at least about 1,000-fold in their ability to form tumors in vivo in an animal xenograph model compared to a non-enriched population of cells of the bone marrow aspirate or the tumor sample.

16. The composition of claim 1, wherein the enriched population of neuroblastoma TICs are enriched at least about 10,000-fold in their ability to form tumors in vivo in an animal xenograph model compared to a non-enriched population of cells of the bone marrow aspirate or the tumor sample.

17. The composition of claim 1, wherein the enriched population of neuroblastoma TICs are enriched about 20,000-fold in their ability to form tumors in vivo in an animal xenograph model compared to a non-enriched population of cells of the bone marrow aspirate or the tumor sample.

18. The composition of claim 1, wherein the bone marrow aspirate or the tumor sample is taken from the body of an individual having Stage 1, Stage 2, or Stage 4S neuroblastoma disease.

19. The composition of claim 1, wherein the bone marrow aspirate or the tumor sample is taken from the body of an individual having Stage 3 or Stage 4 neuroblastoma disease.

20. The composition of claim 1, wherein the individual having neuroblastoma disease is a human individual.

21. The composition of claim 20, wherein the human individual is 12 years of age or younger.

22. The composition of claim 1, wherein one or more cells of the enriched population of neuroblastoma TICs differentiate and form nestin positive and βIII-tubulin positive neurons under neurogenic conditions.

* * * * *

UNITED STATES PATENT AND TRADEMARK OFFICE
CERTIFICATE OF CORRECTION

PATENT NO. : 7,632,678 B2
APPLICATION NO. : 11/562798
DATED : December 15, 2009
INVENTOR(S) : Hansford et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 253 days.

Signed and Sealed this

Second Day of November, 2010

David J. Kappos
*Director of the United States Patent and Trademark Office*